(12) United States Patent
Zhao et al.

(10) Patent No.: US 11,091,743 B2
(45) Date of Patent: Aug. 17, 2021

(54) UDP-DEPENDENT GLYCOSYLTRANSFERASE FOR HIGH EFFICIENCY PRODUCTION OF REBAUDIOSIDES

(71) Applicant: AMYRIS, INC., Emeryville, CA (US)

(72) Inventors: Lishan Zhao, Emeryville, CA (US); Wenzong Li, Emeryville, CA (US); Gale Wichmann, Berkeley, CA (US); Aditi Khankhoje, Emeryville, CA (US); Chantal Garcia De Gonzalo, Richmond, CA (US); Tina Mahatdejkul-Meadows, Milpitas, CA (US); Shaina Jackson, Oakland, CA (US); Michael Leavell, Richmond, CA (US); Darren Platt, San Francisco, CA (US)

(73) Assignee: AMYRIS, INC., Emeryville, CA (US)

(*) Notice: Subject to any disclaimer, the term of this patent is extended or adjusted under 35 U.S.C. 154(b) by 0 days.

(21) Appl. No.: 16/323,756

(22) PCT Filed: Aug. 11, 2017

(86) PCT No.: PCT/US2017/046637
§ 371 (c)(1),
(2) Date: Feb. 6, 2019

(87) PCT Pub. No.: WO2018/031955
PCT Pub. Date: Feb. 15, 2018

(65) Prior Publication Data
US 2019/0185826 A1 Jun. 20, 2019

Related U.S. Application Data

(60) Provisional application No. 62/374,408, filed on Aug. 12, 2016.

(51) Int. Cl.
| | |
|---|---|
| *C12N 9/10* | (2006.01) |
| *A23L 2/60* | (2006.01) |
| *C12P 19/56* | (2006.01) |
| *C12N 15/52* | (2006.01) |
| *A23L 27/30* | (2016.01) |
| *C12N 15/81* | (2006.01) |
| *C12P 19/18* | (2006.01) |

(52) U.S. Cl.
CPC .............. *C12N 9/1051* (2013.01); *A23L 2/60* (2013.01); *A23L 27/36* (2016.08); *C12N 15/52* (2013.01); *C12N 15/81* (2013.01); *C12P 19/18* (2013.01); *C12P 19/56* (2013.01); *C12Y 204/01017* (2013.01); *A23V 2002/00* (2013.01)

(58) Field of Classification Search
CPC ...... C12N 15/81; C12N 15/52; C12N 9/1051; C12Y 204/01017; C12P 19/56; C12P 19/18; A23L 2/60; A23L 27/36; A23V 2002/00
See application file for complete search history.

(56) References Cited

U.S. PATENT DOCUMENTS

| | | | |
|---|---|---|---|
| 8,703,225 B2 | 4/2014 | Morita et al. | |
| 9,243,273 B2 | 1/2016 | Markosyan et al. | |
| 9,562,251 B2 | 2/2017 | Kishore et al. | |
| 9,631,215 B2 | 4/2017 | Houghton-Larsen et al. | |
| 9,752,174 B2* | 9/2017 | Markosyan | A23L 27/33 |
| 9,848,632 B2 | 12/2017 | Morita et al. | |
| 9,957,540 B2 | 5/2018 | Mikkelsen et al. | |
| 10,000,783 B2* | 6/2018 | Ono | C07H 21/00 |
| 10,017,804 B2* | 7/2018 | Simon | C12P 15/00 |
| 10,113,154 B2 | 10/2018 | Ono | |
| 10,113,155 B2 | 10/2018 | Ono | |
| 10,364,450 B2 | 7/2019 | Olsson et al. | |
| 10,392,644 B2 | 8/2019 | Kishore et al. | |
| 10,420,360 B2 | 9/2019 | Morita et al. | |

(Continued)

FOREIGN PATENT DOCUMENTS

| | | |
|---|---|---|
| AU | 2013211605 B2 | 8/2017 |
| AU | 2016271628 B2 | 5/2020 |

(Continued)

OTHER PUBLICATIONS

Bennetzen et al., Reference genome sequence of the model plant Setaria. Nature Biotechnol., 2012, vol. 30(6): 555-561. (Year: 2012).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*

(Continued)

*Primary Examiner* — Ganapathirama Raghu
(74) *Attorney, Agent, or Firm* — Squire Patton Boggs (US) LLP

(57) ABSTRACT

Provided herein are compositions and methods for improved production of steviol glycosides in a host cell. In some embodiments, the host cell is genetically modified to comprise a heterologous nucleotide sequence encoding a *Setaria italica* UDP-glycosyltransferase 40087 or its variant UDP-glycosyltransferase. In some embodiments, the host cell is genetically modified to comprise a heterologous nucleotide sequence encoding a UDP-glycosyltransferase sr.UGT_9252778, Bd_uGT10850, and/or Ob_UGT91B_1 like. In some embodiments, the host cell further comprises one or more heterologous nucleotide sequence encoding further enzymes of a pathway capable of producing steviol glycosides in the host cell. The compositions and methods described herein provide an efficient route for the heterologous production of steviol glycosides, including but not limited to, rebaudioside D and rebaudioside M.

39 Claims, 23 Drawing Sheets

Specification includes a Sequence Listing.

(56) References Cited

U.S. PATENT DOCUMENTS

| | | |
|---|---|---|
| 10,421,983 B2 | 9/2019 | Douchin et al. |
| 10,442,831 B2 | 10/2019 | Mao et al. |
| 10,450,338 B2 | 10/2019 | Mao et al. |
| 10,472,660 B2 | 11/2019 | Park et al. |
| 10,485,257 B2 | 11/2019 | Markosyan et al. |
| 10,499,661 B2 | 12/2019 | Purkayastha et al. |
| 10,612,065 B2 | 4/2020 | Anderson et al. |
| 10,774,103 B2 | 9/2020 | Mao et al. |
| 10,800,803 B2 | 10/2020 | Mao et al. |
| 10,815,513 B2 | 10/2020 | Anderson et al. |
| 10,815,514 B2 | 10/2020 | Olsson et al. |
| 10,888,099 B2 | 1/2021 | Purkayastha et al. |
| 2018/0371003 A1 | 12/2018 | Geertman et al. |
| 2018/0371516 A1 | 12/2018 | Geertman et al. |
| 2018/0371517 A1 | 12/2018 | Simon et al. |
| 2019/0062796 A1 | 2/2019 | Dyekjaer et al. |
| 2019/0144907 A1 | 5/2019 | Hansen et al. |
| 2019/0194240 A1 | 6/2019 | Galaev et al. |
| 2019/0203245 A1 | 7/2019 | Douchin et al. |
| 2019/0270971 A1 | 9/2019 | Donald et al. |
| 2020/0017896 A1 | 1/2020 | Olsson et al. |
| 2020/0024630 A1 | 1/2020 | Douchin et al. |
| 2020/0032227 A1 | 1/2020 | Vroom et al. |
| 2020/0080123 A1 | 3/2020 | Heal et al. |
| 2020/0123583 A1 | 4/2020 | Houghton-Larsen et al. |
| 2020/0157594 A1 | 5/2020 | Markosyan et al. |
| 2020/0165651 A1* | 5/2020 | Wichmann ............... C12P 7/40 |
| 2020/0221746 A1 | 7/2020 | Markosyan et al. |
| 2020/0283814 A1 | 9/2020 | Anderson et al. |
| 2020/0283815 A1 | 9/2020 | Boer et al. |
| 2020/0283816 A1 | 9/2020 | Boer et al. |
| 2020/0308617 A1 | 10/2020 | Mikkelsen et al. |
| 2020/0347425 A1 | 11/2020 | Philippe et al. |
| 2021/0009968 A1 | 1/2021 | Donald et al. |
| 2021/0037864 A1 | 2/2021 | Morita et al. |

FOREIGN PATENT DOCUMENTS

| | | |
|---|---|---|
| AU | 2019264515 B2 | 3/2021 |
| CN | 104 726 523 A | 6/2015 |
| EP | 2954058 B1 | 10/2014 |
| EP | 2 826 861 A1 | 1/2015 |
| EP | 2350110 B1 | 6/2016 |
| EP | 2742142 B2 | 6/2016 |
| EP | 3101023 A1 | 7/2016 |
| EP | 2963122 B1 | 5/2018 |
| EP | 2498625 B1 | 10/2018 |
| EP | 2806754 B1 | 10/2018 |
| EP | 2862927 B1 | 10/2018 |
| EP | 3004366 B1 | 2/2019 |
| EP | 3461342 A1 | 4/2019 |
| EP | 3502264 A2 | 6/2019 |
| EP | 2575432 B1 | 8/2019 |
| EP | 3593633 A1 | 1/2020 |
| EP | 2832858 B1 | 7/2020 |
| EP | 3683315 A1 | 7/2020 |
| EP | 3009508 B1 | 11/2020 |
| WO | WO 2013/022989 A2 | 2/2013 |
| WO | WO 2013176738 A1 | 11/2013 |
| WO | WO 2014/122227 A2 | 8/2014 |
| WO | WO 2014122328 A1 | 8/2014 |
| WO | WO 2014/193888 A1 | 12/2014 |
| WO | WO 2015007748 A1 | 1/2015 |
| WO | WO 2016/023844 A1 | 2/2016 |
| WO | WO 2016023844 A1 | 2/2016 |
| WO | WO 2016/038095 A2 | 3/2016 |
| WO | WO 2016120486 A1 | 8/2016 |
| WO | WO 2016/196321 A1 | 12/2016 |
| WO | WO 2016196345 A1 | 12/2016 |
| WO | WO 2017009293 A1 | 1/2017 |
| WO | WO 2017009294 A1 | 1/2017 |
| WO | WO 2017025649 A1 | 2/2017 |
| WO | WO 2017098017 A1 | 6/2017 |
| WO | WO 2017178632 A1 | 10/2017 |
| WO | WO 2017198681 A1 | 11/2017 |
| WO | WO 2017198682 A1 | 11/2017 |
| WO | WO 2018029272 A1 | 2/2018 |
| WO | WO 2018083338 A1 | 5/2018 |
| WO | WO 2018213279 A1 | 11/2018 |
| WO | WO 19193356 A1 | 10/2019 |
| WO | WO 19211230 A1 | 11/2019 |

OTHER PUBLICATIONS

Whisstocket al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guo et al., Protein tolerance to random amino acid change. PNAS., 2004, vol. 101 (25): 9205-9210. (Year: 2004).*
International Search report and written opinion dated Feb. 8, 2018 for PCT/US2017/046637, 29 pages.
Ceunen et al., "Steviol Glycosides: Chemical Diversity, Metabolism, and Function", J. Nat. Prod., 2013, vol. 76, No. 6, pp. 1201-1228.
Database RefSeq [Online] Nov. 30, 2015, "UDP-glycosyltransferase 91A1 [Setaria italica]", XP002775106, 1 page.
Griggs & Johnston, "Regulatedexpressionof the GAL4 activator gene in yeast provides asensitive genetic switch for glucose repression", Proc. Natl. Acad. Sci. USA, Oct. 1991, vol. 88, pp. 8597-8601.
Ohta et al., "Characterization of Novel Steviol Glycosides from Leaves of *Stevia rebaudiana* Morita", 2010, J. Appl. Glycosci., 57, pp. 199-209.
Prakash et al., "Development of Next Generation Stevia Sweetener: Rebaudioside M", Foods, vol. 3, No. 1, Feb. 27, 2014, pp. 162-175.
GenBank: AAQ63464.1, Jun. 21, 2006; 2 pages.
GenBank: AAR06912.1, Dec. 28, 2004; 1page.
GenBank: AAR06916.1, Dec. 28, 2004; 2 pages.
GenBank: AAR06920.1, Dec. 28, 2004; 2 pages.
GenBank: ABC47946.1, Apr. 13, 2006; 2 pages.
GenBank: ACE87855.1, Jun. 24, 2008; 2 pages.
GenBank: ADB55711.1, Mar. 9, 2010; 2 pages.
GenBank: AFC92798.1, Dec. 21, 2012; 2 pages.
GenBank: BAJ94055.1, May 20, 2011; 2 pages.
NCBI Reference Sequence: XP_003560669.1, Mar. 27, 2018; 2 pages.
NCBI Reference Sequence: XP_004250485.1, Aug. 8, 2018; 2 pages.
NCBI Reference Sequence: XP_004982059.1, Oct. 13, 2017; 2 pages.
NCBI Reference Sequence: XP_006650455.1, Mar. 4, 2016; 2 pages.
NCBI Reference Sequence: XP_010230871.1, Mar. 27, 2018; 2 pages.
NCBI Reference Sequence: XP_015629141.1, Aug. 7, 2018; 2 pages.
UniProtKB/Swiss-Prot: Q5MQ85.1, May 5, 2009; 3 pages.
UniProtKB, Primary accession No. K4AME6, Nov. 28, 2012; 3 pages.

* cited by examiner

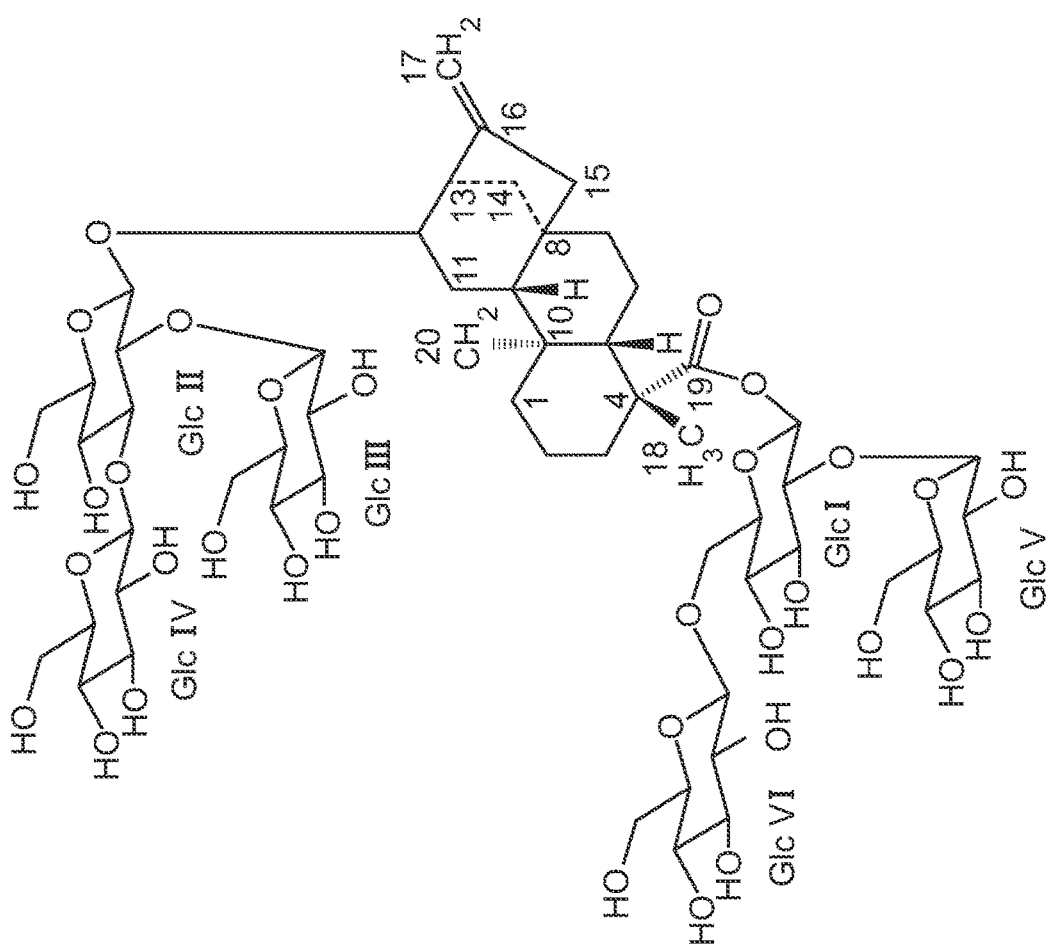
FIG. 1B Reb M2

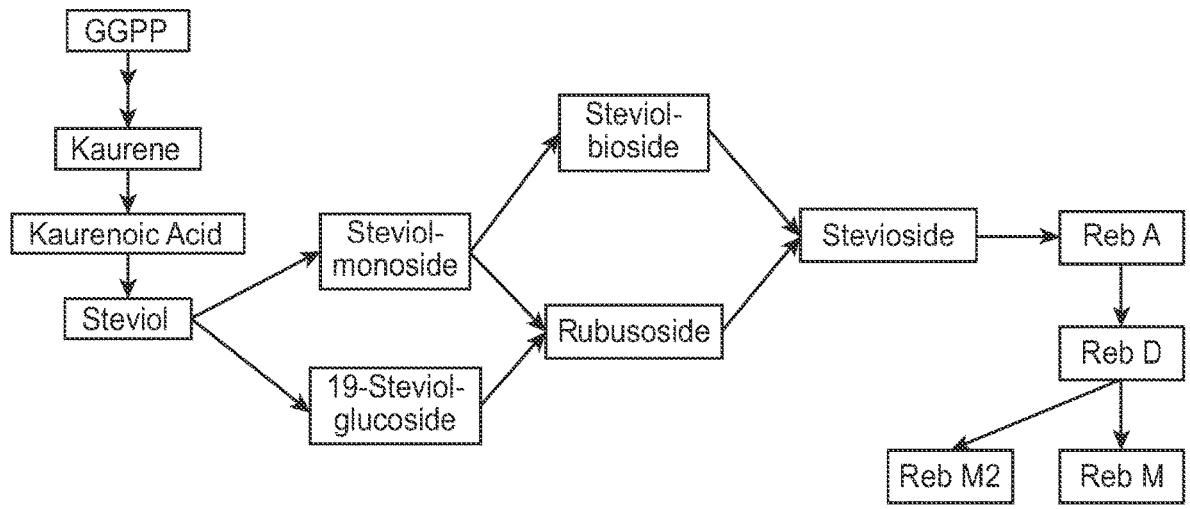
FIG. 2C
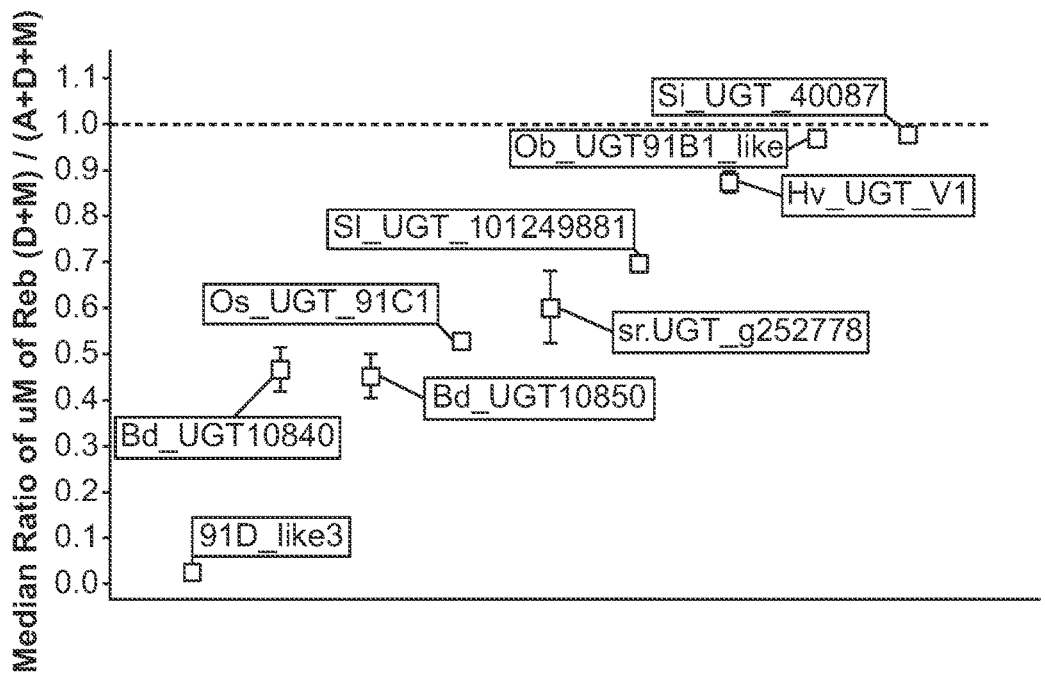
FIG. 3
| Down Stream ALG1 ORF | PGAL1 | F-Cph1 cut sequence | terminator | Down Stream ALG1 ORF |
FIG. 4

| UGT40087 | IPYG$_{214}$ | $_{215}$LVPP | UGT40087 |
| --- | --- | --- | --- |
| Si91Dlike | IQYG$_{215}$ | $_{216}$LVPP | Si91Dlike |
| Os_UGT_91C1 | TFLG$_{246}$ | $_{247}$LMPP | Os_UGT_91C1 |
| 91Dlike3 | VPVG$_{260}$ | $_{261}$LLPP | 91Dlike3 |
| UGT40087 | IPYG$_{214}$ | $_{216}$LVPP | Si91Dlike |
| UGT40087 | IPYG$_{214}$ | $_{247}$LMPP | Os_UGT_91C1 |
| UGT40087 | IPYG$_{214}$ | $_{261}$LLPP | 91Dlike3 |

FIG. 8

UDP-DEPENDENT GLYCOSYLTRANSFERASE FOR HIGH EFFICIENCY PRODUCTION OF REBAUDIOSIDES

1. CROSS-REFERENCE TO RELATED APPLICATIONS

The present application is a U. S. National Phase application under 35 U.S.C. § 371 of international application No. PCT/US2017/046637, filed Aug. 11, 2017, which claims the benefit of U.S. Provisional Application No. 62/374,408, filed Aug. 12, 2016, the contents of which are i hereby incorporated by reference in its entirety their entireties.

This application includes an electronically submitted sequence listing in .txt format. The .txt file contains a sequence listing entitled "107345_00714_ST25.txt" created on Apr. 13, 2021 and is 76 KB in size. The sequence listing contained in this .txt file is part of the specification and is hereby incorporated by reference herein in its entirety.

2. FIELD OF THE INVENTION

The present disclosure relates to certain uridine diphosphate-dependent glycosyltransferases (UGTs), compositions comprising the same, host cells comprising the same, and methods of their use for the production of rebaudiosides including rebaudioside D and rebaudioside M.

3. BACKGROUND

Zero-calorie sweeteners derived from natural sources are desired to limit the ill-effects of high-sugar consumption (e.g., diabetes and obesity). Rebaudioside M (RebM), is one of many sweet-tasting compounds produced by the stevia plant (*Stevia rebaudiana* Bertoni). Of all the rebaudiosides, RebM has the highest potency (about 200-300 times sweeter than sucrose) and is the cleanest tasting. However, RebM is only produced in minor quantities by the Stevia plant, and is only a small fraction of the total steviol glycoside content (<1.0%). Ohta et al., 2010, *J. Appl. Glycosci.*, 57, 199-209 (2010). As such it is desirable to produce RebM using biotechnological routes allowing production in large quantities and at high purity.

To economically produce a product using biotechnology, each step in the bioconversion from feedstock to product advantageously has a high conversion efficiency (ideally>90%). In engineering of yeast to produce RebM, a limitation was identified in the penultimate biosynthetic step, namely the conversion of Rebaudioside A (RebA) to Rebaudioside D (RebD) See FIG. 1A. The native enzyme (Ono, EP 2 826 861 A1, UGT91D_like3, or a near homologue) was observed to convert about 3% of RebA to RebD. Two other UGT enzymes have been identified that are capable of converting RebA to RebD. One is Os_UGT_91C1 from *Oryza sativa* (also referred to as EUGT11 in Houghton-Larsen et al., WO 2013/022989 A2), and the other is Sl_UGT_101249881 from *Solanum lycopersicum* (also referred to as UGTSL2 in Markosyan et al., WO2014/193888 A1). However, both Os_UGT_91C1 and Sl_UGT_101249881 were initially observed by the present inventors to have lower than desired conversion efficiencies of about 53% and 70%, respectively. All three of these enzymes, UGT91D_like3, Os_UGT_91C1, and Sl_UGT_101249881, are uridine diphosphate-dependent glycosyltransferases (UGT) which transfer a glucose moiety to the C-2' position of the 19-O-glucose residue via formation of a beta(1->2) linkage (FIG. 1A).

To produce RebM efficiently and at high purity, improved enzymes capable of converting RebA to RebD at high efficiency are needed. The compositions and methods provided herein address this need and provide related advantages as well.

4. SUMMARY OF THE INVENTION

Provided herein are compositions and methods for the improved conversion of RebA to RebD and for the improved production of RebD and/or RebM. These compositions and methods are based in part on the surprising discovery of certain uridine diphosphate-dependent glycosyltransferases (UGTs) are capable of converting RebA to RebD with remarkably high efficiency. Even a modest improvement in strain performance (e.g., ten percent) with new UGTs can potentially save over ten million dollars in production cost in the future, assuming that the market demand for RebM is 5000 million tons per year.

Certain UGTs described herein are also capable of producing RebM with little or no non-natural glycosides such as RebM2 side product (i.e., an isomer of RebM). See Ceunen S. et al. Steviol Glycosides: Chemical Diversity, Metabolism, and Function. *J. Nat. Prod.*, 76, 1201-1228 (2013) for a list of currently-known Stevia glycosides. As such, in certain embodiments, the compositions and methods described herein can reduce the costs of downstream processing to obtain a composition with high purity RebM.

Also provided herein are compositions and methods for alternative enzymes which are capable of producing steviol glycosides with different substrate specificities than previously known UGTs. The new alternative enzymes can potentially produce different mixtures or proportions of steviol glycosides compared to those produced by other known enzymes. Compositions with different mixtures or proportions of steviol glycosides can potentially impart alternative, sweet taste profiles, which may be useful in formulating various consumable or food products.

Thus, provided herein are genetically modified host cells and methods of their use for the production of industrially useful compounds. In one aspect, provided herein is a genetically modified host cell comprising: a heterologous nucleic acid encoding a UDP-glycosyltransferase (UGT40087, also refer to as Si_UGT_40087). In some embodiments, the genetically modified host cell further comprises one or more enzymatic pathways capable of producing steviol and/or steviol glycosides.

In certain embodiments, provided herein are genetically modified host cells comprising a heterologous nucleic acid encoding a UDP-glycosyltransferase comprising an amino acid sequence having at least 80%, 85%, 90%, or 95% sequence identity to the sequence of UGT40087 (e.g., SEQ ID NO:1 or SEQ ID NO:11). In certain embodiments, the genetically modified host cell is capable of converting RebA to RebD at an efficiency greater than 90%, 95%, 96%, or 97%. In certain embodiments, the genetically modified host cell comprises a UDP-glycosyltransferase comprising a sugar acceptor domain, wherein the amino acid sequence of the sugar acceptor domain has at least 84%, 85%, 86%, 87%, 88%, 89%, 90%, 91%, 92%, 93%, 94%, 95%, 96%, 97%, 98%, or 99% sequence identity to the amino acid sequence of the sugar acceptor domain of SEQ ID NO:1 or SEQ ID NO:11. In certain embodiments, the genetically modified host cell comprises a UDP-glycosyltransferase which comprises a loop1 amino acid sequence, a variant loop1 amino acid sequence, a loop2 amino acid sequence, a variant loop2 amino acid sequence, a loop3_1 amino acid sequence, a variant loop3_1 amino acid sequence, a loop3_2 amino acid sequence, a variant loop3_2 amino acid sequence, a loop4_1 amino acid sequence, a variant loop4_1 amino acid sequence, a loop4_2 amino acid sequence, or any combination thereof. In certain embodiments, the genetically modified host cell comprises a UDP-glycosyltransferase comprising an amino acid sequence having at least 61%, 65%, 70%, 75%, 80%, 85%, 90%, or 95% sequence identity to the sugar acceptor domain of SEQ ID NO:1 or SEQ ID NO:11, and further comprises the loop4_1 amino acid sequence of SEQ ID NO:1 or SEQ ID NO:11.

In certain embodiments, provided herein are genetically modified host cells comprising a heterologous nucleic acid encoding a UDP-glycosyltransferase comprising an amino acid sequence having at least 80%, 85%, 90%, or 95% sequence identity to the sequence of SEQ ID NO:2, 5, or 6. In certain embodiments, the genetically modified host cell is capable of converting RebA to RebD at an efficiency greater than 60%, 65%, 70%, 75%, 80%, 85%, 90%, 95%, 96%, or 97%. In certain embodiments, the genetically modified host cell comprises a UDP-glycosyltransferase comprising a sugar acceptor domain, wherein the amino acid sequence of the sugar acceptor domain has at least 84%, 85%, 86%, 87%, 88%, 89%, 90%, 91%, 92%, 93%, 94%, 95%, 96%, 97%, 98%, or 99% sequence identity to the amino acid sequence of the sugar acceptor domain of SEQ ID NO:2, 5, or 6. In certain embodiments, the genetically modified host cell comprises a UDP-glycosyltransferase which comprises a loop1 amino acid sequence, a variant loop1 amino acid sequence, a loop2 amino acid sequence, a variant loop2 amino acid sequence, a loop3_1 amino acid sequence, a variant loop3_1 amino acid sequence, a loop3_2 amino acid sequence, a variant loop3_2 amino acid sequence, a loop4_1 amino acid sequence, a variant loop4_1 amino acid sequence, a loop4_2 amino acid sequence, or any combination thereof. In certain embodiments, the genetically modified host cell comprises a UDP-glycosyltransferase comprising an amino acid sequence having at least 61%, 65%, 70%, 75%, 80%, 85%, 90%, or 95% sequence identity to the sugar acceptor domain of SEQ ID NO:2, 5, or 6, and further comprises the loop4_1 amino acid sequence of SEQ ID NO:2, 5, or 6.

In another aspect, provided herein are methods for producing a heterologous steviol glycoside, the method comprising: culturing a population of genetically modified host cells provided herein, capable of producing the steviol glycoside as described herein, in a medium with a carbon source under conditions suitable for making said steviol glycoside compound; and recovering said steviol glycoside from the medium. In some embodiments, the heterologous steviol glycoside is selected from the group consisting of RebD and RebM.

In another aspect, provided herein is a method for increasing the production of a steviol glycoside compound in a host cell, the method comprising: expressing in the host cell a heterologous nucleic acid encoding a UGT40087; and culturing the host cell under conditions suitable for producing the steviol glycoside. In some embodiments, the host cell does not comprise a UGT91D_like3 enzyme, a Os_UGT_91C1 enzyme, or a Sl_UGT_101249881 enzyme.

In another aspect, provided herein are methods for producing RebD, the method comprising: culturing a population of genetically modified host cells provided herein, capable of producing RebD as described herein, in a medium with a carbon source under conditions suitable for making said RebD; and recovering said RebD from the medium.

In another aspect, provided herein are methods for producing RebM, the method comprising: culturing a population of genetically modified host cells provided herein, capable of producing RebM as described herein, in a medium with a carbon source under conditions suitable for making said RebM; and recovering said RebM from the medium.

In another aspect, provided herein are methods for producing RebD, the method comprising: contacting RebA with glucose and a UDP-glycosyltransferase described herein, capable of converting RebA to RebD, under conditions suitable for forming RebD.

In another aspect, provided herein are methods for producing RebM, the method comprising: contacting RebA with glucose and a UDP-glycosyltransferase described herein, capable of converting RebA to RebD, under conditions suitable for forming RebD, and with a UDP-glycosyltransferase described herein, capable of converting RebD to RebM.

In some embodiments, the host cell is a yeast cell. In some embodiments, the yeast is *Saccharomyces cerevisiae*. In some embodiments, the host cell produces RebD or RebM at high efficiency. In some embodiments, the host cell produces an increased amount of RebD or RebM compared to a yeast cell not comprising the UGT40087 enzyme. In some embodiments, the host cell produces an increased amount of RebM relative to RebM2 compared to a yeast cell not comprising the UGT40087 enzyme.

In another aspect, other UDG-glycosyltransferases provided herein can be used in addition or in alternative to UGT40087. These include, for example, sr.UGT_9252778, Bd_UGT10840, Hv_UGT_V1, Bd_UGT10850, and Ob_UGT91B1_like.

5. BRIEF DESCRIPTION OF THE FIGURES

FIG. 1A provides a schematic representation of the conversion of RebA to RebD to RebM.

FIG. 1B provides the structure of RebM2.

FIG. 1C provides a schematic diagram of the mevalonate pathway.

FIG. 2A provides an exemplary pathway of farnesyl pyrophosphate (FPP) to steviol.

FIG. 2B provides an exemplary pathway of steviol to RebM.

FIG. 2C provides an exemplary pathway for the enzymatic production of RebM.

FIG. 3 provides the ratio of RebA to RebD conversion in vivo, as measured by micromoles of Reb (D+M)/micromoles of Reb (A+D+M). The parent control strain is labelled 91D_like3 (from *Stevia rebaudiana*; this strain contains UGT's: 85C2, 74G1, 91D_like3, and 76G1 only, in addition to an empty landing pad. It is noted that 91D_like3 has very low RebA to RebD conversion (~3% see Table 5). A single copy of each UGT enzyme was inserted into the parent control strain and screened for improved RebA to RebD conversion. Six UGT enzymes are shown to have RebA to RebD conversion that are at least equivalent to, or better than, the previous known enzymes Os_UGT_91C1 and Sl_UGT_101249881. Three UGT enzymes (Sl_UGT_40087, Ob_UGT91B1_like, and Hv_UGT_V1 are better than both previously identified UGT enzymes at converting RebA to RebD. Error bars are standard error.

FIG. 4 provides a schematic diagram of "landing pad" design used to insert individual UGT enzymes for screening for RebA to RebD conversion in yeast.

FIGS. 5a-h illustrate chromatograms of RebA, RebD, RebM, RebM2 produced in vivo for each UGT gene used to generate data described in Table 5 and FIG. 3. The chromatogram peaks are selected to show peaks associated with RebA, RebD, RebM, and RebM2. Each figure shows the retention time versus % intensity for authentic standards, the control parent strain Y31062, and Y31062 with an additional UGT enzyme. Y31062 is the parent control strain and contains UGT74G1, UGT85C2, UGT91D_like3, and UGT76G1 with an empty landing pad. FIG. 5a: data for Si_UGT_40087; this figure also includes a chromatogram for a RebE authentic standard. FIG. 5b: data for Ob_UGT91B1_like. FIG. 5c: data for Hv_UGT_V1. FIG. 5d: data for Sl_UGT_101249881. FIG. FIG. 5e: data for UGT_g252778. FIG. 5f: data for Os_UGT_91C1. FIG. 5g: data for Bd_UGT10850. FIG. 5h: data for Bd_UGT10840. FIG. 5i shows a magnified view the chromatogram for just the RebE peak of Si_UGT_40087 versus the authentic standard to confirm that this peak is RebE.

Figure 8:
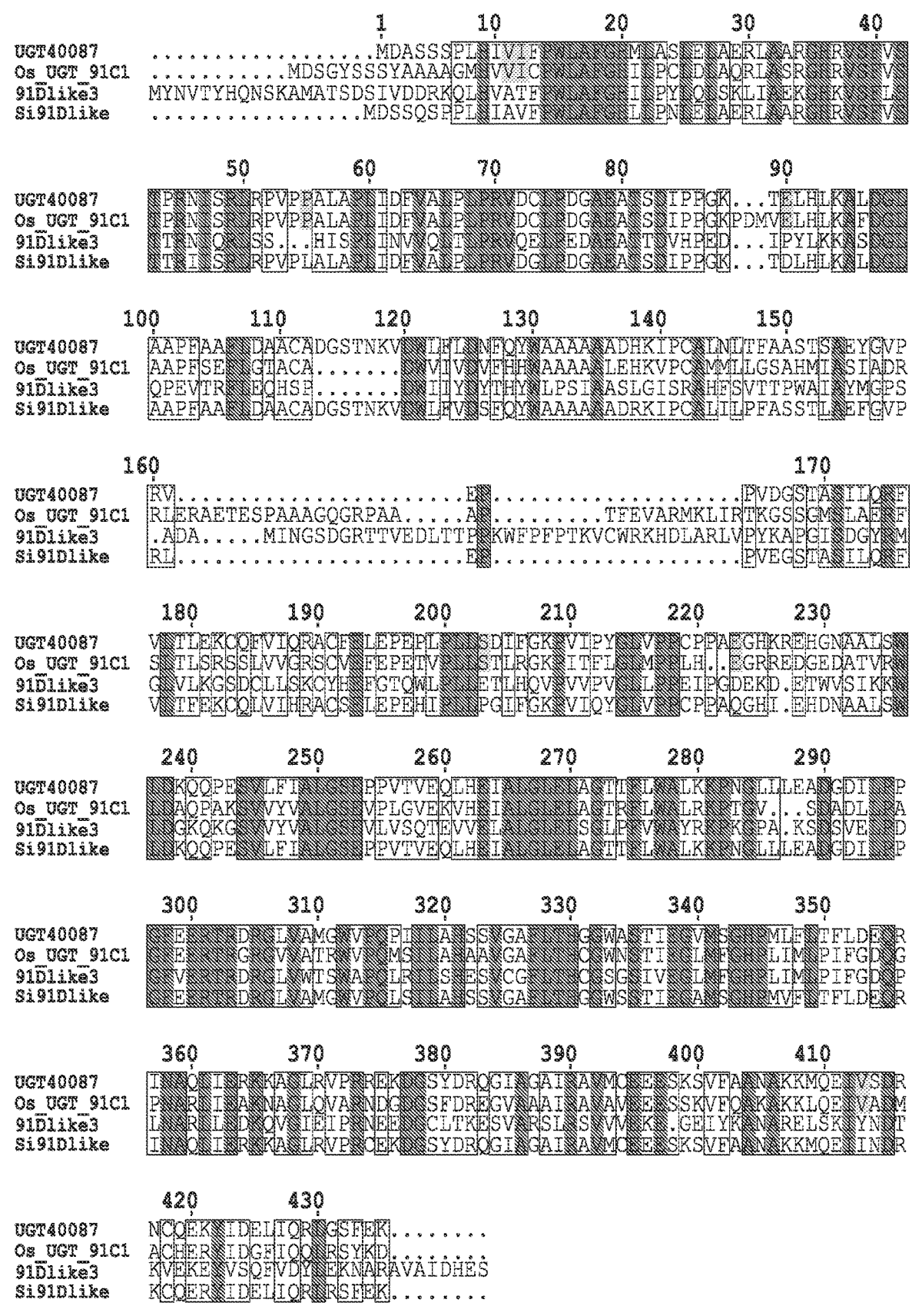

FIG. 8 illustrates sequence alignment of four UDP-glycosyltransferases (UGT40087 (SEQ ID NO: 1); Os_UGT_91C1 (SEQ ID NO: 8); 91Dlike3 (SEQ ID NO: 7); Si91Dlike (SEQ ID NO: 12)).

Figure 9A:
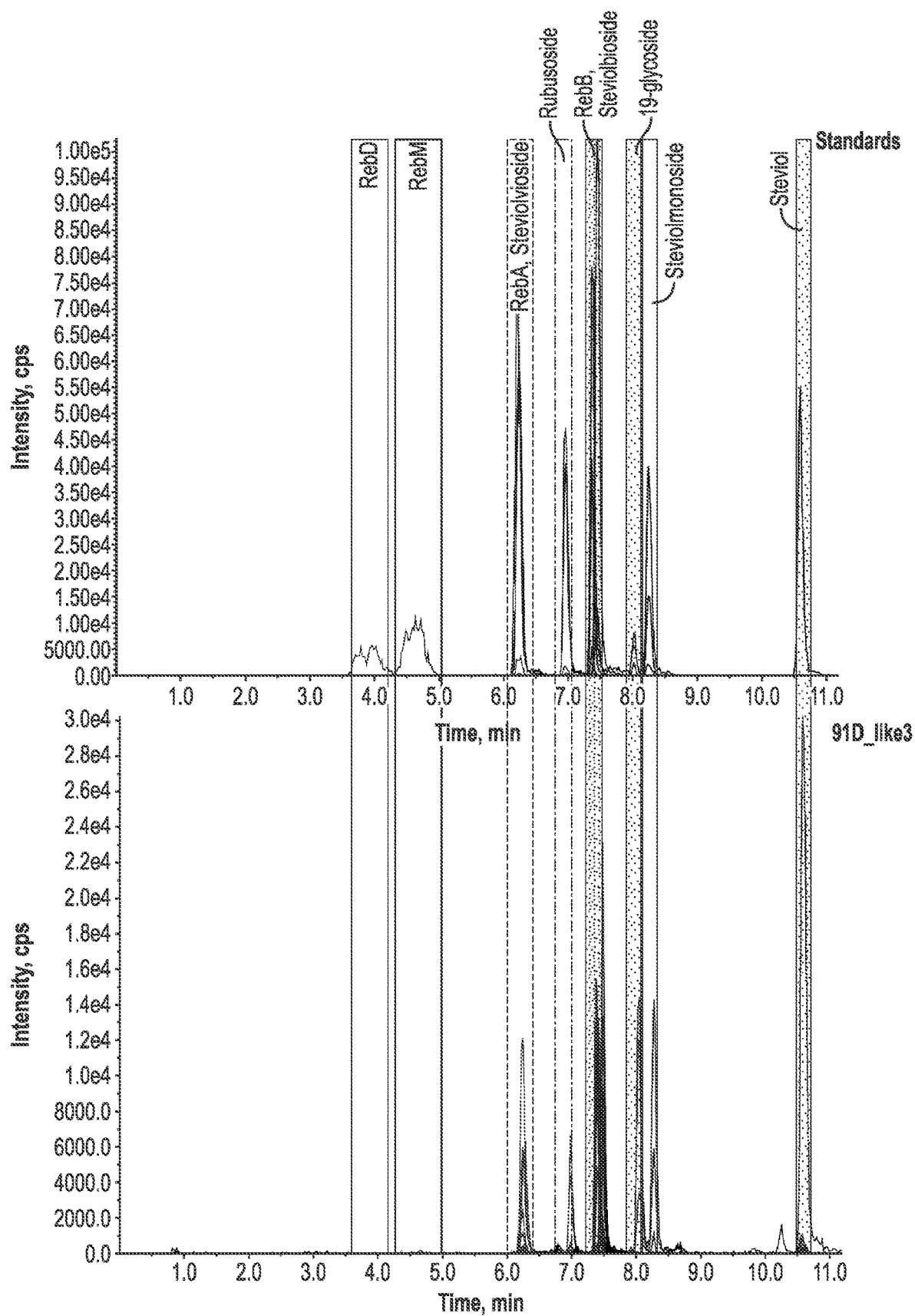
Figure 9B:
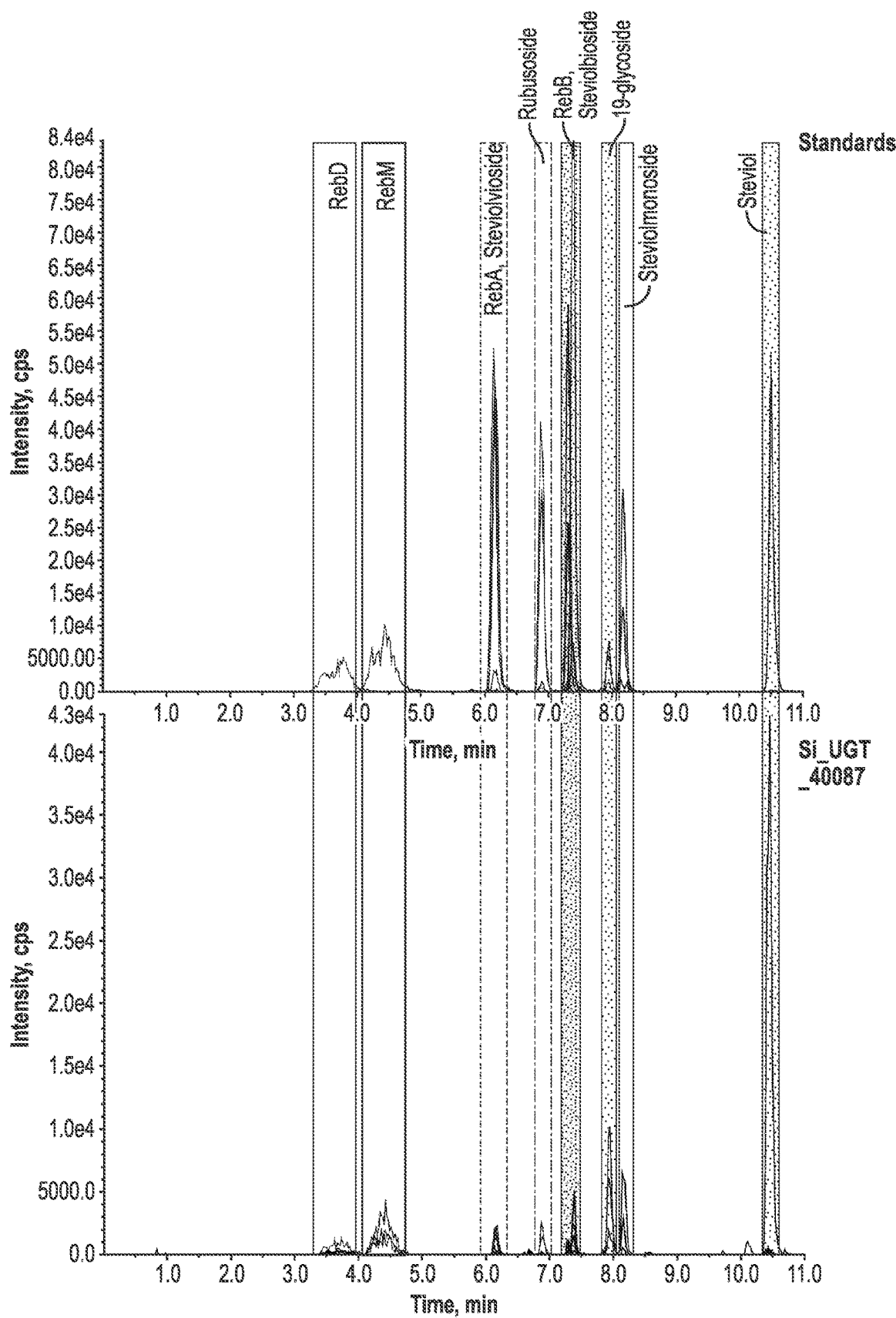
Figure 9C:
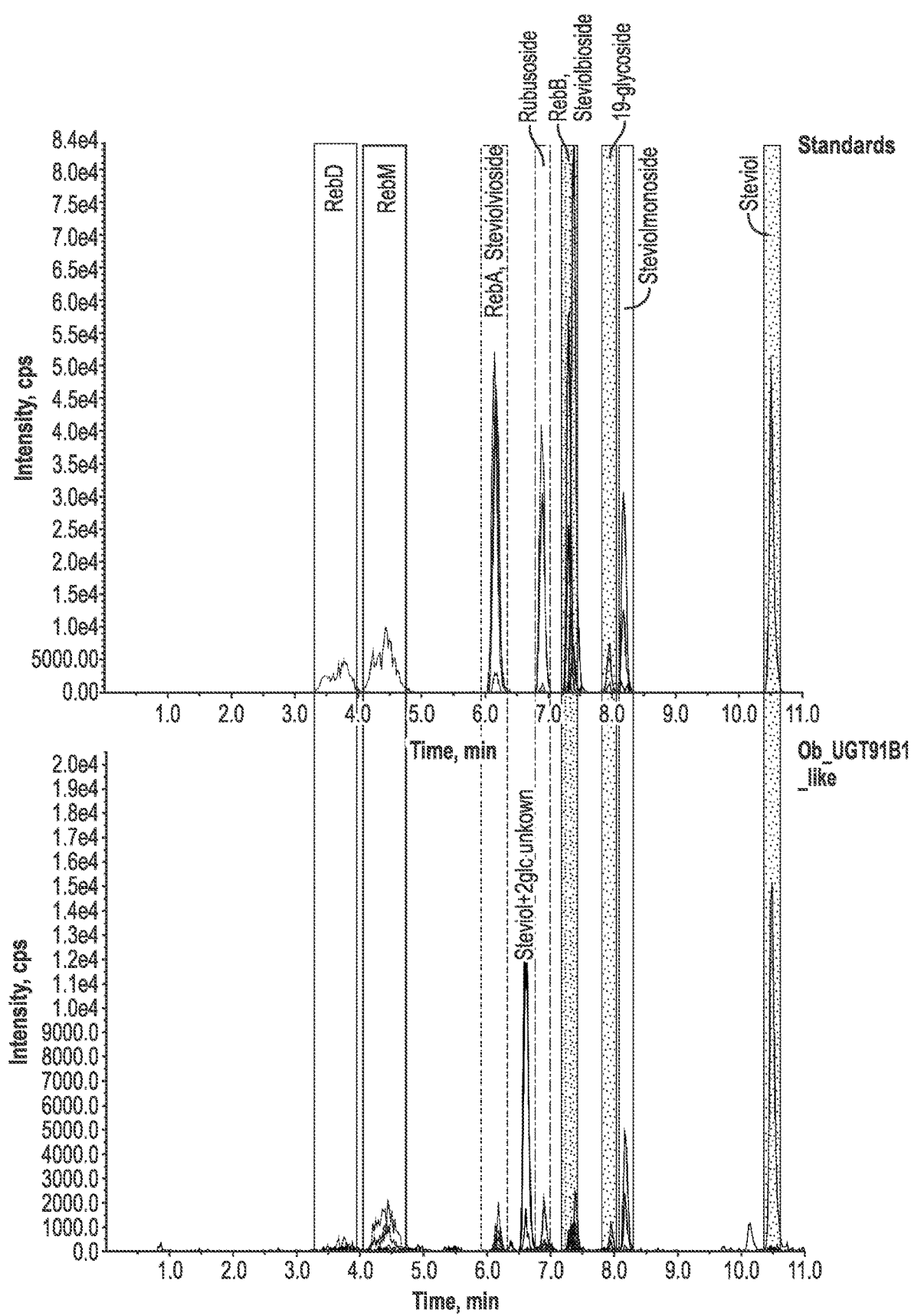

FIG. 9a illustrate a chromatogram of steviol glycosides produced in vivo for the parent control cell (comprising UGT74G1, UT85C2, UGT76G1, and UGT91D_like3). FIG. 9b illustrates a chromatogram of steviol glycosides produced in vivo for the parent control strain with UGT40087. FIG. 9c illustrates a chromatogram of steviol glycosides produced in vivo for the parent control strain with Ob_UGT91B1_like.

6. DETAILED DESCRIPTION OF THE EMBODIMENTS

6.1 Terminology

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, the term "parent cell" refers to a cell that has an identical genetic background as a genetically modified host cell disclosed herein except that it does not comprise one or more particular genetic modifications engineered into the modified host cell, for example, one or more modifications selected from the group consisting of: heterologous expression of an enzyme of a steviol pathway, heterologous expression of an enzyme of a steviol glycoside pathway, heterologous expression of a geranylgeranyl diphosphate synthase, heterologous expression of a copalyl diphosphate synthase, heterologous expression of a kaurene synthase, heterologous expression of a kaurene oxidase, heterologous expression of a steviol synthase (kaurenoic acid hydroxylase), heterologous expression of a cytochrome P450 reductase, heterologous expression of a UGT74G1, heterologous expression of a UGT76G1, heterologous expression of a UGT85C2, heterologous expression of a UGT91D, and heterologous expression of a UGT40087.

As used herein, the term "naturally occurring" refers to what is found in nature. For example, a UDP-glycosyltransferase that is present in an organism that can be isolated from a source in nature and that has not been intentionally modified by a human in the laboratory is naturally occurring UDP-glycosyltransferase. Conversely, as used herein, the term "non-naturally occurring" refers to what is not found in nature but is created by human intervention.

The term "medium" refers to a culture medium and/or fermentation medium.

The term "fermentation composition" refers to a composition which comprises genetically modified host cells and products or metabolites produced by the genetically modified host cells. An example of a fermentation composition is a whole cell broth, which can be the entire contents of a vessel (e.g., a flasks, plate, or fermenter), including cells, aqueous phase, and compounds produced from the genetically modified host cells.

As used herein, the term "production" generally refers to an amount of steviol or steviol glycoside produced by a genetically modified host cell provided herein. In some embodiments, production is expressed as a yield of steviol or steviol glycoside by the host cell. In other embodiments, production is expressed as a productivity of the host cell in producing the steviol or steviol glycoside.

As used herein, the term "productivity" refers to production of a steviol or steviol glycoside by a host cell, expressed as the amount of steviol or steviol glycoside produced (by weight) per amount of fermentation broth in which the host cell is cultured (by volume) over time (per hour).

As used herein, the term "yield" refers to production of a steviol or steviol glycoside by a host cell, expressed as the amount of steviol or steviol glycoside produced per amount of carbon source consumed by the host cell, by weight.

As used herein, the term "an undetectable level" of a compound (e.g., RebM2, steviol glycosides, or other compounds) means a level of a compound that is too low to be measured and/or analyzed by a standard technique for measuring the compound. For instance, the term includes the level of a compound that is not detectable by the analytical methods described in Example 7.

As used herein, the term "steviol glycoside(s)" refers to a steviol enzymatically altered by the addition of one or more sugar moieties, such as a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside D, rebaudioside N, rebaudioside O, synthetic steviol glycosides, e.g. enzymatically glucosylated steviol glycosides and combinations thereof.

As used herein, the term "uridine diphosphate (UDP)-glycosyltransferase" or "UDP-dependent glycosyltransferase" refers to an enzyme that has an activity of transferring a monosaccharide moiety from a glycosyl donor to a glycosyl acceptor, in particular, an enzyme that utilizes a UDP-sugar as a glycosyl donor. The term "UDP-glycosyltransferase" may be used interchangeably with "UGT".

As used herein, the term "a functional domain" means either "a sugar acceptor domain" or "a sugar donor domain" of a UDP-glycosyltransferase. Plant UDP-glycosyltransferase (UGTs) belong to Family 1 of glycosyltransferase superfamily. They adopt the GT-B structural fold. This shared structural feature by UGTs consists of two domains, a C-terminal and an N-terminal domain with similar Rossmann-like folds, separated by an inter-domain linker. The C-terminal domain binds UDP-glucose ("the sugar donor") and is thus also termed as the sugar donor domain, while the N-terminal domain binds the non-sugar substrate ("the acceptor") and is thus also termed as the acceptor domain.

As used herein, the term "variant" refers to a polypeptide differing from a specifically recited "reference" polypeptide (e.g., a wild-type sequence) by amino acid insertions, deletions, mutations, and/or substitutions, but retains an activity that is substantially similar to the reference polypeptide. For example, a variant UGT40087 retains an activity that is substantially similar to the reference UGT40087 having SEQ ID NO:11 in that a variant UGT40087 is also capable of catalyzing a reaction to convert RebA to RebD and/or stevioside to RebE. In some embodiments, the variant is created by recombinant DNA techniques, such as mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "variant loop1" amino acid sequence refers to an amino acid sequence which differs from the reference loop1 amino acid sequence of SEQ ID NO:1 or SEQ ID NO:11 (or a modified loop1 sequence of UGT40087 having the sequence of SEQ ID NO:28) by, one, two, three, four, five, six, seven, eight, nine, or ten amino acid insertions, deletions, mutations, and/or substitutions, but allows a UDP-glycosyltransferase comprising a variant loop1 amino acid sequence, inserted at a location which corresponds to the loop1 amino acid sequence location of SEQ ID NO:1 or SEQ ID NO:11, respectively, to catalyze conversion of RebA to RebD and/or stevioside to RebE.

As used herein, the term "variant loop2" amino acid sequence refers to an amino acid sequence which differs from the reference loop2 amino acid sequence of SEQ ID NO:1 or SEQ ID NO:11 by one, two, three, four, five, six, seven, eight, nine, or ten amino acid insertions, deletions, mutations, and/or substitutions, but allows a UDP-glycosyltransferase comprising a variant loop2 amino acid sequence, inserted at a location which corresponds to the loop2 amino acid sequence location of SEQ ID NO:1 or SEQ ID NO:11, respectively, to catalyze conversion of RebA to RebD and/or stevioside to RebE.

As used herein, the term "variant loop3_1" amino acid sequence refers to an amino acid sequence which differs from the reference loop3_1 amino acid sequence of SEQ ID NO:1 or SEQ ID NO:11 by one, two, three, four, five, six, seven, eight, nine, or ten amino acid insertions, deletions, mutations, and/or substitutions, but allows a UDP-glycosyltransferase comprising a variant loop3_1 amino acid sequence, inserted at a location which corresponds to the loop3_1 amino acid sequence location of SEQ ID NO:1 or SEQ ID NO:11, to catalyze conversion of RebA to RebD and/or stevioside to RebE. As used herein, the term "variant loop3_2" amino acid sequence refers to an amino acid sequence which differs from the reference loop3_2 amino acid sequence of SEQ ID NO:1 or SEQ ID NO:11 by one, two, three, four, five, six, seven, eight, nine, or ten amino acid insertions, deletions, mutations, and/or substitutions, but allows a UDP-glycosyltransferase comprising a variant loop3_2 amino acid sequence, inserted at a location that corresponds to the loop3_2 amino acid sequence location of SEQ ID NO:1 or SEQ ID NO:11, respectively to catalyze conversion of RebA to RebD and/or stevioside to RebE. In certain embodiments, a variant loop3_2 amino acid sequence differs from the reference loop3_2 amino acid sequence by, one, two, three, four, five six, seven, eight, nine, ten, or up to thirty amino acid insertions, deletions, mutations, and/or substitutions.

As used herein, the term "variant loop4_1" amino acid sequence refers to an amino acid sequence which differs from the reference loop4_1 amino acid sequence of SEQ ID NO:1 or SEQ ID NO:11 by one, two, three, four, five, six, seven, eight, nine, ten, or up to 30 amino acid insertions, deletions, mutations, and/or substitutions, but allows a UDP-glycosyltransferase comprising a variant loop4_1 sequence, inserted at a location that corresponds to the loop4_1 amino acid location of SEQ ID NO:11, to catalyze conversion of RebA to RebD and/or stevioside to RebE. As used herein, the term "sequence identity" or "percent identity," in the context or two or more nucleic acid or protein sequences, refer to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.*, 22: 4673-4680), Clustal Omega (Sievers et al., (2011) *Molecular Systems Biology.*, 7:539), ALIGN (Myers et al., (1988) *CABIOS*, 4: 11-17), FASTA (Pearson et al., (1988) *PNAS*, 85:2444-2448; Pearson (1990), *Methods Enzymol.*, 183: 63-98) and gapped BLAST (Altschul et al., (1997) *Nucleic Acids Res.*, 25: 3389-3402) are useful for this purpose. The BLAST or BLAST 2.0 (Altschul et al., *J. Mol. Biol.* 215: 403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=2, Nucleic mismatch=−3, Expectation value=10.0, Word size=11, Max matches in a query range=0). In certain embodiments, for nucleotide sequence alignment and sequence identity calculations, the BLASTN program is used with these parameters (Gap opening penalty=5, Gap extension penalty=2, Nucleic match=1, Nucleic mismatch=−3, Expectation value=10.0, Word size=11). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0. Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. In the embodiments described herein, the sequence identity is calculated using BLASTN or BLASTP programs using their default parameters. In the embodiments described herein, the sequence alignment of two or more sequences are performed using Clustal Omega using the suggested default parameters (Dealign input sequences: no; Mbed-like clustering guide-tree: yes; Mbed-like clustering iteration: yes; number of combined iterations: default(0); Max guide tree iterations: default; Max HMM iterations: default; Order: aligned).

6.2 Host Cells

Provided herein are host cells capable of producing rebaudioside D (RebD) from rebaudioside A (RebA) at high efficiency. In certain embodiments, the host cells can produce RebD from RebA as a starting material. In preferred embodiments, the host cells can produce RebA from a carbon source in a culture medium and can further produce RebD from the RebA. In particular embodiments, the host cells can further produce rebaudioside M (RebM) from the RebD.

In particular embodiments, the host cells comprise the enzyme activity of uridine diphosphate glycosyltransferase 87 (UGT40087). A UGT40087 enzyme is capable of converting RebA to RebD at high efficiency. In certain embodiments, a UGT40087 enzyme is capable of converting RebA to RebD at an efficiency of greater than 80%. In certain embodiments, a UGT40087 enzyme is capable of converting RebA to RebD at an efficiency of greater than 85%. In certain embodiments, a UGT40087 enzyme is capable of converting RebA to RebD at an efficiency of greater than 90%. In certain embodiments, a UGT40087 enzyme is capable of converting RebA to RebD at an efficiency of greater than 95%. In certain embodiments, a UGT40087 enzyme is capable of converting RebA to RebD at an efficiency of greater than 96%. In certain embodiments, a UGT40087 enzyme is capable of converting RebA to RebD at an efficiency of about 97%. In certain embodiments, a UGT40087 enzyme is capable of converting stevioside to RebE.

In certain embodiments, the host cell is capable of converting RebA to RebD at an efficiency of greater than 80%. In certain embodiments, the host cell is capable of converting RebA to RebD at an efficiency of greater than 85%. In certain embodiments, the host cell is capable of converting RebA to RebD at an efficiency of greater than 90%. In certain embodiments, the host cell is capable of converting RebA to RebD at an efficiency of greater than 95%. In certain embodiments, the host cell is capable of converting RebA to RebD at an efficiency of greater than 96%. In certain embodiments, the host cell is capable of converting RebA to RebD at an efficiency of about 97%. In certain embodiments, the host cell is capable of converting stevioside to RebE.

Efficiency of conversion can be measured by any technique apparent to those of skill in the art. In certain embodiments, efficiency of conversion can be measured by contacting RebA with an enzyme or host cell under suitable conditions for forming RebD. Efficiency can be measured by comparing the molar amount of RebD produced compared to the total amount of RebA and RebD in the resulting composition. Efficiency can also be measured by comparing the total amount of RebD and downstream products of RebD to the total amount of RebA, RebD, and downstream products of RebD in the resulting composition. For instance, efficiency can also be measured by comparing the total amount of RebD, RebM, and RebM2 compared to the total amount of RebA, RebD, RebM, and RebM2 in the resulting composition.

In certain embodiments, provided herein are host cells comprising a UGT40087 comprising the amino acid sequence of SEQ ID NO:1 or SEQ ID NO:11. In certain embodiments, provided herein are host cells comprising a UDP-glycosyltransferase comprising an amino acid sequence substantially identical to the amino acid sequence of SEQ ID NO:1 or SEQ ID NO:11. In certain embodiments, provided herein are host cells comprising a UDP-glycosyltransferase comprising an amino acid sequence that is at least 60% identical to the amino acid sequence of SEQ ID NO:1 or SEQ ID NO:11. In certain embodiments, provided herein are host cells comprising a UDP-glycosyltransferase comprising an amino acid sequence that is at least 65% identical to the amino acid sequence of SEQ ID NO:1 or SEQ ID NO:11. In certain embodiments, provided herein are host cells comprising a UDP-glycosyltransferase comprising an amino acid sequence that is at least 70% identical to the amino acid sequence of SEQ ID NO:1 or SEQ ID NO:11. In certain embodiments, provided herein are host cells comprising a UDP-glycosyltransferase comprising an amino acid sequence that is at least 75% identical to the amino acid sequence of SEQ ID NO:1 or SEQ ID NO:11. In certain embodiments, provided herein are host cells comprising a UDP-glycosyltransferase comprising an amino acid sequence that is at least 80% identical to the amino acid sequence of SEQ ID NO:1 or SEQ ID NO:11. In certain embodiments, provided herein are host cells comprising a UDP-glycosyltransferase comprising an amino acid sequence that is at least 85% identical to the amino acid sequence of SEQ ID NO:1 or SEQ ID NO:11. In certain embodiments, provided herein are host cells comprising a UDP-glycosyltransferase comprising an amino acid sequence that is at least 90% identical to the amino acid sequence of SEQ ID NO:1 or SEQ ID NO:11. In certain embodiments, provided herein are host cells comprising a UDP-glycosyltransferase comprising an amino acid sequence that is at least 95% identical to the amino acid sequence of SEQ ID NO:1 or SEQ ID NO:11. In certain embodiments, provided herein are host cells comprising a UDP-glycosyltransferase comprising an amino acid sequence that is at least 96% identical to the amino acid sequence of SEQ ID NO:1 or SEQ ID NO:11. In certain embodiments, provided herein are host cells comprising a UDP-glycosyltransferase comprising an amino acid sequence that is at least 97% identical to the amino acid sequence of SEQ ID NO:1 or SEQ ID NO:11. In certain embodiments, provided herein are host cells comprising a UDP-glycosyltransferase comprising an amino acid sequence that is at least 98% identical to the amino acid sequence of SEQ ID NO:1 or SEQ ID NO:11. In certain embodiments, provided herein are host cells comprising a UDP-glycosyltransferase comprising an amino acid sequence that is at least 99% identical to the amino acid sequence of SEQ ID NO:1 or SEQ ID NO:11. In certain embodiments, provided herein are host cells comprising a UDP-glycosyltransferase comprising an amino acid sequence that is at least 60%, at least 99%, or at least any percentage between 60% and 99% identical to the amino acid sequence of SEQ ID NO:1 or SEQ ID NO:11.

In certain embodiments, provided herein are host cells comprising a UDP-glycosyltransferase comprising an amino acid sequence described herein, and is capable of converting RebA to RebD. In certain embodiments, provided herein are host cells comprising a UDP-glycosyltransferase comprising an amino acid sequence described herein, and is capable of beta 1,2 glycosylation of the C2' position of the 19-O glucose of a steviol glycoside. In certain embodiments, provided herein are host cells comprising a UDP-glycosyltransferase capable of converting RebA to RebD at an efficiency greater than 90%, 95%, 96%, or 97%, and wherein the UDP-glycosyltransferase comprises an amino acid sequence having at least 95% sequence identity to the amino acid sequence of SEQ ID NO:1 or SEQ ID NO:11.

In certain embodiments, provided herein are host cells comprising a nucleic acid encoding a UGT40087 comprising the amino acid sequence of SEQ ID NO:1 or SEQ ID NO:11. In certain embodiments, provided herein are host cells comprising a nucleic acid encoding a polypeptide comprising an amino acid sequence substantially identical to the amino acid sequence of SEQ ID NO:1 or SEQ ID NO:11. In certain embodiments, provided herein are host cells comprising a nucleic acid encoding a polypeptide comprising an amino acid sequence that is at least 60% identical to the amino acid sequence of SEQ ID NO:1 or SEQ ID NO:11. In certain embodiments, provided herein are host cells comprising a nucleic acid encoding a polypeptide comprising an amino acid sequence that is at least 65% identical to the amino acid sequence of SEQ ID NO:1 or SEQ ID NO:11. In certain embodiments, provided herein are host cells comprising a nucleic acid encoding a polypeptide comprising an amino acid sequence that is at least 70% identical to the amino acid sequence of SEQ ID NO:1 or SEQ ID NO:11. In certain embodiments, provided herein are host cells comprising a nucleic acid encoding a polypeptide comprising an amino acid sequence that is at least 75% identical to the amino acid sequence of SEQ ID NO:1 or SEQ ID NO:11. In certain embodiments, provided herein are host cells comprising a nucleic acid encoding a polypeptide comprising an amino acid sequence that is at least 80% identical to the amino acid sequence of SEQ ID NO:1 or SEQ ID NO:11. In certain embodiments, provided herein are host cells comprising a nucleic acid encoding a polypeptide comprising an amino acid sequence that is at least 85% identical to the amino acid sequence of SEQ ID NO:1 or SEQ ID NO:11. In certain embodiments, provided herein are host cells comprising a nucleic acid encoding a polypeptide comprising an amino acid sequence that is at least 90% identical to the amino acid sequence of SEQ ID NO:1 or SEQ ID NO:11. In certain embodiments, provided herein are host cells comprising a nucleic acid encoding a polypeptide comprising an amino acid sequence that is at least 95% identical to the amino acid sequence of SEQ ID NO:1 or SEQ ID NO:11. In certain embodiments, provided herein are host cells comprising a nucleic acid encoding a polypeptide comprising an amino acid sequence that is at least 96% identical to the amino acid sequence of SEQ ID NO:1 or SEQ ID NO:11. In certain embodiments, provided herein are host cells comprising a nucleic acid encoding a polypeptide comprising an amino acid sequence that is at least 97% identical to the amino acid sequence of SEQ ID NO:1 or SEQ ID NO:11. In certain embodiments, provided herein are host cells comprising a nucleic acid encoding a polypeptide comprising an amino acid sequence that is at least 98% identical to the amino acid sequence of SEQ ID NO:1 or SEQ ID NO:11. In certain embodiments, provided herein are host cells comprising a nucleic acid encoding a polypeptide comprising an amino acid sequence that is at least 99% identical to the amino acid sequence of SEQ ID NO:1 or SEQ ID NO:11. In certain embodiments, provided herein are host cells comprising a nucleic acid encoding a polypeptide comprising an amino acid sequence that is at least 60%, at least 99%, or any percentage between 60% and 99% identical to the amino acid sequence of SEQ ID NO:1 or SEQ ID NO:11.

In certain embodiments, provided herein are host cells comprising a heterologous nucleic acid comprising a nucleotide sequence of SEQ ID NO:13 which encodes UGT40087 having the sequence of SEQ ID NO:11. In certain embodiments, provided herein are host cells comprising a heterologous nucleic acid comprising a nucleotide sequence that is at least 60%, at least 65%, at least 70%, at least 75%, at least 80%, at least 85%, at least 90%, at least 95%, at least 96%, at least 97%, at least 98%, at least 99% identical to the nucleotide sequence of SEQ ID NO:13. In certain embodiments, provided herein are host cells comprising a heterologous nucleic acid comprising a nucleotide sequence that is at least 90%, at least 99%, or any percentage between 60% and 99% identical to the nucleotide sequence of SEQ ID NO:11.

In certain embodiments, provided herein are host cells comprising a functional domain of a UGT40087, wherein the UGT40087 comprises the amino acid sequence of SEQ ID NO:1 or SEQ ID NO:11. In certain embodiments, provided herein are host cells comprising a polypeptide comprising the N-terminal sugar acceptor domain of a UGT40087 comprising the amino acid sequence of SEQ ID NO:1 or SEQ ID NO:11. In certain embodiments, provided herein are host cells comprising a polypeptide comprising the C-terminal sugar donor domain of a UGT40087 comprising the amino acid sequence of SEQ ID NO:1 or SEQ ID NO:11. In certain embodiments, the sugar acceptor domain of a UGT40087 comprises about amino acid positions 1 to 214 of SEQ ID NO: 11 (which correspond to amino acid positions 1 to 215 of SEQ ID NO:1). In certain embodiments, the sugar donor domain of UGT40087 comprises about amino acid positions 215 to 435 of SEQ ID NO:11 (which correspond to amino acid positions 216 to 436 of SEQ ID NO:1). In certain embodiments, the sugar acceptor domain of UGT40087 comprises about amino acid positions 1 to 215 of SEQ ID NO:1. In certain embodiments, the sugar donor domain of comprises about amino acid positions of 216 to 436 of SEQ ID NO:1. In certain embodiments, the sugar acceptor domain and the sugar donor domain of a UGT40087 comprises a narrower range of amino acid residues than 1 to 214 or 215 to 435, respectively, in relation to SEQ ID NO:11. In certain embodiments, the sugar acceptor domain and the sugar donor domain of a UGT40087 comprises a narrower range of amino acid residues than 1 to 215 or 216 to 436, respectively, relation to SEQ ID NO:1.

In certain embodiments, provided herein are host cells comprising a polypeptide comprising an amino acid sequence substantially identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 60% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 65% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 70% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 75% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 80% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 85% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 90% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 95% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 96% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 97% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 98% identical to the amino acid sequence of the N-terminal sugar acceptor domain of SEQ ID NO:1 or SEQ ID NO:11. In certain embodiments, provided herein are host cells comprising a polypeptide comprising an amino acid sequence that is at least 99% identical to the amino acid sequence of the N-terminal sugar acceptor domain of SEQ ID NO:1 or SEQ ID NO:11. In certain embodiments, provided here are host cells comprising a polypeptide comprising an amino acid sequence that is at least 60%, at least 99%, or any percentage between 60% and 99% identical to the amino acid sequence of the N-terminal sugar acceptor domain of SEQ ID NO:1 or SEQ ID NO:11.

In certain embodiments, provided herein are host cells comprising a nucleic acid encoding a UGT40087 comprising the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence substantially identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 60% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 65% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 70% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 75% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 80% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 85% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 90% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 95% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 96% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 97% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 98% identical to the amino acid sequence of the N-terminal sugar acceptor domain of SEQ ID NO:1 or SEQ ID NO:11. In certain embodiments, provided herein are host cells comprising a nucleic acid encoding a polypeptide comprising an amino acid sequence that is at least 99% identical to the amino acid sequence of the N-terminal sugar acceptor domain of SEQ ID NO:1 or SEQ ID NO:11.

In certain embodiments, when three-dimensional modeled structures of UGT40087 and another UDP-glycosyltransferase were compared and analyzed, they revealed four loops (i.e., loop1, loop2, loop3, and loop4) that possess significant conformational differences at the N terminal sugar acceptor domain. See FIG. 6 and Example 12. The experimental results from exchanges of corresponding loop sequences between the two UGTs indicated that the loop1, loop2, loop3_1, loop3_2, and loop4_1 of UGT40087 can be substituted with their respective, corresponding loop sequences from other UDP-glycosyltransferases which are capable of converting RebA to RebD. In these embodiments, two versions of loop3 (i.e., loop3_1 and loop3_2) and loop_4 (i.e., loop4_1 and loop4_2) were designed to account for two possible loop lengths.

Thus, in certain embodiments, provided herein are host cells comprising a UDP-glycosyltransferase comprising an amino acid sequence that is at least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO: 1 or SEQ ID NO:11. In certain embodiments, provided herein are host cells comprising a heterologous nucleic acid encoding a UDP-glycosyltransferase comprising an amino acid sequence that is that least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO: 1 or SEQ ID NO:11. In certain embodiments, the UDP-glycosyltransferase further comprises a loop1 amino acid sequence of UGT40087 (i.e., SEQ ID NO:1 or SEQ ID NO:11), at a location of the UDP-glycosyltransferase that corresponds to the loop1 location of SEQ ID NO:1 or SEQ ID NO:11, respectively. In certain embodiments, the loop1 amino acid sequence of SEQ ID NO:1 or SEQ ID NO:11 has the amino acid sequence of SEQ ID NO:30. In certain embodiments, the loop1 amino acid sequence has the sequence of SEQ ID NO:28. In certain embodiments, the UDP-glycosyltransferase further comprises a variant loop1 amino acid sequence, at a location of the UDP-glycosyltransferase that corresponds to the loop1 location of SEQ ID NO:1 or SEQ ID NO:11, respectively. The variant loop1 amino acid sequence refers an amino acid sequence which differs from the reference loop1 amino acid sequence of SEQ ID NO:1 or SEQ ID NO:11 or the loop1 amino acid sequence having SEQ ID NO:28, but allows the UDP-glycosyltransferase comprising the variant loop1 amino acid to retain its activity to convert RebA to RebD and/or to convert stevioside to RebE.

In certain embodiments, the UDP-glycosyltransferase further comprises loop2 amino acid sequence of UGT40087 (i.e., SEQ ID NO:1 or SEQ ID NO:11), at a location of the UDP-glycosyltransferase that corresponds to the loop2 location of SEQ ID NO:1 or SEQ ID NO:11, respectively. In certain embodiments, the loop2 amino acid sequence of SEQ ID NO:1 or SEQ ID NO:1 has the amino acid sequence of SEQ ID NO:19. In certain embodiments, the UDP-glycosyltransferase further comprises a variant loop2 amino acid sequence, at a location of the UDP-glycosyltransferase that corresponds to the loop2 location of SEQ ID NO:1 or SEQ ID NO:11, respectively. The variant loop2 amino acid sequence refers to an amino acid sequence which differs from the reference loop2 amino acid sequence of SEQ ID NO:1 or SEQ ID NO:11, but allows the UDP-glycosyltransferase comprising the variant loop2 amino acid to retain its activity to convert RebA to RebD and/or to convert stevioside to RebE.

In certain embodiments, the UDP-glycosyltransferase further comprises loop3_1 amino acid sequence of UGT40087 (i.e., SEQ ID NO:1 or SEQ ID NO:11), at a location of the UDP-glycosyltransferase that corresponds to the loop3_1 location of SEQ ID NO:1 or SEQ ID NO:11, respectively. In certain embodiments, the loop3_1 amino acid sequence of SEQ ID NO:1 or SEQ ID NO:11 has the amino acid sequence of SEQ ID NO:20. In certain embodiments, the UDP-glycosyltransferase further comprises a variant loop3_1 amino acid sequence, at a location of the UDP-glycosyltransferase that corresponds to the loop3_1 location of SEQ ID NO:1 or SEQ ID NO:11, respectively. The variant loop3_1 amino acid sequence refers to an amino acid sequence which differs from the reference loop3_1 amino acid sequence of SEQ ID NO:1 or SEQ ID NO:11, but allows the UDP-glycosyltransferase comprising the variant loop3_1 amino acid to retain its activity to convert RebA to RebD and/or to convert stevioside to RebE.

In certain embodiments, the UDP-glycosyltransferase further comprises loop3_2 amino acid sequence of UGT40087 (i.e., SEQ ID NO:1 or SEQ ID NO:11), at a location of the UDP-glycosyltransferase that corresponds to the loop3_2 location of SEQ ID NO:1 or SEQ ID NO:11, respectively. In certain embodiments, the loop3_2 amino acid sequence of SEQ ID NO:1 or SEQ ID NO:11 has the amino acid sequence of SEQ ID NO:21. In certain embodiments, the UDP-glycosyltransferase further comprises a variant loop3_2 amino acid sequence, at a location of the UDP-glycosyltransferase that corresponds to the loop3_2 location of SEQ ID NO:1 or SEQ ID NO:11, respectively. The variant loop3_2 amino acid sequence refers to an amino acid sequence which differs from the reference loop3_2 amino acid sequence of SEQ ID NO:1 or SEQ ID NO:11, but allows the UDP-glycosyltransferase comprising the variant loop3_2 amino acid to retain its activity to convert RebA to RebD and/or to convert stevioside to RebE.

In certain embodiments, the UDP-glycosyltransferase further comprises loop4_1 amino acid sequence of UGT40087 (i.e., SEQ ID NO:1 or SEQ ID NO:11), at a location of the UDP-glycosyltransferase that corresponds to the loop4_1 location of SEQ ID NO:1 or SEQ ID NO:11, respectively. In certain embodiments, the loop4_1 amino acid sequence of SEQ ID NO:1 or SEQ ID NO:11 has the amino acid sequence of SEQ ID NO:22. In certain embodiments, the UDP-glycosyltransferase further comprises a variant loop4_1 amino acid sequence, at a location of the UDP-glycosyltransferase that corresponds to the loop4_1 location of SEQ ID NO:1 or SEQ ID NO:11, respectively. The variant loop4_1 amino acid sequence refers to an amino acid sequence which differs from the reference loop4_1 amino acid sequence of SEQ ID NO:1 or SEQ ID NO:11, but allows the UDP-glycosyltransferase comprising the variant loop4_1 amino acid to retain its activity to convert RebA to RebD and/or to convert stevioside to RebE.

In certain embodiments, the UDP-glycosyltransferase further comprises loop4_2 amino acid sequence of UGT40087 (i.e., SEQ ID NO:1 or SEQ ID NO:11), at a location of the UDP-glycosyltransferase that corresponds to the loop4_2 location of SEQ ID NO:1 or SEQ ID NO:11, respectively. The loop4_2 amino acid sequence of SEQ ID NO:1 or SEQ ID NO:11 has the amino acid sequence of SEQ ID NO:23.

In certain embodiments, provided herein are host cells comprising a UDP-glycosyltransferase comprising an amino acid sequence that is at least 84%, 85%, 86%, 87%, 88%, 89%, 90%, 91%, 92%, 93%, 94%, 95%, 96%, 97%, 98%, or 99% identical to the amino acid sequence of the N-terminal sugar acceptor domain of SEQ ID NO: 1 or SEQ ID NO:11, or a heterologous nucleic acid encoding the UDP-glycosyltransferase thereof, and further comprising any combination of the following:
  (a) The loop1 amino acid sequence of SEQ ID NO:1 or SEQ ID NO:11, the amino acid sequence of SEQ ID NO:28, or a variant loop1 amino acid sequence, at a location of the UDP-glycosyltransferase that corresponds to the loop1 location of SEQ ID NO:1 or SEQ ID NO:11, respectively;
  (b) the loop2 amino acid sequence of SEQ ID NO:1 or SEQ ID NO:11, or a variant loop2 amino acid sequence, at a location of the UDP-glycosyltransferase that corresponds to the loop2 location of SEQ ID NO:1 or SEQ ID NO:11, respectively;
  (c) the loop3_1 amino acid sequence of SEQ ID NO:1 or SEQ ID NO:11, or a variant loop3_1 amino acid sequence, at a location of the UDP-glycosyltransferase that corresponds to the loop 3_1 location of SEQ ID NO:1 or SEQ ID NO:11, respectively;
  (d) the loop3_2 amino acid sequence of SEQ ID NO:1 or SEQ ID NO:11, or a variant loop3_2 amino acid sequence, at a location of the UDP-glycosyltransferase that corresponds to the loop3_2 location of SEQ ID NO:1 or SEQ ID NO:11, respectively;
  (e) the loop4_1 amino acid sequence of SEQ ID NO:1 or SEQ ID NO:11, or a variant loop4_1 amino acid sequence, at a location of the UDP-glycosyltransferase that corresponds to the loop4_1 location of SEQ ID NO:1 or SEQ ID NO:11, respectively; and
  (f) the loop4_2 amino acid sequence of SEQ ID NO:1 or SEQ ID NO:11, at a location of the UDP-glycosyltransferase that corresponds to the loop4_2 location of SEQ ID NO:1 or SEQ ID NO:11, respectively.

In certain embodiments, when three-dimensional modeled structures of UDP-glycosyltransferases capable of converting RebA to RebD were compared and analyzed, it was discovered that loop4_1 of UGT40087, when incorporated into the corresponding loop4_1 location of another UDP-glycosyltransferase (and replacing its native loop4_1 amino acid sequence) led to superior activity of a variant UDP-glycosyltransferase in terms of its ability to convert RebA to RebD. See Example 12. These results indicate that the loop4_1 amino acid sequence of any suitable UDP-glycosyltransferase can be substituted with the loop4_1 amino acid sequence of SEQ ID NO:1 or SEQ ID NO:11 to convert RebA to RebD.

Therefore, in certain embodiments, provided herein are host cells comprising a UDP-glycosyltransferase comprising an amino acid sequence that is at least 61%, 65%, 70%, 75%, 80%, 85%, 90%, or 95% identical to the amino acid sequence of the N-terminal sugar acceptor domain of SEQ ID NO:1 or SEQ ID NO:11, and further comprises the loop4_1 amino acid sequence (i.e., SEQ ID NO:22) of UGT40087 (i.e., SEQ ID NO:1 or SEQ ID NO:11). In certain embodiments, provided herein are host cells comprising a heterologous nucleic acid encoding an UDP-glycosyltransferase comprising an amino acid sequence that is at least 61%, 65%, 70%, 75%, 80%, 85%, 90%, or 95% identical to the amino acid sequence of the N-terminal sugar acceptor domain of SEQ ID NO:1 or SEQ ID NO:11, and further comprises the loop4_1 amino acid sequence (e.g., SEQ ID NO:22) of SEQ ID NO:1 or SEQ ID NO:11. In certain embodiments, any suitable UDP-glycosyltransferase which comprises an amino acid sequence that is at least 50%, 55%, 60%, 65%, 70%, 75%, 80%, 85%, 90%, or 95% to SEQ ID NO:1 or SEQ ID NO:11 can be used to integrate the loop4_1 amino acid sequence from SEQ ID NO:1 or SEQ ID NO:11 at its corresponding loop4_1 location (replacing its native loop4_1 amino acid sequence). For example, Ob_UGT91B_like, Hv_UGT_V1, Sl_UGT_101249881, Sr.UGT_g252778, Os_UGT_91C1, Bd_UGT10840, Bd_UGT10850, or Si91Dlike can be used as a base to integrate the loop4_1 amino acid sequence from SEQ ID NO:1 or SEQ ID NO:11 at its corresponding loop4_1 location. In certain embodiments, the UDP-glycosyltransferase comprises an amino acid sequence of SEQ ID NO:25.

In certain embodiments, provided herein are host cells comprising a polypeptide comprising an amino acid sequence substantially identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 60% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 65% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 70% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 75% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 80% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 85% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 90% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 95% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 96% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 97% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 98% identical to the amino acid sequence of the C-terminal sugar donor domain of SEQ ID NO:1 or SEQ ID NO:11. In certain embodiments, provided herein are host cells comprising a polypeptide comprising an amino acid sequence that is at least 99% identical to the amino acid sequence of the C-terminal sugar donor domain of SEQ ID NO:1 or SEQ ID NO:11.

In certain embodiments, provided herein are host cells comprising a nucleic acid encoding a UGT40087 comprising the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence substantially identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 60% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 65% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 70% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 75% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 80% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 85% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 90% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 95% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 96% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 97% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 98% identical to the amino acid sequence of the C-terminal sugar donor domain of SEQ ID NO:1 or SEQ ID NO:11. In certain embodiments, provided herein are host cells comprising a nucleic acid encoding a polypeptide comprising an amino acid sequence that is at least 99% identical to the amino acid sequence of the C-terminal sugar donor domain of SEQ ID NO:1 or SEQ ID NO:11.

In certain embodiments, the N-terminal sugar acceptor domains and the C-terminal sugar donor domains were recombined to either alter substrate specificity or catalytic activity. As described in detail in Example 11, it was determined that when a sugar donor domain from another UDP-glycosyltransferase capable of converting RebA to RebD was recombined with the sugar acceptor domain of SEQ ID NO:1 or SEQ ID NO:11, the chimeric UDP-glycosyltransferases retained their ability to convert RebA to RebD.

Thus, in certain embodiments, provided herein are host cells comprising a UDP-glycosyltransferase comprising an amino acid sequence that is at least 60%, 65%, 70%, 75%, 80%, 85%, 90%, or 95% identical to the amino acid sequence of the C-terminal sugar donor domain of SEQ ID NO: 1 or SEQ ID NO:11. In certain embodiments, provided herein are host cells comprising a heterologous nucleic acid encoding a UDP-glycosyltransferase comprising an amino acid sequence that is that least 60%, 65%, 70%, 75%, 80%, 85%, 90%, or 95% identical to the amino acid sequence of the C-terminal sugar donor domain of SEQ ID NO: 1 or SEQ ID NO:11. As shown in Example 11, the C-terminal sugar donor domain is relatively exchangeable with other UDP-glycosyltransferase comprising a sequence identity of at least 50%, 55%, 60%, 65%, 70%, 75%, 80%, 85%, 90%, or 95%. In certain embodiments, the UDP-glycosyltransferase further comprises a C-terminal sugar donor domain from other UDP-glycosyltransferase. Examples of other UDP-glycosyltransferases with suitable C-terminal sugar donor domains include Ob_UGT91B_like, Hv_UGT_V1, SI_UGT_101249881, Sr.UGT_g252778, Os_UGT_91C1, Bd_UGT10840, Bd_UGT10850, or Si91Dlike.

In certain embodiments, it was discovered that certain amino acid residues in the N-terminal sugar acceptor domain can restore the catalytic activity of a non-functional, putative UDP-glycosyltransferase into an active UDP-glycosyltransferase. Therefore, provided herein are host cells comprising a UDP-glycosyltransferase comprising an amino acid sequence that is at least 60%, 65%, 70%, 75%, 80%, 85%, 90%, 91%, 92%, 93%, 94%, 95%, 96%, 97%, 98%, or 99% identical to the amino acid sequence of the N-terminal sugar acceptor domain of SEQ ID NO:1 or SEQ ID NO:11, and further comprises one or more of the following amino acid residues:

(a) valine at an amino acid position of the UDP-glycosyltransferase that corresponds to amino acid position 11 of SEQ ID NO:11;

(b) isoleucine at an amino acid position of UDP-glycosyltransferase that corresponds to amino acid position 12 of SEQ ID NO:11;

(c) proline at an amino acid position of the UDP-glycosyltransferase that corresponds to amino acid position 55 of SEQ ID NO:11;

(d) glutamic acid at an amino acid position of the UDP-glycosyltransferase that corresponds to amino acid position 90 of SEQ ID NO:11;

(e) serine at an amino acid position of the UDP-glycosyltransferase that corresponds to amino acid position 203 of SEQ ID NO:11;

(f) glutamic acid at an amino acid position of the UDP-glycosyltransferase that corresponds to amino acid position 223 of SEQ ID NO:11; or (g) valine at an amino acid position of the UDP-glycosyltransferase that corresponds to amino acid position 413 of SEQ ID NO:11, wherein the amino acid positions of the UDP-glycosyltransferase that correspond to the amino acid positions of SEQ ID NO:11 are determined by sequence alignment.

In certain embodiments, provided herein are host cells comprising a UDP-glycosyltransferase comprising an amino acid sequence of SEQ ID NO:24.

In certain embodiments, the host cell comprises a variant of the UGT40087 polypeptide described above. In certain embodiments, the variant can comprise up to 15, 10, 9, 8, 7, 6, 5, 4, 3, 2, or 1 amino acid substitutions relative to the UGT40087 polypeptide. In certain embodiments, the variant can comprise up to 15, 10, 9, 8, 7, 6, 5, 4, 3, 2, or 1 conservative amino acid substitutions relative to the UGT40087 polypeptide. In certain embodiments, any of the nucleic acids described herein can be optimized for the host cell, for instance codon optimized.

In embodiments described herein, any suitable method can be used to determine corresponding amino acid positions or corresponding loop locations of two polypeptides. In certain embodiments, the sequences of a UDP-glycosyltransferase and the reference sequence SEQ ID NO:11 can be aligned using Clustal Omega using its default parameters. In other embodiment, the sequences of a UDP-glycosyltransferase and the reference sequence SEQ ID NO:11 can be aligned using structural alignments such as SWISS-MODEL, which is a protein structure homology-modelling server, accessible via the ExPASy web server, or from the program DeepView (Swiss Pdb-Viewer).

While SEQ ID NO:11 is referred to as the reference sequence for determining corresponding amino acid positions or loop locations for a UDP-glycosyltransferase, in certain embodiments, SEQ ID NO:1 can be also used as a reference sequence for sequence alignment.

Figure 1A:
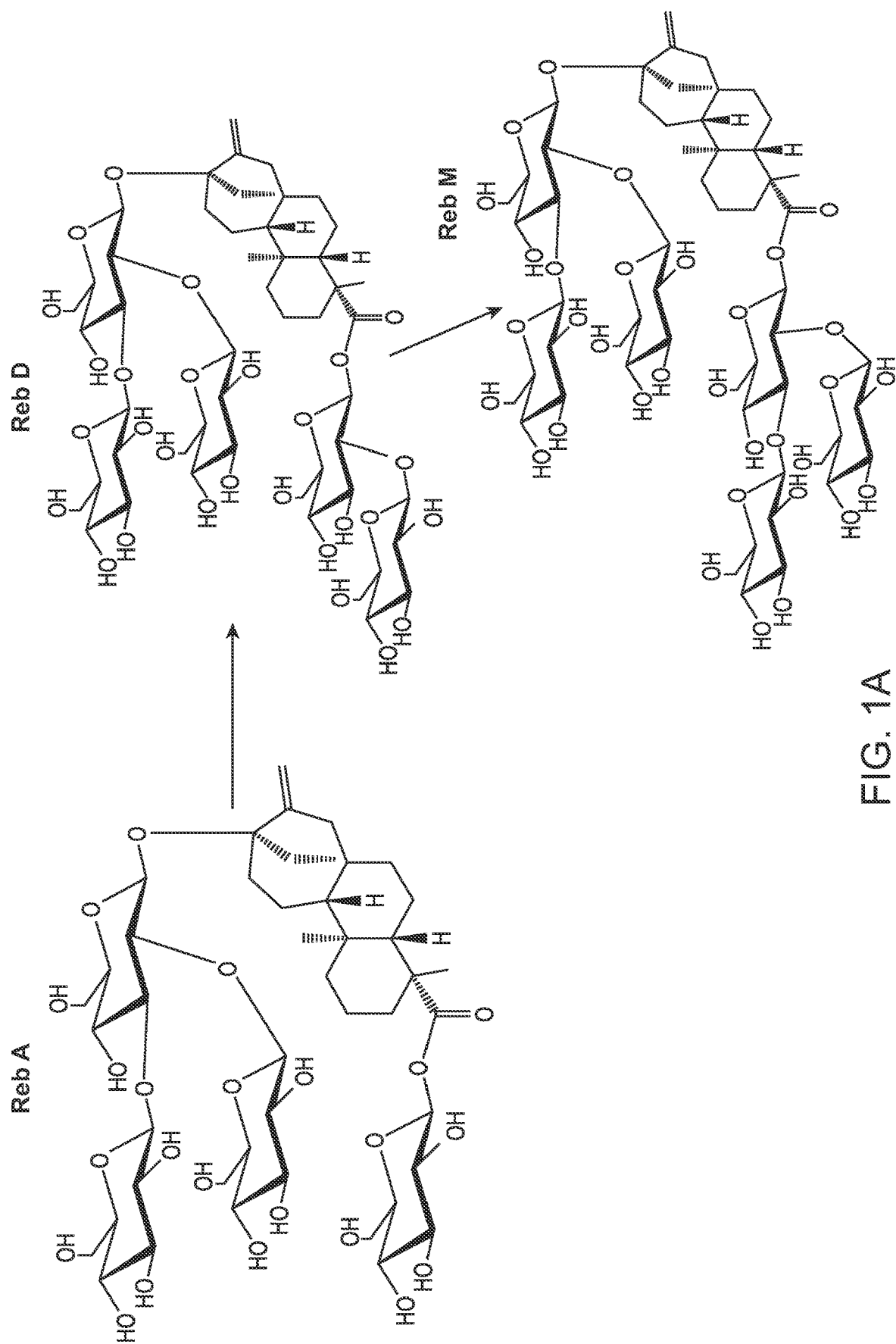

In certain embodiments, RebA is as shown in FIG. 1A. In certain embodiments, a UGT40087 or a variant UGT40087 is capable of catalyzing the reaction of a sugar residue, forming the 13 linkage, to the C-2' position of the 19-O-glucose of RebA to produce RebD as shown in FIG. 1A. In certain embodiments, the UGT40087 or variant UGT40087 is capable of catalyzing the reaction of a hexose residue, in the β formation, to the C-2' of the 19-O-glucose of RebA. In certain embodiments, the UGT40087 is capable of catalyzing the reaction of a glucose residue, in the β formation, to the C-2' of the 19-O-glucose of RebA.

Figure 2A:
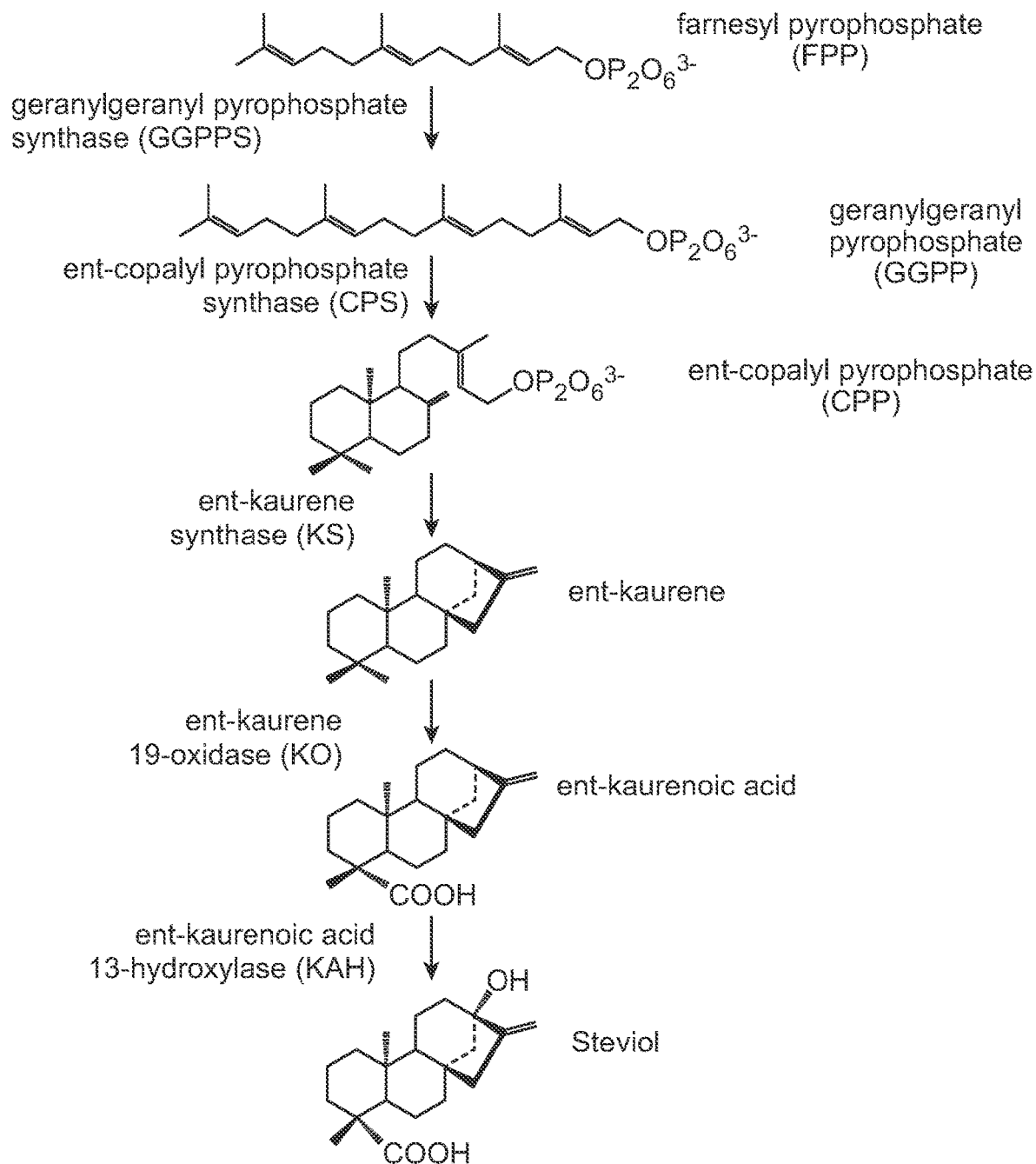
Figure 2B:
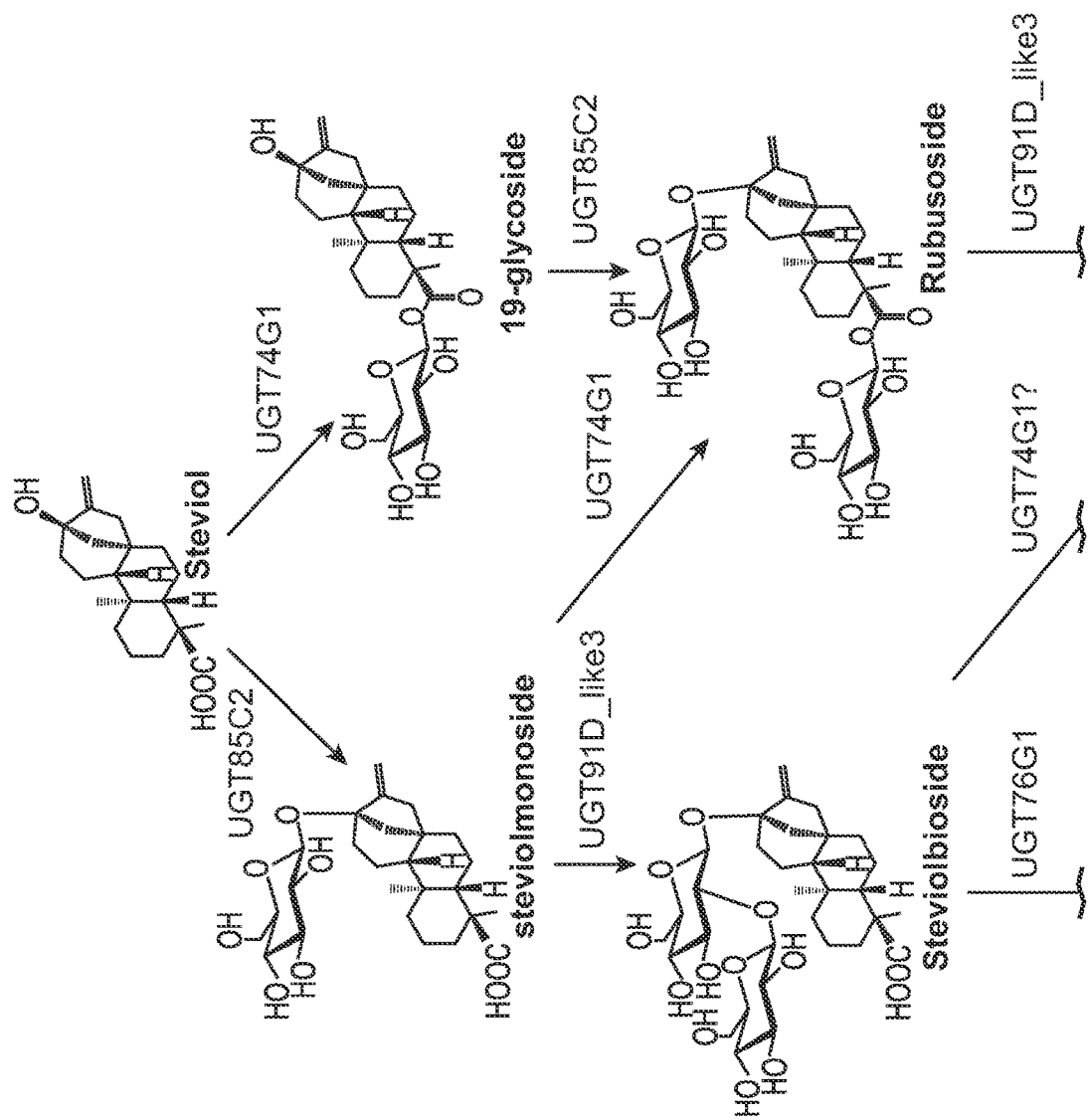
Figure 2B:
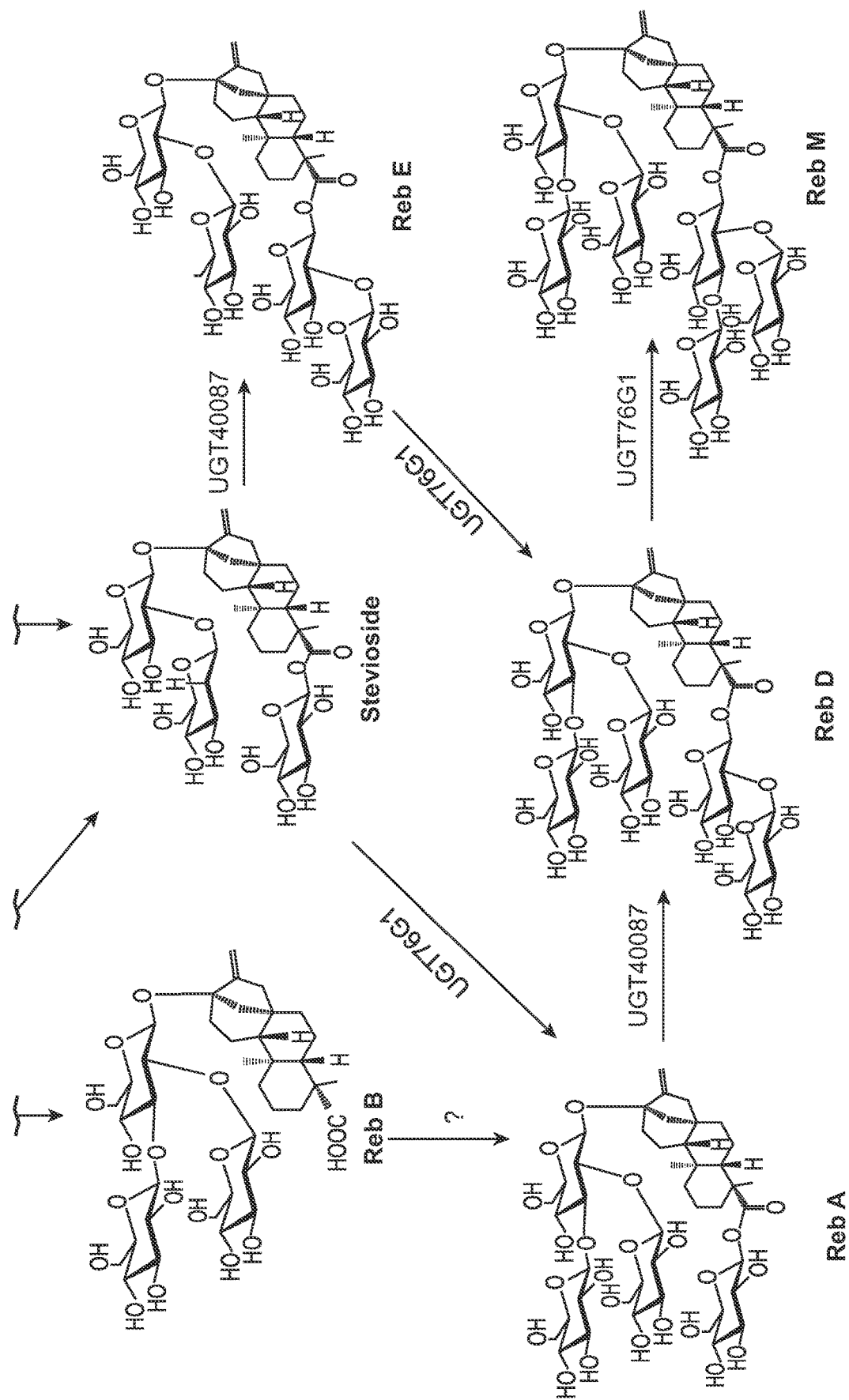

In certain embodiments, RebE is as shown in FIG. 2B. In certain embodiments, a UGT40087 or a variant UGT40087 is capable of catalyzing the reaction of a sugar residue, forming the β linkage, to the C-2' position of the 19-O-glucose of stevioside to produce RebE as shown in FIG. 2B. In certain embodiments, the UGT40087 or variant UGT40087 is capable of catalyzing the reaction of a hexose residue, in the β formation, to the C-2' of the 19-O-glucose of stevioside. In certain embodiments, the UGT40087 or variant UGT40087 is capable of catalyzing the reaction of a glucose residue, in the β formation, to the C-2' of the 19-O-glucose of stevioside.

In certain embodiments, a UGT40087 or a variant UGT40087 does not catalyze the reaction of adding a second sugar moiety to steviolmonoside (i.e., 13-O-steviol glycoside) at a detectable level. In certain embodiments, the UGT40087 or variant UGT40087 does not catalyze the reaction of adding a second sugar moiety to rubusoside (i.e., 19-O-steviol glycoside) at a detectable level.

In certain embodiments, RebD is as shown in FIG. 1A. In certain embodiments, the host cell further comprises one or more enzymes capable of converting RebA to RebD. In certain embodiments, the host cell comprises a UGT40087 and/or a variant UGT40087 for conversion of RebA to RebD.

In certain embodiments, a UGT76G1 is capable of catalyzing the reaction of a sugar residue to convert RebD to RebM as shown in FIG. 1A. In certain embodiments, the host cells further comprise one or more enzymes capable of converting RebD to RebM. In certain embodiments, the host cell further comprises a UGT76G1 capable of converting RebD to RebM.

In certain embodiments, RebM2 is shown in FIG. 1B. RebM2 is an isomer of RebM with a single wrong glucose linkage as shown in FIG. 1B. RebM2 has Glcβ(1-2)[Glcβ(1-6)]Glcβ1-at the 19 carbon position (COOH) instead of the desired Glcβ (1-2)[Glcβ (1-3)]Glcβ1-for RebM.

Those of skill will recognize that in certain applications, RebM2 might be an undesired side product. Advantageously, in certain embodiments, the UGT40087 (or variant UGT40087) and host cells provided herein are capable of producing little or no RebM2. The amount of RebM2 can be expressed as a ratio of RebM to RebM2. In certain embodiments, the ratio of RebM to RebM2 is at least 2:1. In certain embodiments, the ratio of RebM to RebM2 is at least 3:1. In certain embodiments, the ratio of RebM to RebM2 is at least 4:1. In certain embodiments, the ratio of RebM to RebM2 is at least 5:1. In certain embodiments, the ratio of RebM to RebM2 is at least 10:1. In certain embodiments, the ratio of RebM to RebM2 is at least 100:1. In certain embodiments, the ratio of RebM to RebM2 is at least 1000:1. In certain embodiments, the ratio of RebM to RebM2 is at least 10000:1. In certain embodiments, the UGT40087 (or variant UGT40087) and host cells provided herein produce an undetectable level of RebM2.

While the UGT40087 or any variant UGT40087 of the host cells accepts RebA as a substrate, the source of RebA can be any source deemed suitable to those of skill. In certain embodiments, the UGT40087 or any variant UGT40087 can be contacted with RebA. In certain embodiments, the host cell can be contacted with RebA. In certain embodiments, the UGT40087 or any variant of UGT40087 can be contacted with a composition comprising one or more steviol glycosides. In certain embodiments, the composition comprises RebA. In certain embodiments, the composition comprises stevioside. In certain embodiments, the composition is derived from natural products isolated from *Stevia rebaudiana* leaves. In certain embodiments, the composition is microbially derived. In certain embodiments, the host cell can be contacted with a composition comprising one or more steviol glycosides.

In certain embodiments, any variant UGT40087 suitable for catalyzing a desired reaction can be screened for any suitable methods known in the art. For example, a suitable variant UGT40087 can be assayed in vivo by expressing a heterologous nucleic acid encoding a variant UGT40087 and screening cells that produce functional variant UGT40087 capable of adding a sugar at a desired location of a substrate (e.g., the C2' position of the 19-O-glucose of a steviol glycosides or other substrates). Exemplary screening methods are described in Examples 3-7 below. In another example, a suitable variant UGT40087 can be screened in vitro by contacting a variant UGT40087 with a substrate such as RebA. In this example, assaying for the presence of RebD can be used as a test to determine whether a variant UGT40087 is suitable enzyme. The reaction can be analyzed by LC-MS or other known methods in the art. See, e.g. WO 2013/022989.

In certain embodiments, a variant UGT40087 is considered suitable in converting RebA to RebD (or from any suitable substrate to its product by glycosylation) if it is capable of converting RebA to RebD at an efficiency of greater than 30%, 40%, 50%, 60%, 70%, 80%, 90%, 95%, 96%, or 97% in vivo.

In some embodiments, other suitable UDP-glycosyltransferases discovered in the present application can be used in addition or in alternative to UGT40087. These include, for example, UDP-glycosyltransferases sr. UGT_9252778, Bd_UGT10840, Hv_UGT_V1, Bd_UGT10850, and Ob_UGT91B1_like. In certain embodiments, UDP-glycosyltransferase sr.UGT_9252778 comprises SEQ ID NO: 2. In certain embodiments, UDP-glycosyltransferase Bd_UGT10840 comprises SEQ ID NO: 3. In certain embodiments, UDP-glycosyltransferase Hv_UGT_V1 comprises SEQ ID NO: 4. In certain embodiments, UDP-glycosyltransferase Bd_UGT10850 comprises SEQ ID NO: 5. In certain embodiments, UDP-glycosyltransferase Ob_UGT91B1_like comprises SEQ ID NO: 6. Any discussions related to compositions and methods relevant to UGT40087 described herein may also apply to these other UDP-glycosyltransferases.

For instance, in some embodiments, the host cells comprise the enzyme activity of uridine diphosphate glycosyltransferase sr.UGT_9252778, Bd_UGT10840, Hv_UGT_V1, Bd_UGT10850, and/or Ob_UGT91B1_like. In certain embodiments, one or more of these enzymes are capable of converting RebA to RebD at an efficiency of greater than 40%. In certain embodiments, one or more of these enzymes are capable of converting RebA to RebD at an efficiency of greater than 45%. In certain embodiments, one or more of these enzymes are capable of converting RebA to RebD at an efficiency of greater than 50%. In certain embodiments, one or more of these enzymes are capable of converting RebA to RebD at an efficiency of greater than 55%. In certain embodiments, one or more of these enzymes are capable of converting RebA to RebD at an efficiency of greater than 60%. In certain embodiments, one or more of these enzymes are capable of converting RebA to RebD at an efficiency of greater than 65%. In certain embodiments, one or more of these enzymes are capable of converting RebA to RebD at an efficiency of greater than 70%. In certain embodiments, one or more of these enzymes are capable of converting RebA to RebD at an efficiency of greater than 75%. In certain embodiments, one or more of these enzymes are capable of converting RebA to RebD at an efficiency of greater than 80%. In certain embodiments, one or more of these enzymes are capable of converting RebA to RebD at an efficiency of greater than 85%. In certain embodiments, one or more of these enzymes are capable of converting RebA to RebD at an efficiency of greater than 90%. In certain embodiments, one or more of these enzymes are capable of converting RebA to RebD at an efficiency of greater than 95%.

In certain embodiments, provided herein are host cells comprising any one or more of sr.UGT_9252778, Bd_UGT10840, Hv_UGT_V1, Bd_UGT10850, and/or Ob_UGT91B1_like comprising an amino acid sequence of SEQ ID NOS: 2, 3, 4, 5, or 6, respectively. In certain embodiments, provided herein are host cells comprising a polypeptide comprising an amino acid sequence that is at least 60%, at least 70%, at least 75%, at least 80%, at least 85%, at least 90%, at least 95%, at least 96%, at least 97%, at least 98%, at least 99%, or 100% identical to the amino acid sequence of SEQ ID NOS: 2, 3, 4, 5, or 6.

In advantageous embodiments, the host cell can comprise one or more enzymatic pathways capable of making RebA, said pathways taken individually or together. In certain embodiments, the host cells comprise one or more enzymes capable of converting geranylgeranyl diphosphate to RebA. Useful enzymes and nucleic acids encoding the enzymes are known to those of skill in the art. Particularly useful enzymes and nucleic acids are described in the sections below and further described, for example, in US 2014/0329281 A1, US 2014/0357588 A1, US 2015/0159188, WO 2016/038095 A2, and US 2016/0198748 A1.

Figure 1C:
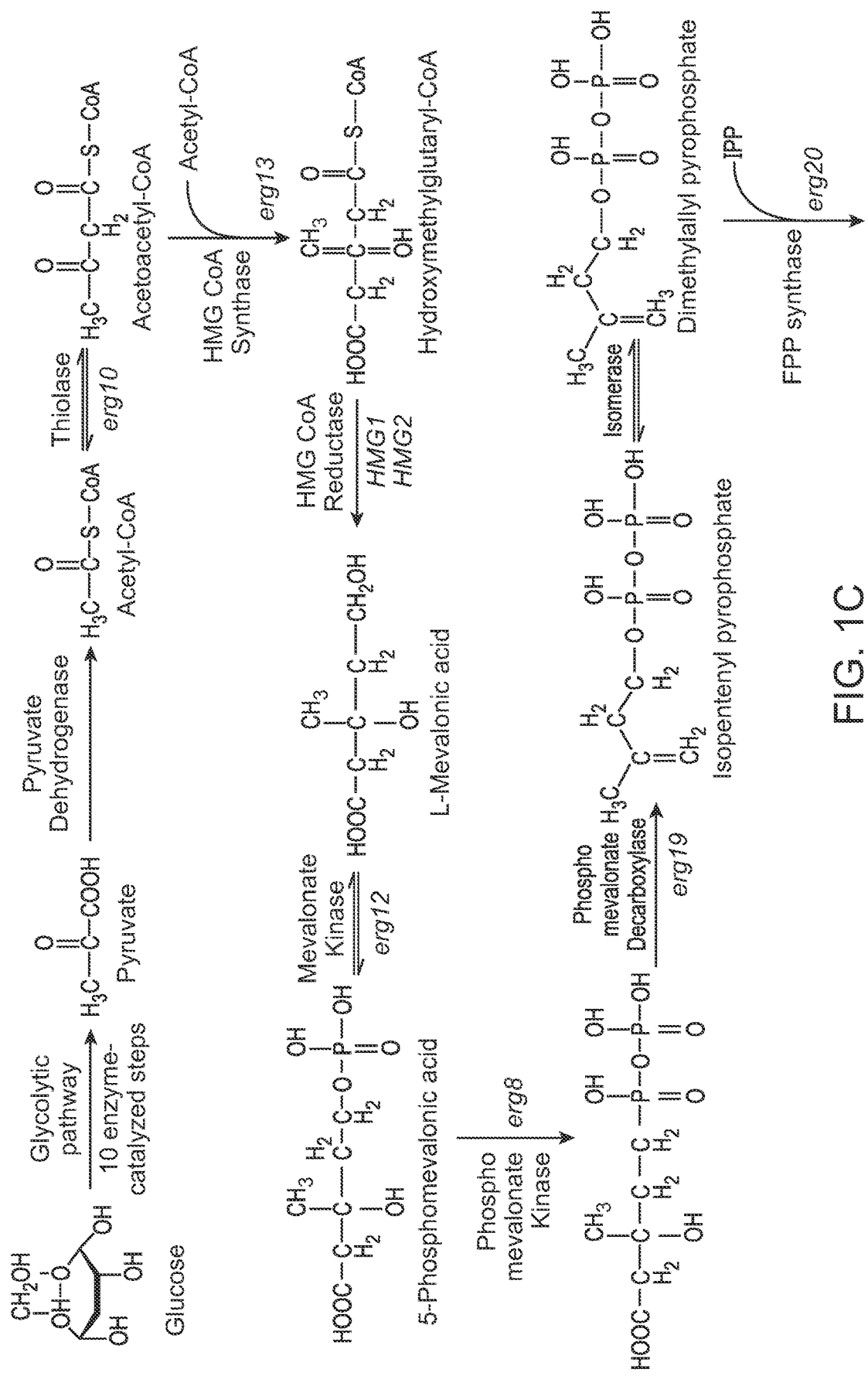

In further embodiments, the host cells further comprise one or more enzymes capable of making geranylgeranyl diphosphate from a carbon source. These include enzymes of the DXP pathway and enzymes of the MEV pathway. Useful enzymes and nucleic acids encoding the enzymes are known to those of skill in the art. Exemplary enzymes of each pathway are described below and further described, for example, in US 2016/0177341 A1. The MEV pathway is also shown in FIG. 1C.

In certain embodiments, the additional enzymes are native. In advantageous embodiments, the additional enzymes are heterologous. In certain embodiments, two enzymes can be combined in one polypeptide.

6.3 Non-Naturally Occurring UDP-Glycosyltransferase Polypeptides and Nucleic Acids In another aspect, provided herein are non-naturally occurring, variant UDP-glycosyltransferases which include modification(s) of amino acid residues compared to a reference sequence (e.g., SEQ ID NO:1) and yet still retains the activity as a UDP-glycosyltransferase to convert RebA to RebD and/or from stevioside to RebE. In certain embodiments, non-naturally occurring, variant UDP-glycosyltransferases can include up to 30, 25, 20, 15, 10, 9, 8, 7, 6, 5, 4, 3, 2, or 1 amino acid substitutions, deletions, additions, and/or insertions at certain amino acid positions or locations compared to a reference sequence (e.g., SEQ ID NO:1 or SEQ ID NO:11). In certain embodiments, non-naturally occurring, variant UDP-glycosyltransferases comprise any of the variant UDP-glycosyltransferases described herein, in particular those described in Section 6.2.

In another aspects, provided herein are non-naturally occurring, variant UDP-glycosyltransferases which include modification(s) of nucleic acid residues compared to a reference sequence (e.g., SEQ ID NO:26), and yet, when translated into a protein, the protein retains the activity as a UDP-glycosyltransferase to convert RebA to RebD and/or to convert stevioside to RebE. In certain embodiments, non-naturally occurring, variant UDP-glycosyltransferases can encode any of the variant UDP-glycosyltransferases described herein, in particular those described in Section 6.2.

6M 6.4 Cell Strains

Host cells useful compositions and methods provided herein include archae, prokaryotic, or eukaryotic cells.

Suitable prokaryotic hosts include, but are not limited to, any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host microbe is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the host microbe is a strain of the genus *Candida*, such as *Candida lipolytica, Candida guilliermondii, Candida krusei, Candida pseudotropicalis*, or *Candida utilis*.

In a particular embodiment, the host microbe is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host microbe is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host microbe is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

6.5 The Steviol and Steviol Glycoside Biosynthesis Pathways

In some embodiments, a steviol biosynthesis pathway and/or a steviol glycoside biosynthesis pathway is activated in the genetically modified host cells provided herein by engineering the cells to express polynucleotides and/or polypeptides encoding one or more enzymes of the pathway. FIG. 2A illustrates an exemplary steviol biosynthesis pathway. FIG. 2B illustrates an exemplary steviol glycoside biosynthesis pathway starting from steviol to various steviol glycosides.

Thus, in some embodiments, the genetically modified host cells provided herein comprise a heterologous polynucleotide encoding a polypeptide having geranylgeranyl diphosphate synthase (GGPPS) activity. In some embodiments, the genetically modified host cells provided herein comprise a heterologous polynucleotide encoding a polypeptide having copalyl diphosphate synthase or ent-copalyl pyrophosphate synthase (CDPS; also referred to as ent-copalyl pyrophosphate synthase or CPS) activity. In some embodiments, the genetically modified host cells provided herein comprise a heterologous polynucleotide encoding a polypeptide having kaurene synthase (KS; also referred to as ent-kaurene synthase) activity. In some embodiments, the genetically modified host cells provided herein comprise a heterologous polynucleotide encoding a polypeptide having kaurene oxidase (KO; also referred to as ent-kaurene 19-oxidase) activity. In some embodiments, the genetically modified host cells provided herein comprise a heterologous polynucleotide encoding a polypeptide having steviol synthase (also referred to as ent-kaurenoic acid 13-hydroxylase or KAH) activity. In some embodiments, the genetically modified host cells provided herein comprise a heterologous polynucleotide encoding a polypeptide having cytochrome P450 reductase (CPR) activity.

In some embodiments, the genetically modified host cells provided herein comprise a heterologous polynucleotide encoding a polypeptide having UGT74G1 activity. In some embodiments, the genetically modified host cells provided herein comprise a heterologous polynucleotide encoding a polypeptide having UGT76G1 activity. In some embodiments, the genetically modified host cells provided herein comprise a heterologous polynucleotide encoding a polypeptide having UGT85C2 activity. In some embodiments, the genetically modified host cells provided herein comprise a heterologous polynucleotide encoding a polypeptide having UGT91D activity. In some embodiments, the genetically modified host cells provided herein comprise a heterologous polynucleotide encoding a polypeptide having UGT40087 activity.

In certain embodiments, the host cell comprises a variant. In certain embodiments, the variant can comprise up to 15, 10, 9, 8, 7, 6, 5, 4, 3, 2, or 1 amino acid substitutions relative to the relevant polypeptide. In certain embodiments, the variant can comprise up to 15, 10, 9, 8, 7, 6, 5, 4, 3, 2, or 1 conservative amino acid substitutions relative to the reference polypeptide. In certain embodiments, any of the nucleic acids described herein can be optimized for the host cell, for instance codon optimized.

Exemplary nucleic acids and enzymes of a steviol biosynthesis pathway and/or a steviol glycoside biosynthesis pathway are described below.

6.5.1 Geranylgeranyl Diphosphate Synthase (GGPPS)

Geranylgeranyl diphosphate synthases (EC 2.5.1.29) catalyze the conversion of farnesyl pyrophosphate into geranylgeranyl diphosphate (also known as geranylgeranyl pyrophosphate). Illustrative examples of enzymes include those of *Stevia rebaudiana* (accession no. ABD92926), *Gibberella fujikuroi* (accession no. CAA75568), *Mus musculus* (accession no. AAH69913), *Thalassiosira pseudonana* (accession no. XP_002288339), *Streptomyces clavuligerus* (accession no. ZP_05004570), *Sulfulobus acidocaldarius* (accession no. BAA43200), *Synechococcus* sp. (accession no. ABC98596), *Arabidopsis thaliana* (accession no. NP_195399), *Blakeslea trispora* (accession no. AFC92798.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these GGPPS nucleic acids. In certain embodiments, provided herein are cells and methods using a nucleic acid that encodes a polypeptide having at least 80%, 85%, 90%, 95% sequence identity to at least one of these GGPPS enzymes.

6.5.2 Copalyl Diphosphate Synthase (CDPS)

Copalyl diphosphate synthases (EC 5.5.1.13) catalyze the conversion of geranylgeranyl diphosphate into copalyl diphosphate. Illustrative examples of enzymes include those of *Stevia rebaudiana* (accession no. AAB87091), *Streptomyces clavuligerus* (accession no. EDY51667), *Bradyrhizobium japonicum* (accession no. AAC28895.1), *Zea mays* (accession no. AY562490), *Arabidopsis thaliana* (accession no. NM_116512), *Oryza sativa* (accession no. Q5MQ85.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS nucleic acids. In certain embodiments, provided herein are cells and methods using a nucleic acid that encodes a polypeptide having at least 80%, 95%, 90%, or 95% sequence identity to at least one of these CDPS enzymes.

6.5.3 Kaurene Synthase (KS)

Kaurene synthases (EC 4.2.3.19) catalyze the conversion of copalyl diphosphate into kaurene and diphosphate. Illustrative examples of enzymes include those of *Bradyrhizobium japonicum* (accession no. AAC28895.1), *Phaeosphaeria* sp. (accession no. 013284), *Arabidopsis thaliana* (accession no. Q9SAK2), *Picea glauca* (accession no. ADB55711.1) and US 2014/0329281 A1. Nucleic acids encoding these enzymes are useful in the cells and methods provided herein. In certain embodiments, provided herein are cells and methods using a nucleic acid having at least 80%, 85%, 90%, or 95% sequence identity to at least one of these KS nucleic acids. In certain embodiments, provided herein are cells and methods using a nucleic acid that encodes a polypeptide having at least 80%, 85%, 85%, 90%, or 95% sequence identity to at least one of these KS enzymes.

6.5.4 Bifunctional Copalyl Diphosphate Synthase (CDPS) and Kaurene Synthase (KS)

CDPS-KS bifunctional enzymes (EC 5.5.1.13 and EC 4.2.3.19) also can be used. Illustrative examples of enzymes include those of *Phomopsis amygdali* (accession no. BAG30962), *Physcomitrella patens* (accession no. BAF61135), *Gibberella fujikuroi* (accession no. Q9UVY5.1), and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CDPS-KS nucleic acids. In certain embodiments, provided herein are cells and methods using a nucleic acid that encodes a polypeptide having at least 80%, 85%, 90%, or 95% sequence identity to at least one of these CDPS-KS enzymes.

6.5.5 Ent-Kaurene Oxidase (KO)

Ent-kaurene oxidases (EC 1.14.13.78; also referred to as kaurene oxidases herein) catalyze the conversion of kaurene into kaurenoic acid. Illustrative examples of enzymes include those of *Oryza sativa* (accession no. Q5Z5R4), *Gibberella fujikuroi* (accession no. 094142), *Arabidopsis thaliana* (accession no. Q93ZB2), *Stevia rebaudiana* (accession no. AAQ63464.1), *Pisum sativum* (Uniprot no. Q6XAF4) and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KO nucleic acids. In certain embodiments, provided herein are cells and methods using a nucleic acid that encodes a polypeptide having at least 80%, 85%, 90%, or 95% sequence identity to at least one of these KO enzymes.

6.5.6 Steviol Synthase (KAH)

Steviol synthases, or kaurenoic acid hydroxylases (KAH), (EC 1.14.13) catalyze the conversion of kaurenoic acid into steviol. Illustrative examples of enzymes include those of *Stevia rebaudiana* (accession no. ACD93722), *Stevia rebaudiana* (SEQ ID NO:10) *Arabidopsis thaliana* (accession no. NP 197872), *Vitis vinifera* (accession no. XP 002282091), *Medicago* trunculata (accession no. ABC59076), and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these KAH nucleic acids. In certain embodiments, provided herein are cells and methods using a nucleic acid that encodes a polypeptide having at least 80%, 85%, 90%, or 95% sequence identity to at least one of these KAH enzymes.

6.5.7 Cytochrome P450 Reductase (CPR)

Cytochrome P450 reductases (EC 1.6.2.4) are capable of assisting or facilitating the activity of KO and/or KAH above. Illustrative examples of enzymes include those of *Stevia rebaudiana* (accession no. ABB88839) *Arabidopsis thaliana* (accession no. NP 194183), *Gibberella fujikuroi* (accession no. CAE09055), *Artemisia annua* (accession no. ABC47946.1) and US 2014/0329281 A1, US 2014/0357588 A1, US 2015/0159188, and WO 2016/038095 A2. Nucleic acids encoding these enzymes are useful in the cells and methods provided herein. In certain embodiments, provided herein are cells and methods using a nucleic acid having at least 80%, 85%, 90%, or 95% sequence identity to at least one of these CPR nucleic acids. In certain embodiments, provided herein are cells and methods using a nucleic acid that encodes a polypeptide having at least 80%, 85%, 90%, or 95% sequence identity to at least one of these CPR enzymes.

6.5.8 UDP Glycosyltransferase 74G1 (UGT74G1)

A UGT74G1 is capable of functioning as a uridine 5'-diphospho glucosyl:steviol 19-COOH transferase and as a uridine 5'-diphospho glucosyl:steviol-13-O-glucoside 19-COOH transferase. As shown in FIG. 2B, a UGT74G1 is capable of converting steviol to 19-glycoside. A UGT74G1 is also capable of converting steviolmonoside to rubusoside. A UGT74G1 may be also capable of converting steviolbioside to stevioside. Illustrative examples of enzymes include those of *Stevia rebaudiana* (e.g., those of Richman et al., 2005, Plant J. 41: 56-67 and US 2014/0329281 and WO 2016/038095 A2 and accession no. AAR06920.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT74G1 nucleic acids. In certain embodiments, provided herein are cells and methods using a nucleic acid that encodes a polypeptide having at least 80%, 85%, 90%, or 95% sequence identity to at least one of these UGT74G1 enzymes.

6.5.9 UDP Glycosyltransferase 76G1 (UGT76G1)

A UGT76G1 is capable of transferring a glucose moiety to the C-3' of the C-13-O-glucose of the acceptor molecule, a steviol 1,2 glycoside. Thus, a UGT76G1 is capable of functioning as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. As shown in FIG. 2A, a UGT76G1 is capable of converting steviolbioside to RebB. A UGT76G1 is also capable of converting stevioside to RebA. A UGT76G1 is also capable of converting RebD to RebM. Illustrative examples of enzymes include those of *Stevia rebaudiana* (e.g., those of Richman et al., 2005, Plant J. 41: 56-67 and US 2014/0329281 A1 and WO 2016/038095 A2 and accession no. AAR06912.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT76G1 nucleic acids. In certain embodiments, provided herein are cells and methods using a nucleic acid that encodes a polypeptide having at least 80%, 85%, 90%, or 95% sequence identity to at least one of these UGT76G1 enzymes.

6.5.10 UDP Glycosyltransferase 85C2 (UGT85C2)

A UGT85C2 is capable of functioning as a uridine 5'-diphospho glucosyl:steviol 13-OH transferase, and a uridine 5'-diphospho glucosyl: steviol-19-O-glucoside 13-OH transferase. Thus, as shown in FIG. 2B, a UGT85C2 is capable of converting steviol to steviolmonoside, and is also capable of converting 19-glycoside to rubusoside. Illustrative examples of enzymes include those of *Stevia rebaudiana* (e.g., those of Richman et al., 2005, Plant) 41: 56-67 and US 2014/0329281 A1 and WO 2016/038095 A2 and accession no. AAR06916.1). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT85C2 nucleic acids. In certain embodiments, provided herein are cells and methods using a nucleic acid that encodes a polypeptide having at least 80%, 85%, 90%, or 95% sequence identity to at least one of these UGT85C2 enzymes.

6.5.11 UDP-glycosyltransferase 91D (UGT91D)

A UGT91D is capable of functioning as a uridine 5'-diphosphoglucosyl:steviol-13-0-glucoside transferase, transferring a glucose moiety to the C-2' of the 13-O-glucose of the acceptor molecule, steviol-13-O-glucoside (steviolmonoside) to produce steviobioside. A UGT91D is also capable of functioning as a uridine 5'-diphospho glucosyl: rubusoside transferase, transferring a glucose moiety to the C-2' of the 13-O-glucose of the acceptor molecule, rubusoside, to provide stevioside as shown in FIG. 2B. UGT91D is also capable of transferring a glucose moiety to the C-2' position of the 19-O-glucose of RebA to produce RebD as shown in FIG. 2B. A UGT91D is also referred to as UGT91D2, UGT91D2e, or UGT91D-like3. Illustrative examples of UGT91D enzymes include those of *Stevia rebaudiana* (e.g., those of UGT sequence with accession no. ACE87855.1, US 2014/0329281 A1, WO 2016/038095 A2, and SEQ ID NO:7). Nucleic acids encoding these enzymes are useful in the cells and methods provided herein. In certain embodiments, provided herein are cells and methods using a nucleic acid having at least 80%, 85%, 90%, or 95% sequence identity to at least one of these UGT91D nucleic acids. In certain embodiments, provided herein are cells and methods using a nucleic acid that encodes a polypeptide having at least 80%, 85%, 90%, or 95% sequence identity to at least one of these UGT91D enzymes.

6.5.12 UDP-glycosyltransferase 40087 (UGT40087)

A UGT40087 is capable of transferring a glucose moiety to the C-2' position of the 19-O-glucose of RebA to produce RebD as shown in FIG. 2B. A UGT40087 is also capable of transferring a glucose moiety to the C-2' position of the 19-O-glucose of stevioside to produce RebE. Illustrative examples of UGT40087 are described above in Section 5.2. Any UGT40087 variant described herein can be used in the compositions and methods described herein. Nucleic acids encoding these enzymes are useful in the cells and methods provided herein. In certain embodiments, provided herein are cells and methods using a nucleic acid having at least 80%, 85%, 90%, or 95% sequence identity to at least one of the UGT40087 enzymes. In certain embodiments, provided herein are cells and methods using a nucleic acid that encodes a polypeptide having at least 80%, 85%, 90%, or 95% sequence identity to at least one of these UGT40087 enzymes. In certain embodiments, provided herein are a nucleic acid that encodes a UGT40087 variant described herein.

6.6 MEV Pathway FPP and/or GGPP Production

In some embodiments, a genetically modified host cell provided herein comprises one or more heterologous enzymes of the MEV pathway, useful for the formation of FPP and/or GGPP. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-CoA thiolase, acetoacetyl-CoA synthetase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises one or more heterologous nucleotide sequences encoding more than one enzyme of the MEV pathway. In some embodiments, the host cell comprises one or more heterologous nucleotide sequences encoding two enzymes of the MEV pathway. In some embodiments, the host cell comprises one or more heterologous nucleotide sequences encoding an enzyme that can convert HMG-CoA into mevalonate and an enzyme that can convert mevalonate into mevalonate 5-phosphate.

In some embodiments, the host cell comprises one or more heterologous nucleotide sequences encoding three enzymes of the MEV pathway. In some embodiments, the host cell comprises one or more heterologous nucleotide sequences encoding four enzymes of the MEV pathway. In some embodiments, the host cell comprises one or more heterologous nucleotide sequences encoding five enzymes of the MEV pathway. In some embodiments, the host cell comprises one or more heterologous nucleotide sequences encoding six enzymes of the MEV pathway. In some embodiments, the host cell comprises one or more heterologous nucleotide sequences encoding seven enzymes of the MEV pathway. In some embodiments, the host cell comprises a plurality of heterologous nucleic acids encoding all of the enzymes of the MEV pathway.

In some embodiments, the genetically modified host cell further comprises a heterologous nucleic acid encoding an enzyme that can convert isopentenyl pyrophosphate (IPP) into dimethylallyl pyrophosphate (DMAPP). In some embodiments, the genetically modified host cell further comprises a heterologous nucleic acid encoding an enzyme that can condense IPP and/or DMAPP molecules to form a polyprenyl compound. In some embodiments, the genetically modified host cell further comprise a heterologous nucleic acid encoding an enzyme that can modify IPP or a polyprenyl to form an isoprenoid compound such as farnesene.

6.6.1 Conversion of Acetyl-CoA to Acetoacetyl-CoA

In some embodiments, the genetically modified host cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC 000913 REGION: 2324131.2325315; *Escherichia coli*), (D49362; *Paracoccus denitrificans*), and (L20428; *Saccharomyces cerevisiae*).

Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible.

In host cells comprising acetyl-CoA thiolase and a heterologous ADA and/or phosphotransacetylase (PTA), the reversible reaction catalyzed by acetyl-CoA thiolase, which favors acetoacetyl-CoA thiolysis, may result in a large acetyl-CoA pool. In view of the reversible activity of ADA, this acetyl-CoA pool may in turn drive ADA towards the reverse reaction of converting acetyl-CoA to acetaldehyde, thereby diminishing the benefits provided by ADA towards acetyl-CoA production. Similarly, the activity of PTA is reversible, and thus, a large acetyl-CoA pool may drive PTA towards the reverse reaction of converting acetyl-CoA to acetyl phosphate. Therefore, in some embodiments, in order to provide a strong pull on acetyl-CoA to drive the forward reaction of ADA and PTA, the MEV pathway of the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci USA* 107(25):11265-70 (2010). Representative AACS nucleotide sequences of *Streptomyces* sp. strain CL190 include accession number AB540131.1. Representative AACS protein sequences of *Streptomyces* sp. strain CL190 include accession numbers D7URV0, BAJ10048. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988 (AB212624; BAE78983); *Actinoplanes* sp. A40644 (AB113568; BAD07381); *Streptomyces* sp. C (NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

6.6.2 Conversion of Acetoacetyl-CoA to HMG-CoA

In some embodiments, the host cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC 001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC 002758, Locus tag SAV2546, GeneID 1122571; *Staphylococcus aureus*).

6.6.3 Conversion of HMG-CoA to Mevalonate

In some embodiments, the host cell comprises a heterologous nucleotide sequence encoding an enzyme that can convert HMG-CoA into mevalonate, e.g., a HMG-CoA reductase. In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., Journal of Bacteriology 186 (7): 1927-1932 (2004). Co-factor specificities for select class II HMG-CoA reductases are provided below.

TABLE 1

| Co-factor specificities for select class II HMG-CoA reductases | | | |
|---|---|---|---|
| Source | Coenzyme specificity | $K_m^{NADPH}$ (μM) | $K_m^{NADPH}$ (μM) |
| P. mevalonii | NADH | | 80 |
| A. fulgidus | NAD(P)H | 500 | 160 |
| S. aureus | NAD(P)H | 70 | 100 |
| E. faecalis | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii*, *A. fulgidus* or *S. aureus*. In particular embodiments, the HMG-CoA reductase is capable of only utilizing NADH as a cofactor, e.g., HMG-CoA reductase from *P. mevalonii*, *S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described. See Beach and Rodwell, *J. Bacteriol.* 171:2994-3001 (1989). Representative mvaA nucleotide sequences of *Pseudomonas mevalonii* include accession number M24015. Representative HMG-CoA reductase protein sequences of *Pseudomonas mevalonii* include accession numbers AAA25837, P13702, MVAA_PSEMV.

In some embodiments, the NADH-using HMG-CoA reductase is from *Silicibacter pomeroyi*. Representative HMG-CoA reductase nucleotide sequences of *Silicibacter pomeroyi* include accession number NC_006569.1. Representative HMG-CoA reductase protein sequences of *Silicibacter pomeroyi* include accession number YP_164994.

In some embodiments, the NADH-using HMG-CoA reductase is from *Delftia acidovorans*. A representative HMG-CoA reductase nucleotide sequences of *Delftia acidovorans* includes NC_010002 REGION: complement (319980 . . . 321269). Representative HMG-CoA reductase protein sequences ofDelftia acidovorans include accession number YP_001561318.

In some embodiments, the NADH-using HMG-CoA reductases is from Solanum tuberosum (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol,* 171(12):6468-6472 (1989); Beach et al., *J. Bacteriol.* 171: 2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase. Illustrative examples of nucleotide sequences encoding an NADPH-using HMG-CoA reductase include, but are not limited to: (NM_206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

6.6.4 Conversion of Mevalonate to Mevalonate-5-Phosphate

In some embodiments, the host cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

6.6.5 Conversion of Mevalonate-5-Phosphate to Mevalonate-5-Pyrophosphate

In some embodiments, the host cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; Hevea *brasiliensis*), (NM 006556; *Homo sapiens*), and (NC 001145. complement 712315.713670; *Saccharomyces cerevisiae*).

6.6.6 Conversion of Mevalonate-5-Pyrophosphate to IPP

In some embodiments, the host cell comprises a heterologous nucleotide sequence encoding an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

6.6.7 Conversion of IPP to DMAPP

In some embodiments, the host cell further comprises a heterologous nucleotide sequence encoding an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to:

(NC_000913, 3031087.3031635; *Escherichia coli*), and (AF082326; *Haematococcus pluvialis*).

6.6.8 Polyprenyl Synthases

In some embodiments, the host cell further comprises a heterologous nucleotide sequence encoding a polyprenyl synthase that can condense IPP and/or DMAPP molecules to form polyprenyl compounds containing more than five carbons.

In some embodiments, the host cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; Mentha x piperita), (PZE431697, Locus CAD24425; *Paracoccus zeaxanthinifaciens*), (AY866498; *Picrorhiza kurrooa*), (AY351862; *Vitiso vinifera*), and (AF203881, Locus AAF12843; *Zymomonas mobilis*).

In some embodiments, the host cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locs AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar *Copenhageni* str. *Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa* Temecula1).

In some embodiments, the host cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides f. lusitanicus*), (AB016044; *Mus musculus*), (AABX01000298, Locus NCU01427; *Neurospora crassa*), (NCU02940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

While examples of the enzymes of the mevalonate pathway are described above, in certain embodiments, enzymes of the DXP pathway can be used as an alternative or additional pathway to produce DMAPP and IPP in the host cells, compositions and methods described herein. Enzymes and nucleic acids encoding the enzymes of the DXP pathway are well-known and characterized in the art. WO 2012/135591 A2.

6.7 Methods of Producing Steviol Glycosides

In another aspect, provided herein is a method for the production of a steviol glycoside by converting one steviol glycoside to another steviol glycoside using any UDP-glycosyltransferases described herein (e.g., UGT40087 or any variant UGT40087). In certain embodiments, provided herein is a method for the production of RebD comprising converting RebA to RebD using any of the UDP-glycosyltransferases described herein, capable of converting RebA to RebD. In certain embodiments, provided herein is a method for the production of RebM comprising: converting RebA to RebD using any of the UDP-glycosyltransferases described herein, capable of converting RebA to RebD; and converting RebD to RebM using a UDP-glycosyltransferase capable of converting RebD to RebM.

In certain embodiments, a steviol glycoside (e.g., RebA or RebD) or a composition comprising a steviol glycoside can be contacted, under suitable conditions, with any of the UDP-glycosyltransferase described herein and a UDP-sugar to produce a desired steviol glycoside (e.g., RebM). Such methods can be performed in vivo or in vitro. Exemplary UDP-sugars include UDP-glycose, UDP-xylose or UDP-rhamnose.

In another aspect, provided herein is a method for the production of a steviol glycoside, the method comprising the steps of: (a) culturing a population of any of the genetically modified host cells described herein that are capable of producing a steviol glycoside in a medium with a carbon source under conditions suitable for making the steviol glycoside compound; and (b) recovering said steviol glycoside compound from the medium.

In some embodiments, the genetically modified host cell produces an increased amount of the steviol glycoside compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a steviol glycoside that is greater than about 10 grams per liter of fermentation medium. In some such embodiments, the steviol glycoside is produced in an amount from about 10 to about 50 grams per liter of cell culture, more than about 15 grams per liter of cell culture, more than about 20 grams per liter of cell culture, more than about 25 grams per liter of cell culture, more than about 30 grams per liter of cell culture, more than about 35 grams per liter of cell culture, more than about 40 grams per liter of cell culture, more than about 45 grams per liter of cell culture, or more than about 50 grams per liter of cell culture.

In some embodiments, the host cell produces an elevated level of a steviol glycoside that is greater than about 50 milligrams per gram of dry cell weight. In some such embodiments, the steviol glycoside is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by a parent cell, on a per unit volume of cell culture basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit volume of cell culture per unit time basis.

In some embodiments, the host cell produces an elevated level of a steviol glycoside that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of steviol glycoside produced by the parent cell, on a per unit dry cell weight per unit time basis.

In most embodiments, the production of the elevated level of steviol glycoside by the host cell is controlled by a repressing compound. Such a host cell can be manipulated with ease in the presence of the repressing compound. The repressing compound is then removed to induce the production of the elevated level of steviol glycoside by the host cell.In other embodiments, production of the elevated level of steviol glycoside by the host cell is inducible by changing culture conditions, such as, for example, the growth temperature, media constituents, and the like.

6.8 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing steviol glycosides provided herein may be performed in a suitable culture medium (e.g., with or without pantothenate supplementation) in a suitable container, including but not limited to a cell culture plate, a flask, or a fermenter. Further, the methods can be performed at any scale of fermentation known in the art to support industrial production of microbial products. Any suitable fermenter may be used including a stirred tank fermenter, an airlift fermenter, a bubble fermenter, or any combination thereof. In particular embodiments utilizing *Saccharomyces cerevisiae* as the host cell, strains can be grown in a fermenter as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing a steviol glycoside can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, mannose, fructose, xylose, ribose, and combinations thereof. Non-limiting examples of suitable disaccharides include sucrose, lactose, maltose, galactose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, fermentation cultures are run with a carbon source, such as glucose, being added at levels to achieve the desired level of growth and biomass, but at undetectable levels (with detection limits being about <0.1 g/1). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or steviol glycoside production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of steviol glycoside. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermenter and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

Other suitable fermentation medium and methods are described in, e.g., WO 2016/196321.

6.9 Fermentation Compositions

In another aspect, provided herein are fermentation compositions comprising a genetically modified host cell described herein and steviol glycosides produced from genetically modified host cell. The fermentation compositions may further comprise a medium. In certain embodiments, the fermentation compositions comprise a genetically modified host cell, and further comprise RebA, RebD, and RebM. In certain embodiments, the fermentation compositions provided herein comprise RebM as a major component of the steviol glycosides produced from the genetically modified host cell. In certain embodiments, the fermentation compositions comprise RebA, RebD, and RebM at a ratio of at least 1:7:50. In other embodiments, the fermentation compositions comprise (RebA+RebD) and RebM at a ratio of at least 8:50. In certain embodiments, the fermentation compositions comprise RebA, RebD, and RebM at a ratio of at least 1:7:50 to 1:100:1000. In other embodiments, the fermentation compositions comprise (RebA+RebD) and RebM at a ratio of at least 8:50 to 101:1000. In certain embodiments, the fermentation compositions comprise a ratio of at least 1:7:50 to 1:200:2000. In other embodiments, the fermentation compositions comprise (RebA+RebD) and RebM at a ratio of at least 8:50 to 201:2000. In certain embodiments, the ratio of RebA, RebD, and RebM are based on the total content of these three steviol glycosides that are associated with the genetically modified host cell and the medium. In certain embodiments, the ratio of RebA, RebD, and RebM are based on the total content of these three steviol glycosides in the medium. In certain embodiments, the ratio of RebA, RebD, and RebM are based on the total content of these three steviol glycosides that are associated with the genetically modified host cell.

In other embodiments, the fermentation compositions comprise a genetically modified host cell, and further comprise RebA and RebM. In certain embodiments, the fermentation compositions comprise RebA and RebM at a RebA:RebM ratio of at least 1:50. In certain embodiments, the fermentation compositions comprise RebA and RebM at a RebA:RebM ratio of at least 1:50 to 1:1000. In certain embodiments, the fermentation compositions comprise RebA and RebM at a RebA:RebM ratio of at least 1:50 to 1:2000. In certain embodiments, the ratio of RebA and RebM are based on the total content of these two steviol glycosides that are associated with the genetically modified host cell and the medium. In certain embodiments, the ratio of RebA and RebM are based on the total content of these two steviol glycosides in the medium. In certain embodiments, the ratio of RebA and RebM are based on the total content of these two steviol glycosides that are associated with the genetically modified host cell.

In a further embodiment, the fermentation compositions comprise a genetically modified host cell, and further comprise RebD and RebM. In certain embodiments, the fermentation compositions comprise RebD and RebM at a RebD:RebM ratio of at least 7:50. In certain embodiments, the fermentation compositions comprise RebD and RebM at a RebD:RebM ratio of at least 7:50 to 7:100. In certain embodiments, the fermentation compositions comprise RebD and RebM at a RebD:RebM ratio of at least 7:50 to 7:200. In certain embodiments, the ratio of RebA, RebD, and RebM are based on the total content of these two steviol glycosides that are associated with the genetically modified host cell and the medium. In certain embodiments, the ratio of RebD and RebM are based on the total content of these two steviol glycosides in the medium. In certain embodiments, the ratio of RebD and RebM are based on the total content of these two steviol glycosides that are associated with the genetically modified host cell.

In certain embodiments, the fermentation compositions provided herein contain RebM2 at an undetectable level. In certain embodiments, the fermentation compositions provided herein contain non-naturally occurring steviol glycosides at an undetectable level. In certain embodiments, the fermentation compositions provided herein, when subjected to GC-chromatography, does not produce a "steviol+2 glucose" peak between a RebA peak and a RebB at a detectable level 6.10 Recovery of Steviol Glycosides Once the steviol glycoside is produced by the host cell, it may be recovered or isolated for subsequent use using any suitable separation and purification methods, including any suitable steviol glycoside separation and purification methods, known in the art. Auitable methods are described in, e.g., U.S. Pat. Nos. 7,838,044 and 8,981,081; U.S. patent application Ser. Nos. 14/603,941, 14/033,563, 14/362,275, 14/613,615, 14/615,888; PCT Application Nos. PCT/US12/070562, and PCT/US14/031129. The contents of these documents are included herein by reference in their entirety. In some embodiments, an aqueous phase comprising the steviol glycoside is separated from the fermentation by centrifugation. In other embodiments, an aqueous phase comprising the steviol glycoside separates from the fermentation spontaneously. In other embodiments, an aqueous phase comprising the steviol glycoside is separated from the fermentation by adding a demulsifier and/or a nucleating agent into the fermentation reaction. Illustrative examples of demulsifiers include flocculants and coagulants. Illustrative examples of nucleating agents include droplets of the steviol glycoside itself and organic solvents such as dodecane, isopropyl myristrate, and methyl oleate.

The steviol glycoside produced in these cells may be present in the culture supernatant and/or associated with the host cells. In embodiments where the steviol glycoside is associated with the host cell, the recovery of the steviol glycoside may comprise a method of permeabilizing or lysing the cells. Alternatively or simultaneously, the steviol glycoside in the culture medium can be recovered using a recovery process including, but not limited to, chromatography, adsorption chromatography, extraction, solvent extraction, membrane separation, electrodialysis, reverse osmosis, distillation, chemical derivatization and crystallization.

In some embodiments, the steviol glycoside is separated from other products that may be present in the aqueous phase. In some embodiments, separation is achieved using adsorption, distillation, gas-liquid extraction (stripping), liquid-liquid extraction (solvent extraction), vacuum extraction, evaporation, ultrafiltration, and standard chromatographic techniques. Other suitable fermentation medium and methods are described in, e.g., U.S. Patent Application Publication Nos. 2016/0185813, 2017/0190728, WO/2017/093895. Other suitable methods are described in, e.g., U.S. Pat. Nos. 7,838,044 and 8,981,081; U.S. patent application Ser. Nos. 14/603,941, 14/033,563, 14/362,275, 14/613,615 and 14/615,888; PCT Application Nos. PCT/US12/070562, and PCT/US14/031129. The contents of these documents are included herein by reference in their entirety In certain embodiments, the recovered steviol glycoside(s) can be used in a variety of end products. For example, a purified RebM compound or a composition comprising RebM can be used in any consumable products, such as food products, pharmaceutical products, dietary supplements, or nutritional supplements. In particular embodiments, a consumable comprising RebM is made by the process of culturing a population of the genetically modified host cells of any of the preceding claims in a medium with a carbon source under conditions suitable for making RebM; and recovering said RebM compound from the medium.

Sweetener compositions, as used herein, mean compositions that contain at least one sweet component in combination with at least one other substance, such as, for example, another sweetener or an additive.

Sweetenable compositions, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Sweetened compositions, as used herein, mean substances that contain both a sweetenable composition and a sweetener or sweetener composition.

For example, a beverage with no sweetener component is a type of sweetenable composition. A sweetener composition comprising RebM produced by method of present invention, and erythritol can be added to the un-sweetened beverage, thereby providing a sweetened beverage. The sweetened beverage is a type of sweetened composition. Suitable sweetener compositions, sweetened compositions and methods of making thereof are described in, e.g., PCT application PCT/US12/070562, the contents of which is included herein by reference in its entirety.

In one embodiment, a sweetener comprising RebM is made by the process of culturing a population of the genetically modified host cells of any of the preceding claims in a medium with a carbon source under conditions suitable for making RebM; and recovering said RebM compound from the medium. In another embodiment, a sweetener composition comprising at least one other substance and RebM is made by the process of culturing a population of the genetically modified host cells of any of the preceding claims in a medium with a carbon source under conditions suitable for making RebM; and recovering said RebM compound from the medium. In another embodiment, a sweetened composition comprising RebM is made by the process of culturing a population of the genetically modified host cells of any of the preceding claims in a medium with a carbon source under conditions suitable for making RebM; and recovering said RebM compound from the medium. One embodiment comprises a method of making a sweetener composition comprising combining at least one other substance with RebM made by the process of culturing a population of the genetically modified host cells of any of the preceding claims in a medium with a carbon source under conditions suitable for making RebM; and recovering said RebM compound from the medium. Another embodiment comprises a method of making a sweetened composition comprising combining at least one sweetenable composition with RebM made by the process of culturing a population of the genetically modified host cells of any of the preceding claims in a medium with a carbon source under conditions suitable for making RebM; and recovering said RebM compound from the medium.

6.11 Methods of Making Genetically Modified Cells

Also provided herein are methods for producing a host cell that is genetically engineered to comprise one or more of the modifications described above, e.g., one or more heterologous nucleic acids encoding UGT40087, and/or biosynthetic pathway enzymes, e.g., for a steviol glycoside compound. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is integrated into the chromosome of the host cell.

Nucleic acids encoding proteins can be introduced into the host cell by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The activity of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the activity of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, KAN$^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias." Codon optimization for other host cells can be readily determined using codon usage tables or can be performed using commercially available software, such as CodonOp (www.idtdna.com/CodonOptfrom) from Integrated DNA Technologies.

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum, Kluyveromyces* spp., including *K. thermotolerans, K. lactis*, and *K. marxianus, Pichia* spp., *Hansenula* spp., including *H. polymorpha, Candida* spp., *Trichosporon* spp., *Yamadazyma* spp., including *Y.* spp. *stipitis, Torulaspora pretoriensis, Issatchenkia orientalis,* *Schizosaccharomyces* spp., including *S. pombe, Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia coli, Zymomonas mobilis, Staphylococcus aureus, Bacillus* spp., *Clostridium* spp., *Corynebacterium* spp., *Pseudomonas* spp., *Lactococcus* spp., *Enterobacter* spp., and *Salmonella* spp.

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous UDP glycosyltransferases, PTA, or any biosynthetic pathway genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology*, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

7. EXAMPLES

Example 1: Generation of a Base Yeast Strain Capable of High Flux to Farnesylpyrophosphate (FPP) and the Isoprenoid Farnesene A farnesene production strain was created from a wild-type *Saccharomyces cerevisiae* strain (CEN.PK2) by expressing the genes of the mevalonate pathway (FIG. 1C) under the control of GAL1 or GAL10 promoters. This strain comprised the following chromosomally integrated mevalonate pathway genes from *S. cerevisiae*: acetyl-CoA thiolase, HMG-CoA synthase, HMG-CoA reductase, mevalonate kinase, phosphomevalonate kinase, mevalonate pyrophosphate decarboxylase, and IPP:DMAPP isomerase. All genes described herein were codon optimized using publicly available or other suitable algorithms. In addition, the strain contained six copies of farnesene synthase from *Artemisinin annua*, also under the control of either GAL1 or GAL10 promoters. The strain also contained a deletion of the GAL80 gene and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601). Lastly the ERGS gene, encoding squalene synthase, is downregulated by replacing the native promoter with promoter of the yeast gene MET3 (Westfall et al PNAS 2012).

Example 2. Generation of a Base Yeast Strain Capable of High Flux to RebA

FIG. 2A shows an exemplary biosynthetic pathway from FPP to the steviol. FIG. 2B shows an exemplary biosynthetic pathway from steviol to glycoside RebM. To convert the farnesene base strain described above to have high flux to the C-20 isoprenoid kaurene, six copies of a geranylgeranylpyrophosphate synthase (GGPPS) were integrated into the genome, followed by four copies each of a copalyl-diphosphate synthase and kaurene synthase. At this point the six copies of farnesene synthase were removed from the strain. Once the new strain was confirmed to make ent-kaurene, the remaining genes for converting ent-kaurene to RebA were inserted into the genome. Table 4 lists all genes and promoters used to convert FPP to RebA. Each gene after kaurene synthase was integrated with a single copy, except for the Sr.KAH enzyme which had two copies (Table 4). The strain containing all genes described in Table 1 primarily produced RebA. The enzyme UGT91D_like3 has some low activity to convert RebA to Rebaudioside D (RebD). We measured that a single copy of UGT91D_like3 is able to convert approximately (3%) of the RebA in the strain to RebD in vivo in the yeast strain described above (FIG. 3 and Table 5). UGT76G1 then can convert RebD to the final product RebM.

Example 3. Generation of a Strain to Screen Novel UDP-Glycosyltransferase (UGT) Enzymes to Convert RebA to RebD To make a screening strain to rapidly screen for RebA to RebD conversion in vivo, a landing pad was inserted into the RebA strain described above. The landing pad consisted of 500 bp of locus-targeting DNA sequences on either end of the construct to the genomic region downstream of the ALG1 open reading frame (FIG. 4). Internally, the landing pad contained a PGAL1 promoter and a yeast terminator flanking an endonuclease recognition site (F-CphI).

Example 4. Screening for UGT Genes that Convert RebA to RebD with High Efficiency In Vivo Over a hundred UGT enzymes obtained from Genbank, were codon optimized for optimal expression in S. cerevisiae and synthesized with 60 bp of sequence homologous to the PGAL1 and yeast terminator flanking the F-CphI sequences in the landing pad described above. Each synthesized UGT gene was tested individually, with a single copy, for the ability to convert RebA to RebD in vivo in the yeast strain described above. Yeast were transformed with UGT donor DNA and a plasmid containing the endonuclease F-CphI to cut the DNA in the landing pad. Correct integrations were verified by colony PCR using a reverse primer internal to the specific UGT gene in each transformation and a universal forward primer at the end of the ALG1 ORF.

Example 5. Yeast Transformation Methods

Each DNA construct was integrated into Saccharomyces cerevisiae (CEN.PK2) with standard molecular biology techniques in an optimized lithium acetate (LiAc) transformation. Briefly, cells were grown overnight in yeast extract peptone dextrose (YPD) media at 30° C. with shaking (200 rpm), diluted to an $OD_{600}$ of 0.1 in 100 mL YPD, and grown to an $OD_{600}$ of 0.6-0.8. For each transformation, 5 mL of culture was harvested by centrifugation, washed in 5 mL of sterile water, spun down again, resuspended in 1 mL of 100 mM LiAc, and transferred to a microcentrifuge tube. Cells were spun down (13,000×g) for 30 seconds, the supernatant was removed, and the cells were resuspended in a transformation mix consisting of 240 µL 50% PEG, 36 µL 1 M LiAc, 10 µL boiled salmon sperm DNA, and 74 µL of donor DNA. For transformations that required expression of the endonuclease F-CphI, the donor DNA included a plasmid carrying the F-CphI gene expressed under the yeast TDH3 promoter for expression. This will cut the F-CphI endonuclease recognition site in the landing pad to facilitate integration of the UGT gene. Following a heat shock at 42° C. for 40 minutes, cells were recovered overnight in YPD media before plating on selective media. DNA integration was confirmed by colony PCR with primers specific to the integrations.

Example 6. Yeast Culturing Conditions

Yeast colonies verified to contain the expected UGT gene were picked into 96-well microtiter plates containing Bird Seed Media (BSM, originally described by van Hoek et al., Biotechnology and Bioengineering 68(5), 2000, pp. 517-523) with 20 g/L sucrose and 37.5 g/L ammonium sulfate. Cells were cultured at 30° C. in a high capacity microtiter plate incubator shaking at 1000 rpm and 80% humidity for 3 days until the cultures reached carbon exhaustion. The growth-saturated cultures were subcultured into fresh plates containing BSM with 40 g/L sucrose and 150 g/L ammonium sulfate by taking 14.4 µl from the saturated cultures and diluting into 360 µl of fresh media. Cells in the production media were cultured at 30° C. in a high capacity microtiter plate shaker at 1000 rpm and 80% humidity for an additional 3 days prior to extraction and analysis. Upon completion the whole cell broth is diluted with 360 uL of 100% ethanol, sealed with a foil seal, and shaken at 1250 rpm for 30 min to extract the steviol glycosides. 490 uL of 50:50 ethanol:water is added to a new 1.1 mL assay plate and 10 uL of the culture/ethanol mixture is added to the assay plate. The mixture is centrifuged to pellet any solids, and 400 uL of the solution is transferred to a new 1.1 mL plate and assayed by LC-MS.

Example 7. Analytical Methods

Samples were analyzed by LC-MS mass spectrometer (AB QTrap 4000) using a Sigma Ascentis Express Peptide ES-C18 (5 cm, 2.1 mm, 2.7 um; part #53301-U) with the following gradient (Mobile phase A: 0.1% Formic Acid in H2O; Mobile phase B: 0.1% Formic acid in Acetonitrile):

TABLE 2

| | Time (min) | % B |
|---|---|---|
| 1 | 0 | 25 |
| 2 | 2.50 | 25 |
| 3 | 10.00 | 60 |
| 4 | 10.50 | 100 |
| 5 | 12.50 | 100 |
| 6 | 12.51 | 25 |

The mass spectrometer was operated in negative ion multiple reaction monitoring mode. Each rebaudioside isomer was identified by retention time, determined from an authentic standard, and MRM transition:

TABLE 3

| RT (min) | Compound | Q1 Mass (Da) | Q3 Mass (Da) |
|---|---|---|---|
| 10.5 | Steviol | 317.328 | 317.300 |
| 8.2 | Steviolmonoside | 479.354 | 317.200 |
| 7.9 | 19-glycoside | 479.369 | 317.100 |
| 7.4 | Steviolbioside | 641.451 | 479.300 |
| 6.9 | Rubusoside | 641.491 | 479.400 |
| 7.3 | RebB | 803.612 | 641.500 |
| 6.2 | Stevioside | 803.550 | 641.400 |
| 3.3 | RebE | 965.441 | 479.400 |
| 6.2 | RebA | 965.441 | 803.700 |
| 3.8 | RebD | 1127.140 | 803.500 |
| 4.5 | RebM | 1289.540 | 803.400 |
| 2.4 | RebM2 | 1289.540 | 641.400 |

The peak areas from a chromatogram from a mass spectrometer were used to generate the calibration curve. The molar ratio of relevant compounds (i.e., RebA, RebD, RebM) were determined by quantifying the amount in moles of each compound through external calibration using an authentic standard, and then taking the appropriate ratios.

NMR analysis was performed to confirm that RebM was produced from the genetically modified strains. After fermentation, strains were removed from the fermentation broth. Steviol glycosides were purified from the remaining liquid medium. Any suitable methods for NMR analysis can be used including those described in, e.g., WO/2017/093895 and WO/2016/028899.

Example 8. UGT Enzymes Found to Have High Activity to Convert RebA to RebD

Six UGT enzymes were found to have high activity to convert RebA to RebD (FIG. 3). The performance of these enzymes were benchmarked against two other UGT enzymes described in the literature, Os_UGT_91C1 (i.e., EUGT11 described in WO 2013/022989 A2) and Sl_UGT_101249881 (i.e., UGTSL2 in WO2014/193888 A1) as also performing the conversion of RebA to RebD.

Table 5 lists the median ratio of [micromoles of Reb (D+M)/micromoles of (A+D+M)]; RebA, RebD, and RebM were measured in in vivo as described above. This ratio is a measure of the efficiency of RebA to RebD conversion. The sum of the uM of [Reb (A+D+M)] measures the total RebA that was ever made in the cell. The sum of the uM of [Reb (D+M)] measures the total RebD that was ever made in the cell. FIG. 5 a-i show the chromatograms of RebE, RebA, RebD, RebM, and RebM2 for all UGT genes in FIG. 3 and Table 2. RebM2 is an isomer of RebM with a single wrong glucose linkage. RebM2 has Glcβ(1-2)[Glcβ (1-6)]Glcβ1-at the 19 carbon position (COOH) instead of instead of the Glcβ (1-2)[Glcβ (1-3)]Glcβ1-for RebM.

Using the NMR methods described in Example 7, the sample product generated from the strain comprising UGT40087 was compared against a standard RebM by 1D and 2D NMR spectroscopy. Overlay of 1D and 2D NMR spectra recorded in methanol and pyridine confirmed that both compounds are identical. Detailed interpretation of 2D NMR data and comparison with data published in the literature confirmed that both samples were RebM.

In a fermentation vessel either 0.5 or 2.0 liters, UGT40087, when expressed in a different strain background, produced RebA, RebD, and RebM at a ratio of about RebA:RebD:RebM of about 1:7:50.

TABLE 4

Genes, promoters, and amino acid sequences of the enzymes used to convert FPP to RebA.

| Enzyme name | Accession number or sequence ID | Promoter |
|---|---|---|
| Btrispora.GGPPS | AFC92798.1 | PGAL1 |
| ent-CDPS_Os | Q5MQ85.1[1] | PGAL1 |
| KS_Pg | ADB55711.1 | PGAL1 |
| Sr.KO | AAQ63464.1 | PGAL1 |
| Sr.KAH | SEQ ID: 10 | PGAL1 |
| Aa.CPR | ABC47946.1 | PGAL3 |
| UGT85C2 | AAR06916.1 | PGAL1 |
| UGT74G1 | AAR06920.1 | PGAL10 |
| UGT91D_like3 | SEQ ID NO: 7 | PGAL1 |
| UGT76G1 | AAR06912.1 | PGAL10 |

[1] First 65 amino acids removed and replaced with methionine

TABLE 5

Median ratio of RebA to RebD conversion of different UGT enzymes, with protein accession number or sequence ID

| UGT name | Median conversion ratio | Protein Accession number or sequence ID | SEQ ID NO. | Organism | % identity to UGT40087 (BLASTP) |
|---|---|---|---|---|---|
| UGT40087 | 0.98 | XP_004982059.1 | 1 | Setaria italica | 100% |
| Ob_UGT91B1_like | 0.97 | XP_006650455.1 | 6 | Oryza brachyantha | 53% |
| Hv_UGT_V1 | 0.87 | BAJ94055.1 | 4 | Hordeum vulgare subsp. vulgare | 53% |
| Sl_UGT_101249881 | 0.70 | XP_004250485.1 | 9 | Solanum lycopersicum | 28% |
| Sr.UGT_g252778 | 0.60 | Sequence ID 3 | 2 | Stevia Rebaudiana | 39% |
| Os_UGT_91C1 | 0.53 | XP_015629141.1 | 8 | Oryza sativa | 54% |
| Bd_UGT10840 | 0.47 | XP_003560669.1 | 3 | Brachypodium distachyon | 54% |
| Bd_UGT10850 | 0.45 | XP_010230871.1 | 5 | Brachypodium distachyon | 51% |
| UGT91D_like3 | 0.03 | ACE87855.1 | 7 | Stevia Rebaudiana | 36% |

Example 9: Specificity of Enzymes in Table 5 that Convert RebA to RebD

The enzymes listed in Table 5 are able to catalyze the conversion of RebA to RebD by the addition of a glucose sugar onto the C-2' position of the 19-O-glucose of RebA through the formation of a beta-1,2-linked glycosidic bond. In certain embodiments, it is desirable for the biotechnological production of RebM in a heterologous host to produce RebM (1) at high purity and (2) without producing any "non-natural" steviol glycosides. Any product sold into the market will likely require extremely high purity to ensure the best flavor profile and meet multiple human food regulatory standards. The presence of steviol glycosides other than RebM will likely increase the cost of downstream processing to obtain highly pure RebM. If there are significant amounts of non-RebM steviol glycosides, it could potentially compromise the final purity of the RebM product. In certain embodiments, it could be advantageous that the heterologous enzymes do not produce any "non-natural" steviol glycosides. A "non-natural" steviol glycoside is defined here as any steviol glycoside that is not known to occur naturally in the plant Stevia rebaudiana.

For the reasons described above, all enzymes listed in Table 5 were examined for their impurity profile, to determine if they made any unexpected or non-natural steviol glycosides that are not shown in FIG. 2B. Chromatographic traces for the longer retention time for all enzymes listed in Table 2 were further analyzed. Of all the enzymes with conversion efficiencies above 50%, the only enzymes that did not make unexpected products were UGT40087 and Os_UGT_91C1 (EUGT11). As expected, UGT91D_like3 did not produce unexpected peaks in the chromatogram.

Among enzymes with conversion efficiencies above 50%, the chromatographic traces of these enzymes produced one or more unexpected peaks which are associated with not naturally occurring glycoside. For example, the chromatographic trace of Ob_UGT91B1_like produced an unexpected peak (steviol+2 glucose) between the RebA peak and the RebB peak at retention time of about 6.61 minutes. The intensity of the unexpected peak of Ob_UGT91B1_like was at least 31 times greater than that of the RebA peak. See FIG. 9c. The unexpected peak (steviol+2 glucose) is not present in the chromatographic trace from a parent control strain (with UGT74G1, UGT85C2, UGT76G1, and UGT91D_like3) or from a strain comprising UGT40087. See FIGS. 9b and 9c. In another example, the chromatographic trace of Hv_UGT_V1 produced an unexpected peak (steviol+2 glucose) between the RebA peak and the RebB peak at retention time of about 6.61 minutes. The intensity of the unexpected peak of Hv_UGT_V1 was 0.6 factor lower than that of the RebA peak. In another example, the chromatographic trace of Sl_UGT_101249881 produced an unexpected peak (steviol+2 glucose) between the RebA peak and the RebB peak at retention time of about 6.67 minutes. The intensity of the unexpected peak of Sl_UGT_101249881 was about 1.11 times greater than that of the RebA peak. In another example, the chromatographic trace of Sr.UGT_g252778 produced an unexpected peak (steviol+2 glucose) between the RebA peak and RebB peak at retention time of about 6.67 minutes. The intensity of the unexpected peak of Sr.UGT_g252778 was about 0.96 factor lower than that of the RebA peak. Some of these enzymes also produced additional unexpected peaks. The chromatographic traces for Hv_UGT_V1, Sl_UGT_101249881, and Sr.UGT_g252778 are omitted.

These results indicate that compared to the two enzymes UGT40087 and Os_UGT_91C1 (EUGT11), the other three enzymes with greater than 50% A to D conversion efficiency (i.e., Hv_UGTV1, Sl_UGT_101249881, and Sr.UGT_g252778) may catalyze additional reactions, potentially producing steviol glycosides not normally made in the pathway to RebM in the plant Stevia Rebaudiana.

TABLE 6

UGT enzymes specificity.

| UGT name | Unexpected steviol glycoside detected in chromatogram | Median conversion ratio |
|---|---|---|
| UGT40087 | No | 0.98 |
| Ob_UGT91B1_like | Yes | 0.97 |
| Hv_UGT_V1 | Yes | 0.87 |
| Sl_UGT_101249881 (SL2) | Yes | 0.70 |
| Sr.UGT_g252778 | Yes | 0.60 |
| Os_UGT_91C1 (EUGT11) | No | 0.53 |
| Bd_UGT10840 | No | 0.47 |
| Bd_UGT10850 | No | 0.45 |
| UGT91D_like3 | No (control) | 0.03 |

Figure 5A:
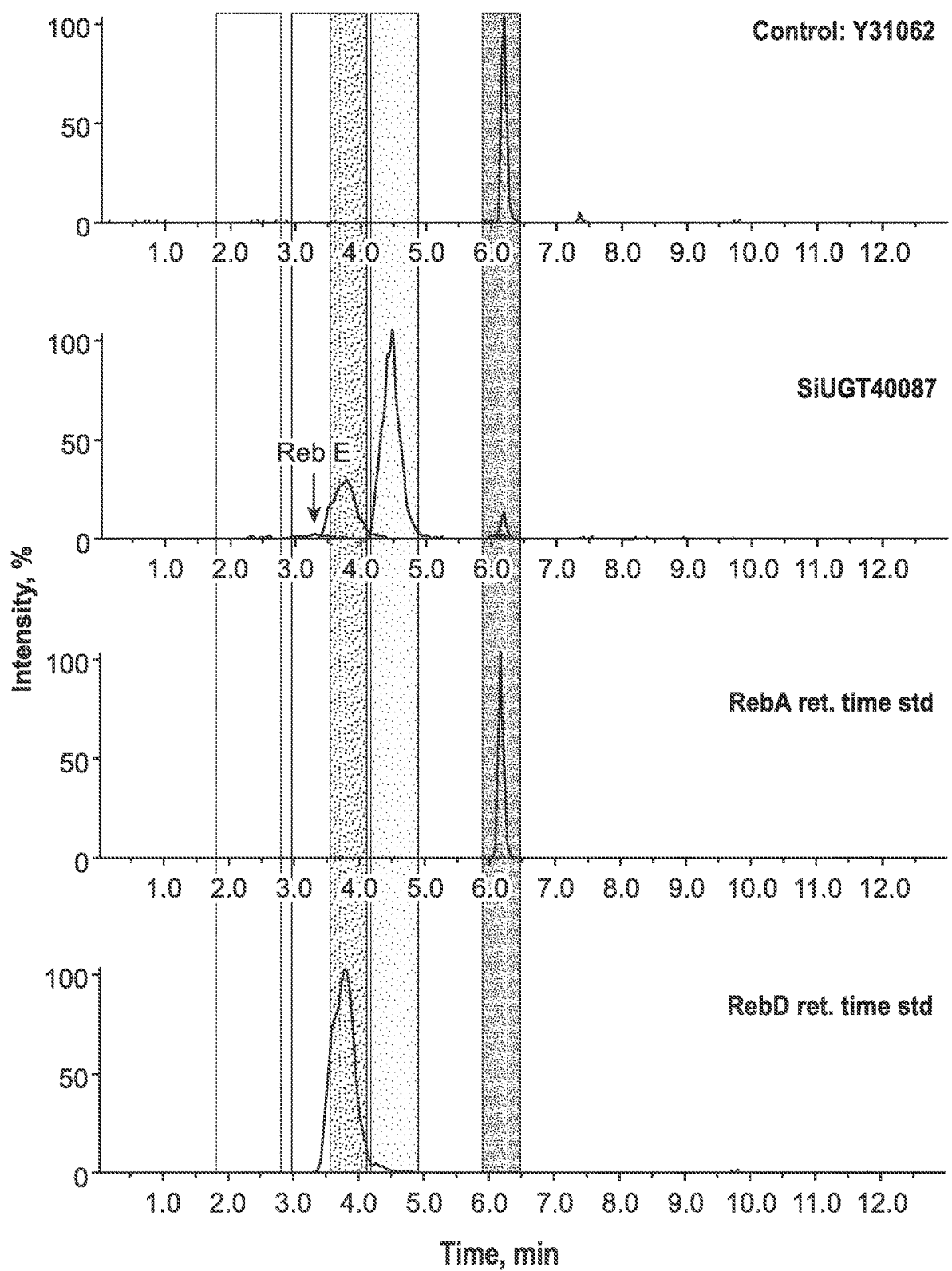
Figure 5A:
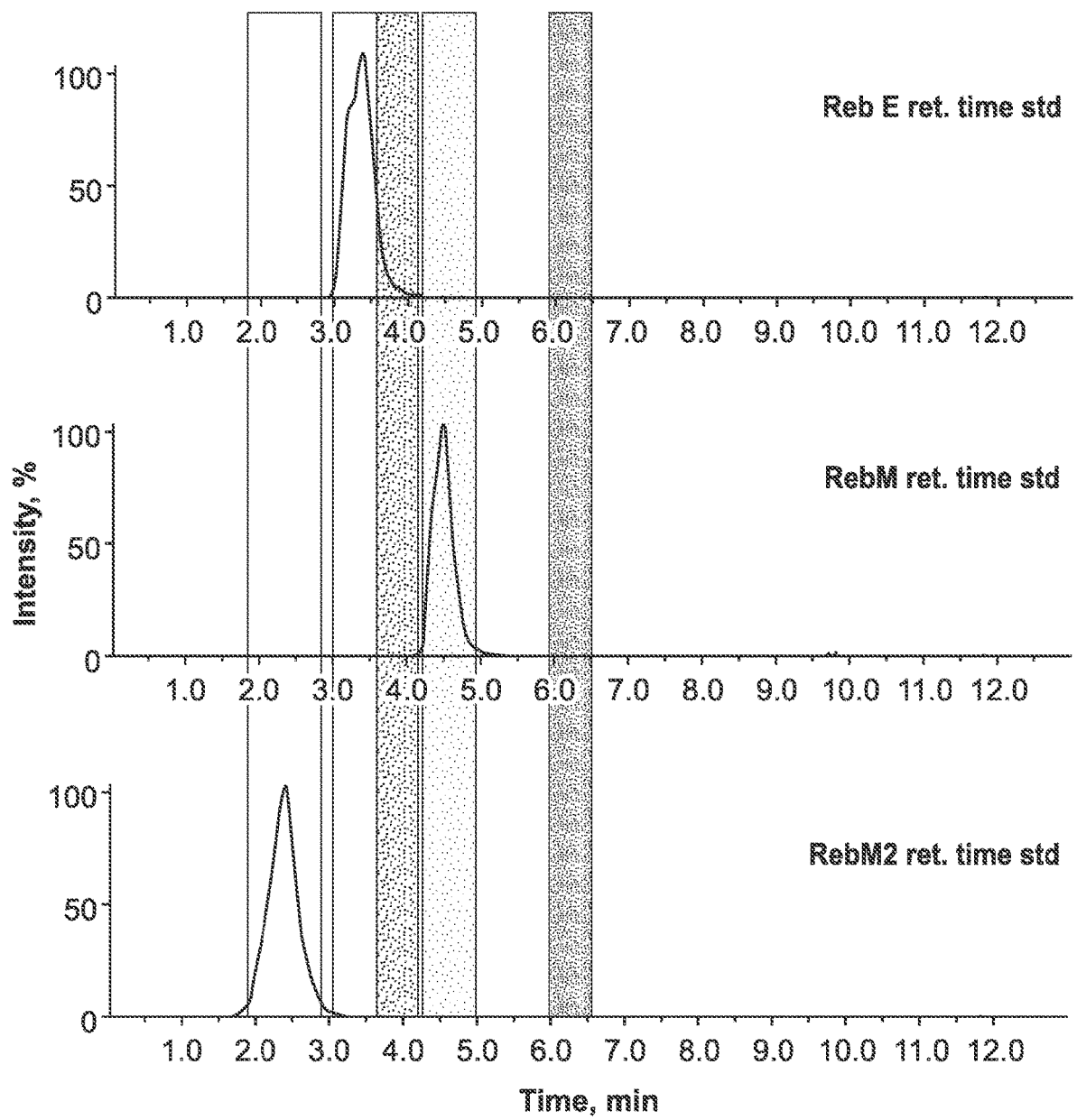
Figure 5B:
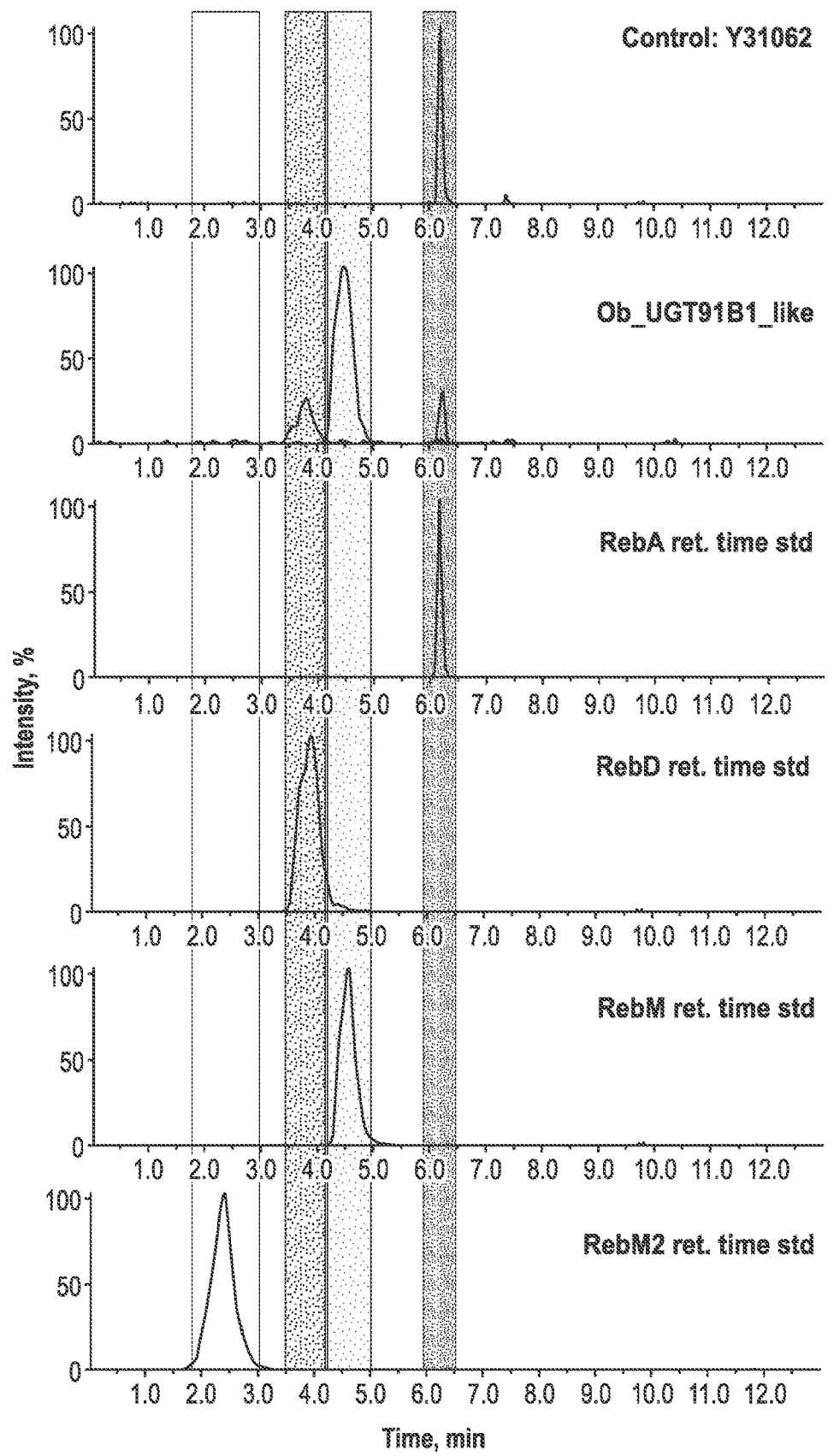
Figure 5C:
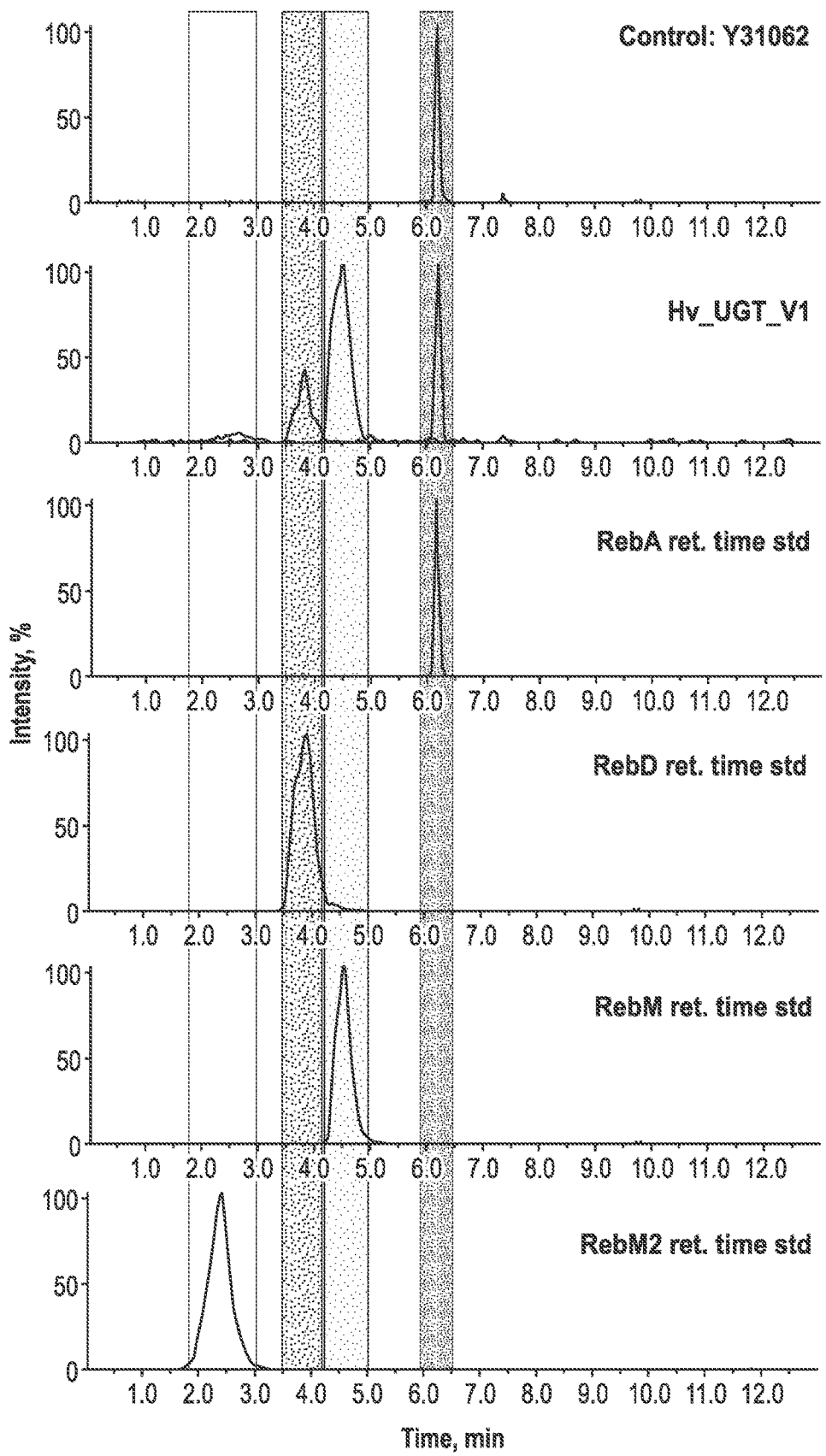
Figure 5D:
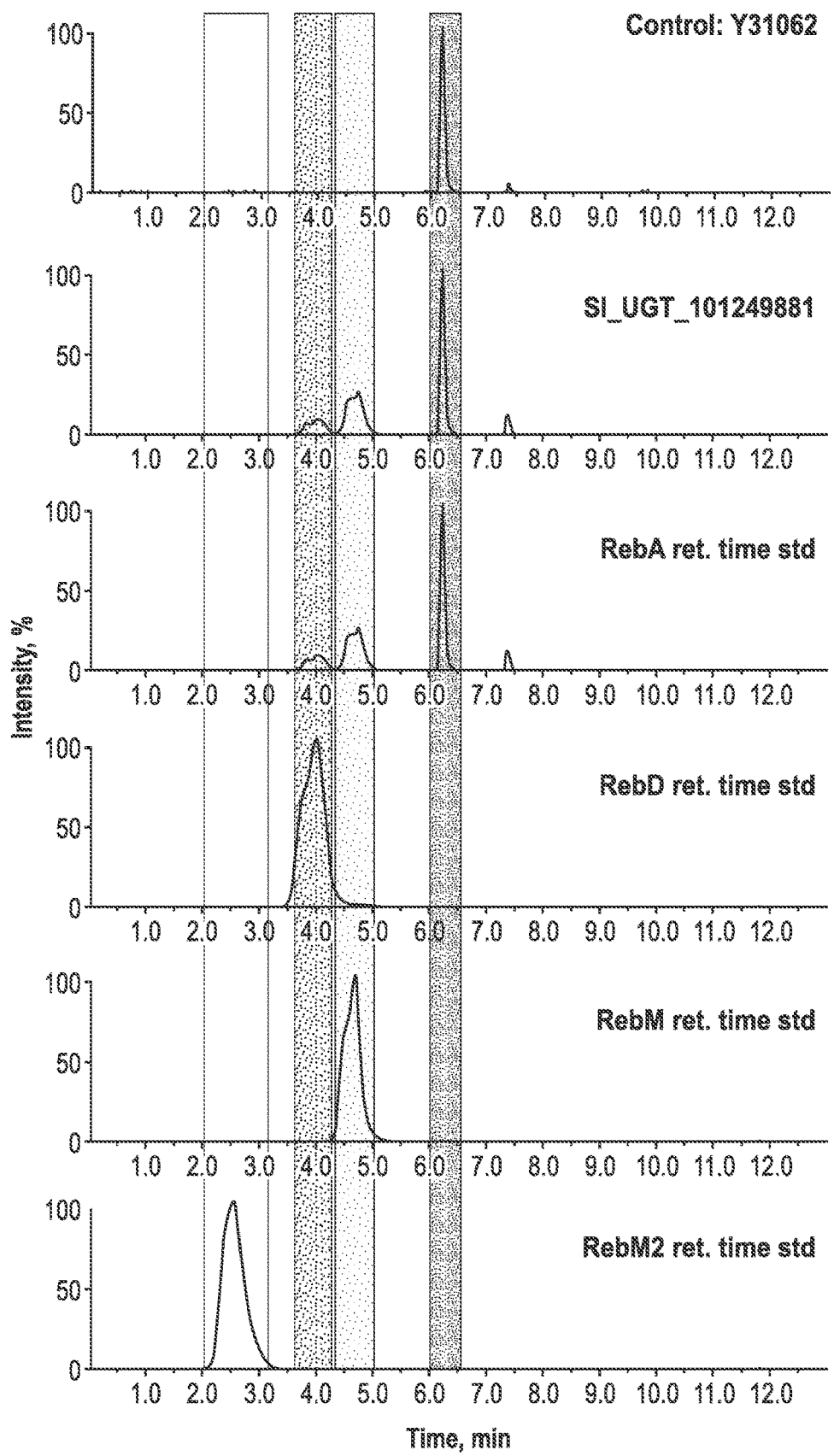
Figure 5D:
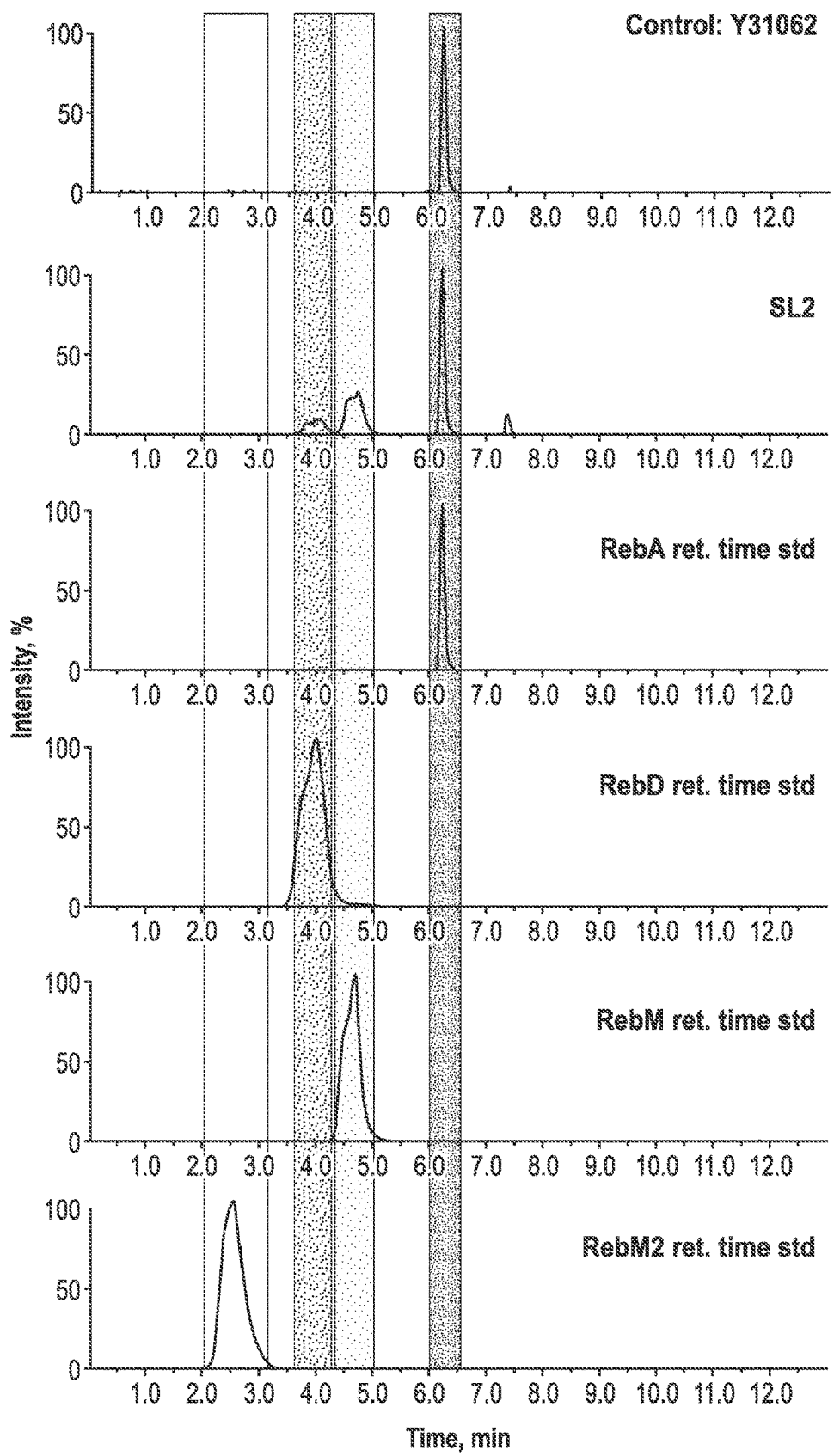
Figure 5E:
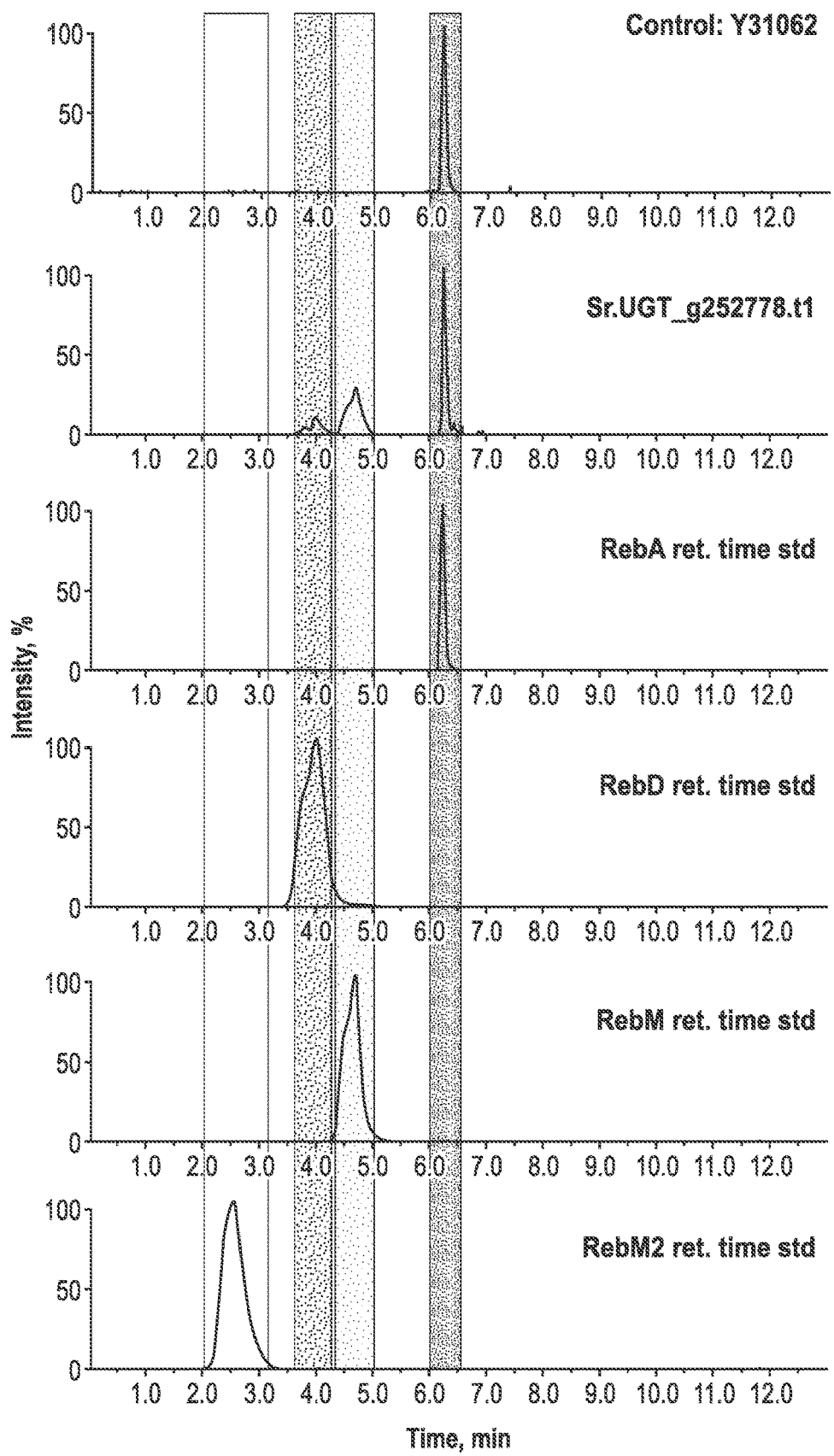
Figure 5F:
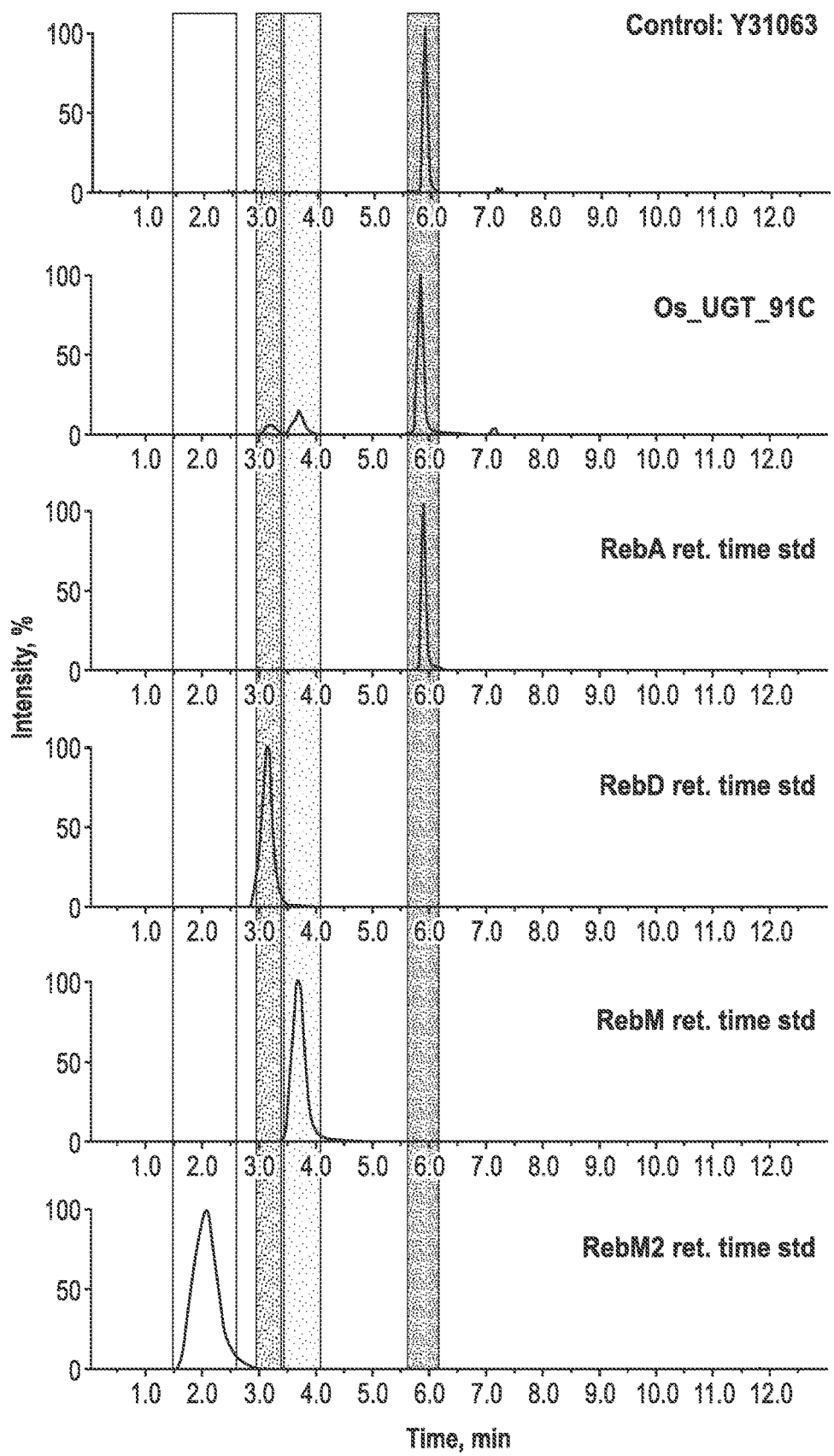
Figure 5G:
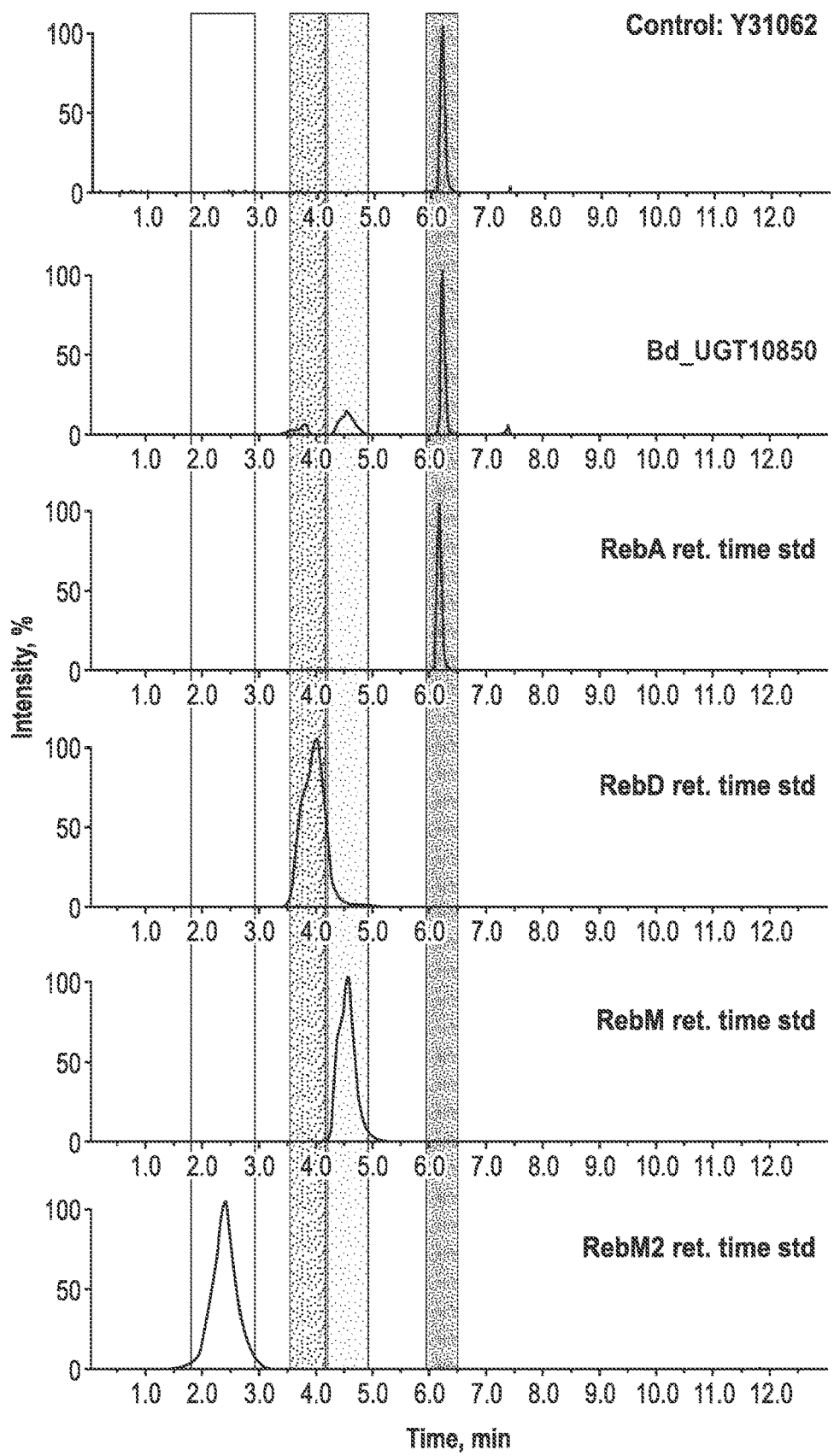
Figure 5H:
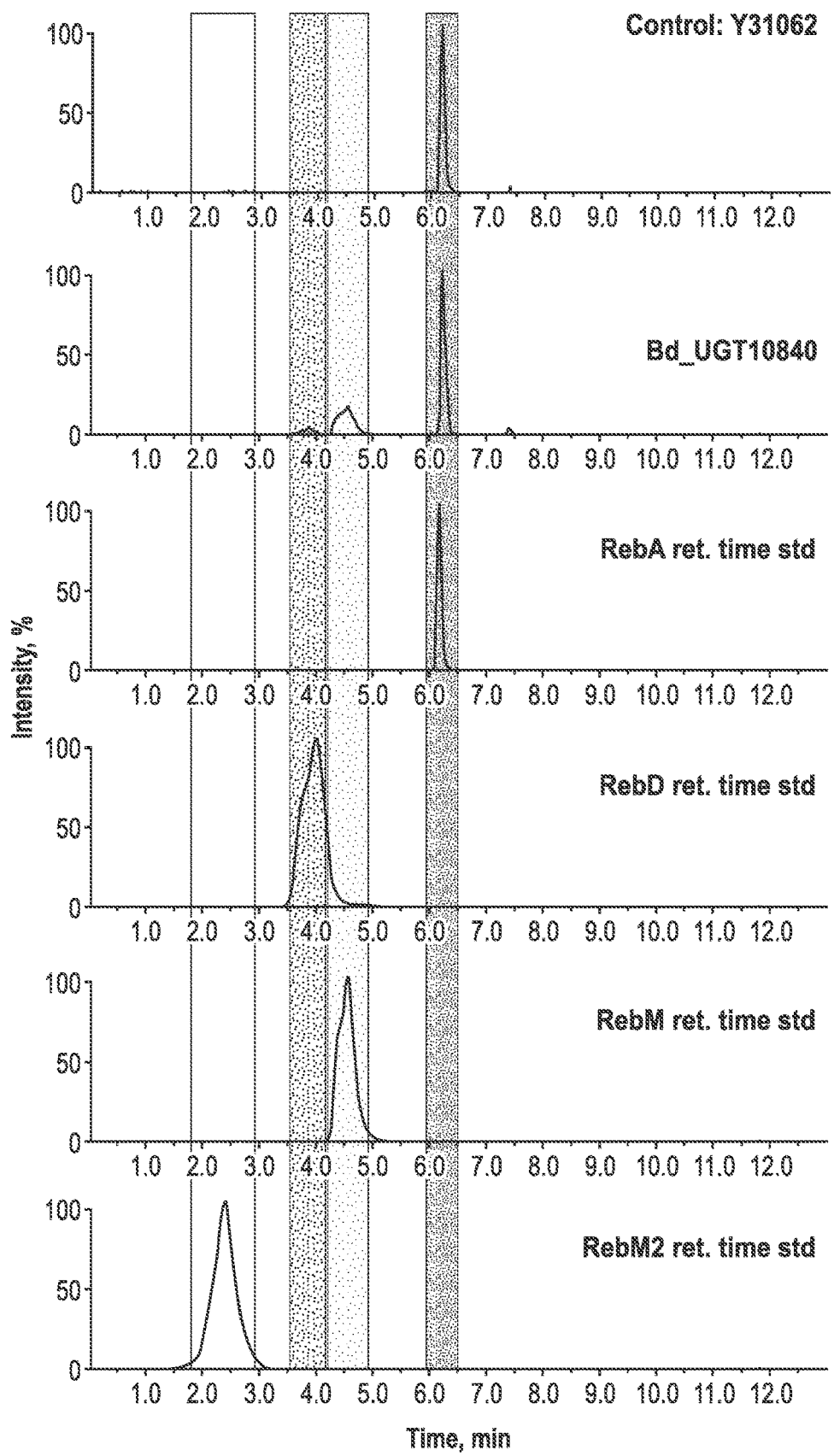
Figure 5I:
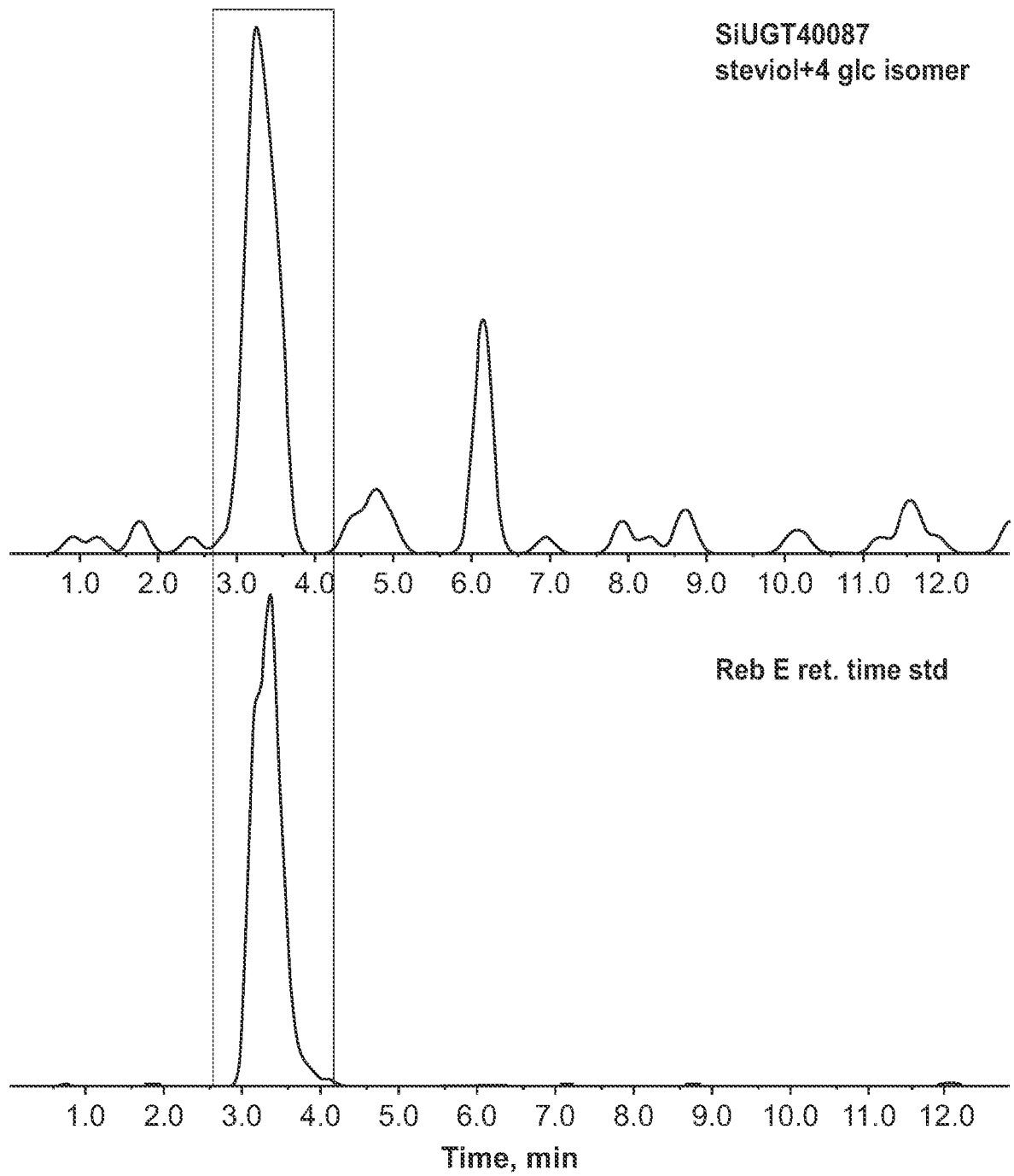

Example 10: UGT40087 Enzyme Activity is Specific for the C-2' Position of a 19-O-Glucose Steviol Glycoside UGT40087 catalyzes the reaction of addition of a second sugar moiety to the C-2' of a 19-O-glucose of either stevioside or RebA. As shown in FIGS. 5a and 5i, the parent control strain without UGT40087 (as described in Example 2) is able to make RebA, but does not make detectable amounts of RebE, RebD, or RebM. Addition of UGT40087 into the parent cell now results in a detectable amount of RebE, indicating that UGT40087 catalyzes the addition of a second glucose moiety to the C-2' position of a 19-O-glucose in a beta-1,2 linkage of stevioside to make RebE. Also, two new peaks for RebD and RebM appear in the chromatogram for the strain containing UGT40087, while the peak for RebA decreases significantly, compared to the parent strain without UGT40087. Therefore, UGT40087 is able to catalyze the addition of a second glucose moiety to the C-2' position of a 19-O-glucose in a beta-1,2 linkage of rebaudioside A to rebaudioside D. The presence of UGT76G1 in the strain then catalyzes the final glucose addition to convert RebD to RebM.

In order to screen of the ability to add a sugar to the C-2' position of a 13-O-glucose in a beta-1,2 linkage of either steviolmonoside or rubusoside, a base strain was made that carries high flux to rubusoside only. The rubusoside base strain is genetically identical to the RebA base strain described in example 2, except that the rubusoside base strain does not contain the enzyme UGT91D_like3. As shown in Table 7, the rubusoside base strain, which has UGT74G1, UGT85C2, and UGT76G1 is only capable of making 19-glycoside, steviolmonoside, and rubusoside. Adding UGT40087 to this strain does not change this profile at all. If UGT40087 were capable of adding a sugar to the C-2' position of a 13-O-glucose in a beta-1,2 linkage of either steviolmonoside or rubusoside, then there should be detectable amounts of either or both steviolbioside or stevioside. Steviolbioside, stevioside, and also RebA are seen when the strain is transformed with UGT91D_like3, which is capable of adding a sugar to the C-2' position of a 13-O-glucose in beta-1,2 linkage of both steviolmonoside and rubusoside.

EUGT 11 (Os_UGT_91C1) was previously characterized by others to catalyze the addition of a second sugar moiety to the C-2' position of a either a 19-O-steviol glycoside or a 13-O-steviol glycoside. See FIG. 5 of WO 2013/022989. As noted above, UGT40087 does not appearto catalyze the addition of a sugar to the C-2' position of a 13-O-glucose in a beta-1,2 linkage of either steviolmonoside or rubusoside at a detectable level. These results indicate that UGT40087 is a UDP-glycosyltransferase which is functionally distinguishable and produces different results compared to EUGT11.

swapping candidate pairs, 2) select domain swapping site for making a chimera between the pair of UGTs (with an option to mutate the C-terminal domain to improve interactions with the targeted substrate and the N-terminal domain), and 3) create, test and evolve chimeric proteins for the desired activity. This approach was taken in this example to perform domain swapping as described below.

Four UGTs were selected as parents for constructing chimeras: UGT40087 (SEQ ID No. 11), UGT Si91Dlike (SEQ ID No. 12), OS_UGT_91C1 (SEQ ID No. 8), and 91Dlike3 (SEQ ID No. 7). The N-terminal domain of UGT40087 was used to replace the N-terminal domains of Si91Dlike, OS_UGT_91C1 and 91Dlike3, creating three

TABLE 7

Titers for all steviol glycoside intermediates in the pathway to RebM are normalized to the uM of steviolmonoside produced in the rubusoside base strain (bolded).

| Strain | 19-glycoside (uM) normalized | RebA (uM) normalized | RebB (uM) normalized | RebD (uM) normalized | RebM (uM) normalized | Rubusoside (uM) normalized | Steviolbioside (uM) normalized | Steviolmonoside (uM) normalized | Stevioside (uM) normalized |
|---|---|---|---|---|---|---|---|---|---|
| Rubusoside base strain | 2.01 | 0.00 | 0.00 | 0.00 | 0.00 | 0.73 | 0.00 | 1.00 | 0.00 |
| Rubusoside base strain + UGT40087 | 1.60 | 0.00 | 0.00 | 0.00 | 0.00 | 0.82 | 0.00 | 1.15 | 0.00 |
| Rubusoside base strain + 91D_like3 | 2.50 | 0.25 | 0.22 | 0.00 | 0.00 | 0.15 | 0.13 | 0.35 | 0.10 |

Example 11. Engineering of UGT Chimeras by Swapping the N-Terminal Domains

Figures 6, 7:
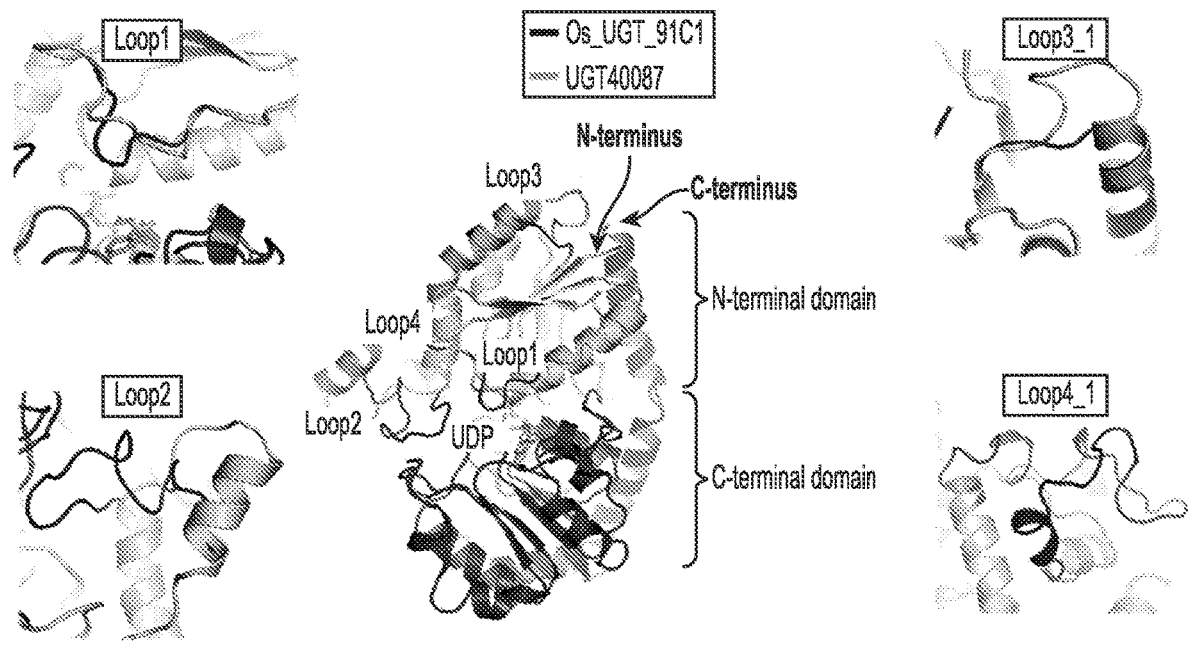
FIG. 6 illustrates a homology model of UGT40087 structure. Its N- and C-terminal domains are shown in light and dark gray, and the four loops used in the loop swapping experiment are also labeled on the structure.
FIG. 7 illustrates a schematic overview of the UGT domain swapping constructs

Plant UDP-glycosyltransferases (UGTs) share highly conserved protein structures even though they have relatively low amino acid sequence homology. These UGTs, which adopt a so-called GT-B structural fold, consist of two domains, roughly breaking at the mid-point of their primary amino acid sequences. The N-terminal domain is the sugar acceptor domain that mainly determines the substrate specificity. As expected, this domain is a more variable domain in terms of its amino acid sequence, reflecting the diverse substrates that can be glycosylated by UGTs. The more conserved C-terminal domain is the sugar donor domain, where UDP-glucose is bound. The two domains usually are linked by a flexible linker creating an ideal region for splitting the protein for domain swapping designs (FIG. 6). Given the nature of highly conserved domain structure of UGTs, domains from any two UGTs could be recombined to either alter substrate specificity or enhance a desired function such as catalytic activity. In this example, we investigated the role of the N-terminal domain of UGT40087 in conferring substrate specificity, i.e., the activity of converting RebA to RebD by designing several UGT chimeras via domain swapping.

The general approach one would take to design a domain swapping experiment involves the following steps: 1) select chimeras with 97%, 79% and 71% overall sequence identities to UGT40087, respectively.

SWISS-MODEL was used to generate structural models for all four UGTs. The exact amino acid positions ("swapping sites") were selected based on structural alignments and sequence alignments. To minimize the perturbation to the 3-dimensional folding of the chimeric proteins, the flexible region located between the N- and C-terminal domains, which constitute the two distinct halves of the enzyme (FIG. 6), were used for swapping sites. Gly215 and Leu216 (amino acid numbers refer to UGT40087) in this region are highly conserved in all UGTs including the four UGTs in this Example. Therefore, the two domains were split in between these two residues for domain swapping (FIG. 6).

In order to test the effects of domain swaps, the experiments were performed in the yeast strains that are genetically identical, except that the yeast strains include different UGTs. These yeast strains are, however, genetically different from those used in the UGT diversity screening described in Example 4. The general methods described in Examples 4 to 7 were used for strain transformation, culture, and analysis. The RebA to RebD conversion ratios of various domain swap designs are shown in Table 8 below.

TABLE 8

UGT40087 domain swapping results

| Chimera | Median RebA to RebD conversion ratio | Sequence identity to UGT40087 (full length) | Sequence identity to UGT40087 (N-domain) | Sequence identity to UGT40087 (C-domain) |
|---|---|---|---|---|
| UGT40087 | 0.97 | 100% | 100% | 100% |
| Si91Dlike | 0.07 | 90% | 85% | 93% |

TABLE 8-continued

UGT40087 domain swapping results

| Chimera | Median RebA to RebD conversion ratio | Sequence identity to UGT40087 (full length) | Sequence identity to UGT40087 (N-domain) | Sequence identity to UGT40087 (C-domain) |
| --- | --- | --- | --- | --- |
| Os_UGT_91C1 | 0.88 | 54% | 50% | 60% |
| 91Dlike3 | 0.11 | 36% | 39% | 42% |
| Chimera_UGT40087-Si91Dlike | 0.96 | 97% | 100% | 93% |
| Chimera_UGT40087-Os_UGT_91C1 | 0.28 | 79% | 100% | 60% |
| Chimera_UGT40087-91Dlike3 | 0.07 | 71% | 100% | 42% |
| Control (no enzyme) | 0.07 | N/A | N/A | N/A |

UGT40087 shares 90%, 54% and 36% overall sequence identities with Si91Dlike, Os_UGT_91C1 and 91Dlike3, respectively. Except 91Dlike3, which has approximately 40% sequence identities in both the N- and C-terminal sequences to UGT40087, the chimeras of the UGT40087 N-terminal domain and the C-terminal domains of Si91Dlike and Os_UGT_91C1 are active in converting RebA to RebD (Table 8). Even though Si91Dlike has no detectable activity, the replacement of its N-terminal domain with that of UGT40087 conferred all of the UGT40087 activity, indicating that the N-terminal domain of UGT40087 is important for RebA to RebD conversion.

Alignments of the four parent UGTs also reveal six N-terminal amino acid residues (V11, I12, P55, E90, S203, E223, and V413 in UGT40087; FIG. 8—the sequence alignment figure) that are shared by the two active enzymes (UGT40087 and Os_UGT_91C1) for RebA to RebD conversion, but are different from those in the two inactive enzymes (Si91Dlike and 91Dlike3).

Example 12. Engineering of UGT Variants by Swapping N-Terminal Loops

Comparison of modeled structures of UGT40087 and Os_UGT_91C1 revealed four loops that possess significant conformational differences at the N terminal sugar acceptor domain. The loop locations are shown in FIG. 6. To identify loops that may contribute to UGT40087's superior activity for RebA to RebD conversion, each of these loops was swapped in the two proteins to generate a total of 12 UGT variants. Two versions of loop_3 and loop_4 were designed to account for two possible loop lengths. Detailed designs are listed in Tables 9 and 10.

TABLE 9

UGT40087-based loop swapping design (Sequences between amino acids with subscript number are the regions being swapped in from Os_UGT_91C1).

| Loop Number | Swapping sequence |
| --- | --- |
| UGT40087_loop1 | $S_{42}$-TPRN ISRLPPVPPALAP (SEQ ID NO: 27)-$L_{60}$ |
| UGT40087_loop2 | $V_{71}$-EGLPDGAESTNDVPHDRPDMV (SEQ ID NO: 14)-$E_{90}$ |
| UGT40087_loop3_1 | $F_{103}$-SEFLGTACAD (SEQ ID NO: 15)-$W_{121}$ |
| UGT40087_loop3_2 | $F_{103}$-SEFLGTACADWVIVDVFHH (SEQ ID NO: 16)-$W_{130}$ |
| UGT40087_loop4_1 | $Y_{156}$-ADRRLERAETESPAAAGQGRPAAAPTFEVARMKLIRTKGSSGM (SEQ ID NO: 17)-$S_{171}$ |
| UGT40087_loop4_2 | $A_{143}$-MMLLGSAHMIASIADRRLERAETESPAAAGQGRPAAAPTFEVARMKLIRTKGSSGM (SEQ ID NO: 18)-$S_{171}$ |

In Table 9, the amino acid sequence with a sequence ID number between two amino acid residues with subscripts is the loop region being swapped in from Os_UGT_91C into the UGT40087 base. The two amino acid residues with subscripts adjacent to the swapped loop region from Os_UGT_91C and the subscript numbers correspond to the amino acid residues and amino acid positions of UGT40087, respectively, prior to incorporation of the swapped loop region. In the new chimeric UGTs listed in Table 9, the swapped loop region from Os_UGT_91C replaced the corresponding loop region of the UGT40087 base.

It is noted that the amino acid sequence of SEQ ID NO:27, the swapped loop region, integrated into UGT40087_loop1 is a modified version of the original loop1 of Os_UGT_91C1. More specifically, the 12$^{th}$ amino acid residue in the sequence of SEQ ID NO:27 is proline (instead of arginine which is present in the corresponding position in the original loop1 of Os_UGT_91C having SEQ ID NO:8). Thus, in UGT40087_loop1, there is a single amino acid substitution, proline at position 51, compared to the original sequence of UGT40087 having SEQ ID NO:11. The position of the substituted proline at position 51 in UGT40087_loop1 is shown in boldface in Table 9.

TABLE 10

Os_UGT_91C1-based loop swapping design (Sequences between amino acids with subscript number are the regions being swapped in from UGT40087).

| Loop Number | Swapping sequence |
| --- | --- |
| Os_UGT_91C1_loop1 | $S_{49}$-TPRNISRLRPVRPALAP (SEQ ID NO: 28)-$L_{67}$ |
| Os_UGT_91C1_loop2 | $V_{79}$-DGLPDGAEATSDIPPGKT (SEQ ID NO: 19)-$E_{100}$ |
| Os_UGT_91C1_loop3_1 | $F_{113}$-AAFLDAACADGSTNKVD (SEQ ID NO: 20)-$W_{124}$ |
| Os_UGT_91C1_loop3_2 | $F_{113}$-AAFLDAACADGSTNKVDWLFLDNFQY (SEQ ID NO: 21)-$W_{133}$ |
| Os_UGT_91C1_loop4_1 | $I_{159}$-GVPRVEPPVDGSTA (SEQ ID NO: 22)-$S_{203}$ |
| Os_UGT_91C1_loop4_2 | $A_{146}$-LNLTFAASTSAEYGVPRVEPPVDGSTA (SEQ ID NO: 23)-$S_{203}$ |

In Table 10, the amino acid sequence with a sequence ID number between two amino acid residues with subscripts is the loop region being swapped in from UGT40087 into the Os_UGT_91C1 base. The two amino acid residues with subscripts adjacent to the swapped loop region from UGT40087 and the subscript numbers correspond to the amino acid residues and amino acid positions of Os_UGT_91C1, respectively, prior to incorporation of the swapped loop region. In the new chimeric UGTs listed in Table 10, the swapped loop region from UGT40087 replaced the corresponding loop region of the OS_UGT_91C1 base.

It is noted that the amino acid sequence of SEQ ID NO:28, the swapped loop region, integrated into Os_UGT_91C1 loop1 is a modified version of the original loop1 of UGT40087. More specifically, the 12$^{th}$ amino acid residue in the sequence of SEQ ID NO:28 is arginine (instead of proline which is present in the corresponding position in the original loop1 of UGT40087 having SEQ ID NO:11). Thus, in Os_UGT_91C1 loop1, there is a single amino acid substitution, arginine at position 58, compared to the original sequence of Os_UGT_91C1 having SEQ ID NO:8. The position of the substituted arginine at position 58 in Os_UGT_91C1 loop1 is shown in boldface in Table 10.

The variant proteins were synthesized by Twist Bioscience with 60 bp of sequence homologous to the GAL1 promoter and a yeast terminator flanking the F-CphI sequences in the landing pad described in Example 4. Each synthesized UGT variant was tested individually as a single chromosomal copy for its activity in converting RebA to RebD in the same strain background as in Example 11 for the UGT domain swapping chimera experiments. To create the strains, the UGT chimera donor DNAs and a plasmid containing the endonuclease F-CphI were transformed into the yeast host. Correct integrations were verified by colony PCR using a reverse primer internal to the specific UGT genes and a universal forward primer at the end of the integration locus. The confirmed strains were tested for RebA to RebD conversion as described above.

TABLE 11

UGT40087-based loop swapping results

| Loop# | Median RebA to RebD conversion ratio | Sequence identity to UGT40087 (full length) | Sequence identity to UGT40087 (N-domain) |
| --- | --- | --- | --- |
| UGT40087 | 0.97 | 100% | 100% |
| UGT40087_loop1 | 0.96 | 99% | 99% |
| UGT40087_loop2 | 0.43 | 98% | 95% |
| UGT40087_loop3_1 | 0.96 | 97% | 95% |
| UGT40087_loop3_2 | 0.94 | 92% | 92% |
| UGT40087_loop4_1 | 0.41 | 92% | 84% |
| UGT40087_loop4_2 | 0.06 | 90% | 80% |
| Control (no enzyme) | 0.07 | N/A | N/A |

TABLE 12

Os_UGT_91C1-based loop swapping results

| Loop# | Median RebA to RebD conversion ratio | Sequence identity to UGT40087 (full length) | Sequence identity to UGT40087 (N-domain) |
| --- | --- | --- | --- |
| Os_UGT_91C1 | 0.88 | 54% | 50% |
| Os_UGT_91C1_loop1 | 0.70 | 54% | 54% |
| Os_UGT_91C1_loop2 | 0.41 | 54% | 54% |
| Os_UGT_91C1_loop3_1 | 0.89 | 55% | 55% |
| Os_UGT_91C1_loop3_2 | 0.12 | 57% | 57% |
| Os_UGT_91C1_loop4_1 | 0.97 | 61% | 61% |
| Os_UGT_91C1_loop4_2 | 0.07 | 66% | 66% |
| Control (no enzyme) | 0.07 | N/A | N/A |

With UGT40087 as the parent, the loop-swapping variants were all active in converting RebA to RebD except for UGT40087 loop4_2 (Table 11). Loop4_2 is a long sequence that is located close to the N- and C-terminal domain interface, and its replacement may create significant perturbation to the overall structure of the variant. Among all the active variants, N-terminal sequence identities to UGT40087 range from 84% (Loop4_1) and 99% (Loop1).

With Os_UGT_91C1 as the parent, most of the loop-swapping variants also showed activity in converting RebA to RebD (Table 12). Again, Loop4_2 swapping abolished the activity, supporting the hypothesis that its replacement may impact the structural integrity of the variant. Notably, incorporation of the Loop4_1 led to an increased RebA to RebD conversion (from 88% to 97%), indicating that Loop4_1 is responsible for conferring superior activity of UGT40087. In addition, the results from the loop swapping experiments with both proteins as parents also showed that these loop regions are important for conferring differences in activity and substrate specificity of the UGTs having RebA to RebD activity, and additional swapping of homolog loop variants or mutagenesis of these loop regions may be employed to generate improved UGT variants for converting RebA to RebD.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
                        SEQUENCE LISTING

SEQ ID NO: 1 (UGT40087 version 1)
MDASDSSPLHIVIFPWLAFGHMLASLELAERLAARGHRVSFVSTPRNISRLRPVPPALAPLIDFVALPLP
RVDGLPDGAEATSDIPPGKTELHLKALDGLAAPFAAFLDAACADGSTNKVDWLFLDNFQYWAAAAAADHK
IPCALNLTFAASTSAEYGVPRVEPPVDGSTASILQRFVLTLEKCQFVIQRACFELEPEPLPLLSDIFGKP
VIPYGLVPPCPPAEGHKREHGNAALSWLDKQQPESVLFIALGSEPPVTVEQLHEIALGLELAGTTFLWAL
KKPNGLLLEADGDILPPGFEERTRDRGLVAMGWVPQPIILAHSSVGAFLTHGGWASTIEGVMSGHPMLFL
TFLDEQRINAQLIERKKAGLRVPRREKDGSYDRQGIAGAIRAVMCEEESKSVFAANAKKMQEIVSDRNCQ
EKYIDELIQRLGSFEK SEQ ID NO: 2 (sr.UGT_g252778)
MATNDDDRKQLHVAMFPWLAFGHILPFLELSKLIAQNGHKVSFLSTTRNIQRLPSHLTPLINLVKLTL
PRVQELPEDAEATTDIKHDDQDHLLNASDGLQPEVTRFLEEESPDWIIFDYSYYWLPPVAAELGISRA
FFMTFPTWTMALTRLPSDQLTAEDLMTLSKISFKKHEIVNLMYGTSTQGDLYRLTMACNGSDCILIRC
CYEFEPQWLTLLEKLLPVPVVPVGLLPPEIHGDEKDDDTWVSVKEWLDGQHKGHVVYVALGSEAMVSK
DELGELALGLELSGLPFFWALRKPPGSTESDSVELPDGFMERTRNRGVVWTSWAPQLRILSHESVCGF
LTHCGVSSIVEGLMFGHPLIMLPIFGDQIMNAQVLADKQVGIEIPRNEEDGWFTKESVAKSLRSVVVD
DEGEIYKANARELSKIFSDTDLGKKYISHFIDFLMMEIVKT*

SEQ ID NO: 3 (Bd_UGT10840)
MDNGSSSSSSSPLHVVICPWLAFGHQLPCLDLAERLALRGHRVSFVSTPRIIARLPPVRPVAASLVDL
VALPLPRVDGLPEGAESTNDVPYEKFELHRKAFDGLAVPFSEFLRAACAEEGKKPDWIIVDTFHHWAA
AAAIEHKVPCAMLMLGAAGLIVAWATQPSKHVTSEQQEQSAAEPPRFETERRKLATTQRASGMSIAER
CSVTLERCNLVAMRSCLEWEPESIPLATTIGGKQLVPLGLLPPSPEGGRGVSKEDATVRWLDAQPTKS
VVYVALGSEVPLGAKEVHELALGLELAGTRFLWSLRKPSGVSDADILPSGFEERTRGRGLVTMGWVPQ
ISVLAHGAVGAFLTHCGWNSIIEGLQFGHPLVMLPIFGDQGPNARMMEGRKVGVQVPRDESNGSFDRE
GVATTVRAVAVEEEGNRIFTANAKKMQEIVADKGCHDKYVDKFIQKLRSYME*

SEQ ID NO: 4 (Hv_UGT_V1)
MDGDGNSSSSSSPLHVVICPWLALGHLLPCLDIAERLASRGHRVSFVSTPRNIARLPPLRPAVAPLVE
FVALPLPHVDGLPEGAESTNDVPYDKFELHRKAFDGLAAPFSEFLRAACAEGAGSRPDWLIVDTFHHW
AAAAAVENKVPCVMLLLGAATVIAGFARGVSEHAAAAVGKERPAAEAPSFETERRKLMTTQNASGMTV
AERYFLTLMRSDLVAIRSCAEWEPESVAALTTLAGKPVVPLGLLPPSPEGGRGVSKEDAAVRWLDAQP
AKSVVYVALGSEVPLRAEQVHELALGLELSGARFLWALRKPTDAPDAAVLPPGFEERTRGRGLVVTGW
VPQIGVLAHGAVAAFLTHCGWNSTIEGLLFGHPLIMLPISSDQGPNARLMEGRKVGMQVPRDESDGSF
RREDVAATVRAVAVEEDGRRVFTANAKKMQEIVADGACHERCIDGFIQQLRSYKA*

SEQ ID NO: 5 (Bd_UGT10850)
MDAAGSSSPMHIVIFPWLASGHLLPCLELAERLAARGHLVSFVSTPRNLARLPPVSPALAPLVDLVAL
PLPRVAGLPDGAESTADVPADKFDLHRQAFDGLAAPFAAFLDADVGKKKKPDWIVADFVHHWVAAAAQ
EREVPCAMLVPCAAAVAVLAGPPPESISNADERQVIVKVMDAAPRFEAEQAMEEFAAEDASGSSSGLS
VLSRFYMTLKRCKVVALRSCPELEPDAFPLLTRLYGKPAVPLGLLPPPPNGTRSRGMDDEAIIRWLNA
QPASSVVYVALGSEAPLRAELLRELAHGLELAGTRFLWALRKPVGVQDGDSVLPDGFVERTSRRGLVV
ARWVSQVSILAHGAVGAFLTHCGWGSVVEGLQFGRPLIMLPIAGDQGPNARLMEERKVGVSVPRDEKD
GSFTRGGVAGAIRAVVEEDGRLFAANAEKLREIVASRECHERCIDGFIQHLRCCK

SEQ ID NO: 6 (Ob_UGT91B1_like)
MENGSSPLHVVIFPWLAFGHLLPFLDLAERLAARGHRVSFVSTPRNLARLRPVRPALRGLVDLVALPL
PRVHGLPDGAEATSDVPFEKFELHRKAFDGLAAPFSAFLDAACAGDKRPDWVIPDFMHYWVAAAAQKR
GVPCAVLIPCSADVMALYGQPTETSTEQPEAIARSMAAEAPSFEAERNTEEYGTAGASGVSIMTRFSL
TLKWSKLVALRSCPELEPGVFTTLTRVYSKPVVPFGLLPPRRDGAHGVRKNGEDDGAIIRWLDEQPAK
SVVYVALGSEAPVSADLLRELAHGLELAGTRFLWALRRPAGVNDGDSILPNGFLERTGERGLVTTGWV
PQVSILAHAAVCAFLTHCGWGSVVEGLQFGHPLIMLPIIGDQGPNARFLEGRKVGVAVPRNHADGSFD
RSGVAGAVRAVAVEEEGKAFAANARKLQEIVADRERDERCTDGFIHHLTSWNELEA SEQ ID NO: 7 (UGT91D_like3)
MYNVTYHQNSKAMATSDSIVDDRKQLHVATFPWLAFGHILPYLQLSKLIAEKGHKVSFLSTTRNIQRL
SSHISPLINVVQLTLPRVQELPEDAEATTDVHPEDIPYLKKASDGLQPEVTRFLEQHSPDWIIYDYTH
YWLPSIAASLGISRAHFSVTTPWAIAYMGPSADAMINGSDGRTTVEDLTTPPKWFPFPTKVCWRKHDL
ARLVPYKAPGISDGYRMGLVLKGSDCLLSKCYHEFGTQWLPLLETLHQVPVVPVGLLPPEIPGDEKDE
TWVSIKKWLDGKQKGSVVYVALGSEVLVSQTEVVELALGLELSGLPFVWAYRKPKGPAKSDSVELPDG
FVERTRDRGLVWTSWAPQLRILSHESVCGFLTHCGSGSIVEGLMFGHPLIMLPIFGDQPLNARLLEDK
QVGIEIPRNEEDGCLTKESVARSLRSVVVEKEGEIYKANARELSKIYNDTKVEKEYVSQFVDYLEKNA
RAVAIDHES*

SEQ ID NO: 8 (Os_UGT_91C1)
MDSGYSSSYAAAAGMHVVICPWLAFGHLLPCLDLAQRLASRGHRVSFVSTPRNISRLPPVRPALAPLV
AFVALPLPRVEGLPDGAESTNDVPHDRPDMVELHRRAFDGLAAPFSEFLGTACADWVIVDVFHHWAAA
AALEHKVPCAMMLLGSAHMIASIADRRLERAETESPAAAGQGRPAAAPTFEVARMKLIRTKGSSGMSL
```

SEQUENCE LISTING

```
AERFSLTLSRSSLVVGRSCVEFEPETVPLLSTLRGKPITFLGLMPPLHEGRREDGEDATVRWLDAQPA
KSVVYVALGSEVPLGVEKVHELALGLELAGTRFLWALRKPTGVSDADLLPAGFEERTRGRGVVATRWV
PQMSILAHAAVGAFLTHCGWNSTIEGLMFGHPLIMLPIFGDQGPNARLIEAKNAGLQVARNDGDGSFD
REGVAAAIRAVAVEEESSKVFQAKAKKLQEIVADMACHERYIDGFIQQLRSYKD*

SEQ ID NO: 9 (Sl_UGT_101249881)
MATNLRVLMFPWLAYGHISPFLNIAKQLADRGFLIYLCSTRINLESIIKKIPEKYADSIHLI
ELQLPELPELPPHYHTTNGLPPHLNPTLHKALKMSKPNFSRILQNLKPDLLIYDVLQPWAEH
VANEQNIPAGKLLTSCAAVFSYFFSFRKNPGVEFPFPAIHLPEVEKVKIREILAKEPEEGGR
LDEGNKQMMLMCTSRTIEAKYIDYCTELCNWKVVPVGPPFQDLITNDADNKELIDWLGTKHE
NSTVFVSFGSEYFLSKEDMEEVAFALELSNVNFIWVARFPKGEERNLEDALPKGFLERIGER
GRVLDKFAPQPRILNHPSTGGFISHCGWNSAMESIDFGVPIIAMPIHNDQPINAKLMVELGV
AVEIVRDDDGKIHRGEIAETLKSVVTGETGEILRAKVREISKNLKSIRDEEMDAVAEELIQL
CRNSNKSK

SEQ ID NO: 10 (Sr.KAH)
MEASYLYISILLLLASYLFTTQLRRKSANLPPTVFPSIPIIGHLYLLKKPLYRTLAKIAA
KYGPILQLQLGYRRVLVISSPSAAEECFTNNDVIFANRPKTLFGKIVGGTSLGSLSYGDQ
WRNLRRVASIEILSVHRLNEFHDIRVDENRLLIRKLRSSSSPVTLITVFYALTLNVIMRM
ISGKRYFDSGDRELEEEGKRFREILDETLLLAGASNVGDYLPILNWLGVKSLEKKLIALQ
KKRDDFFQGLIEQVRKSRGAKVGKGRKTMIELLLSLQESEPEYYTDAMIRSFVLGLLAAG
SDTSAGTMEWAMSLLVNHPHVLKKAQAEIDRVIGNNRLIDESDIGNIPYIGCIINETLRL
YPAGPLLFPHESSADCVISGYNIPRGTMLIVNQWAIHHDPKVWDDPETFKPERFQGLEGT
RDGFKLMPFGSGRRGCPGEGLAIRLLGMTLGSVIQCFDWERVGDEMVDMTEGLGVTLPKA
VPLVAKCKPRSEMTNLLSEL*

SEQ ID NO: 11 (UGT40087 version 2)
MDSASSSPLHIVIFPWLAFGHMLASLELAERLAARGHRVSFVSTPRNISRLRPVPPALAPLIDFVALPLP
RVDGLPDGAEATSDIPPGKTELHLKALDGLAAPFAAFLDAACADGSTNKVDWLFLDNFQYWAAAAAADHK
IPCALNLTFAASTSAEYGVPRVEPPVDGSTASILQRFVLTLEKCQFVIQRACFELEPEPLPLLSDIFGKP
VIPYGLVPPCPPAEGHKREHGNAALSWLDKQQPESVLFIALGSEPPVTVEQLHEIALGLELAGTTFLWAL
KKPNGLLLEADGDILPPGFEERTRDRGLVAMGWVPQPIILAHSSVGAFLTHGGWASTIEGVMSGHPMLFL
TFLDEQRINAQLIERKKAGLRVPRREKDGSYDRQGIAGAIRAVMCEEESKSVFAANAKKMQEIVSDRNCQ
EKYIDELIQRLGSFEK SEQ ID NO: 12 (Si91Dlike)
MDSSQSPPLHIAVFPWLAFGHLLPNLELAERLAARGHRVSFVSTPRIISRLRPVPLALAPLIDFVALPLP
RVDGLPDGAEATSDIPPGKTDLHLKALDGLAAPFAAFLDAACADGSTNKVDWLFLDSFQYWAAAAAADRK
IPCALILPFASSTLAEFGVPRLEPPVEGSTASILQRFVLTFEKCQLVIHRACSELEPEHTPLLPGIFGKP
VIQYGLVPPCPPAQGHIEHDNAALSWLDKQQPESVLFIALGSEPPVTVEQLHEIALGLELAGTTFLWALK
KPNGLLLEADGDILPPGFEERTRDRGLVAMGWVPQLSILAHSSVGAFLTHGGWSSTIEGAMSGHPMVFLT
FLDEQRINAQLIERKKAGLRVPRCEKDGSYDRQGIAGAIRAVMCEEESKSVFAANAKKMQEIINDRKCQE
RYIDELIQRLRSFEK SEQ ID NO: 13 (UGT40087-1 codon optimized nucleic acid sequence)
ATGGATGCTTCCAGTAGTCCTTTACACATCGTTATCTTTCCATGGTTAGCTTTCGGTCATATGTTGGCTTCCTTG
GAATTGGCTGAGAGATTGGCTGCTCGTGGTCACAGAGTCTCCTTCGTTTCCACCCCTAGAAACATCTCTAGATTA
CGTCCAGTTCCACCAGCTTTAGCTCCATTGATTGATTTTGTCGCTTTGCCACTAGAGTCGATGGTTTACCA
GATGGTGCCGAAGCTACCTCTGACATTCCACCAGGTAAGACCGAATTACACTTGAAGGCTTTGGACGGTTTGGCT
GCTCCATTCGCCGCTTTTTTGGACGCTGCCTGTGCTGATGGTTCCACCAACAAGGTTGATTGGTTGTTTTTGGAC
AACTTCCAATACTGGGCTGCCGCTGCCGCTGCTGATCACAAAATTCCTTGCGCCTTAAACTTGACTTTTGCCGCT
TCCACCTCCGCTGAATACGGTGTTCCACGTGTTGAACCACCAGTTGACGGTTCCACTGCCTCCATCTTACAAAGA
TTTGTCTTAACCTTAGAAAAATGTCAATTCGTTATCCAAAGAGCTTGTTTCGAATTGGAACCTGAACCATTGCCA
TTGTTGTCCGACATTTTCGGTAAGCCAGTCATCCCATACGGTTTAGTTCCTCCATGTCCACCAGCTGAAGGTCAC
AAAAGAGAACACGGTAACGCTGCTTTGTCCTGGTTGGATAAGCAACAACCAGAATCTGTTTTGTTCATCGCTTTG
GGTTCTGAACCACCTGTTACCGTCGAACAATTGCACGAAATCGCTTTGGGTTTAGAATTGGCCGGTACCACCTTC
TTGTGGGCCTTGAAAAAGCCAAACGGTTTGTTGTTAGAAGCCGATGGTGATATTTTGCCACCAGGTTTCGAAGAA
AGAACTAGAGATAGAGGTTTAGTCGCTATGGGTTGGGTTCCACAACCAATTATCTTGGCCCATTCCTCTGTTGGT
GCCTTTTTGACTCACGGTGGTTGGGCCTCCACTATTGAAGGTGTCATGTCCGGTCACCCTATGTTGTTCTTAACC
TTCTTGGACGAACAACGTATCAACGCCCAATTGATCGAAAGAAAAAAGGCTGGTTTAAGAGTCCCAAGAAGAGAA
AAGGATGGTTCCTACGACAGACAAGGTATTGCTGGTGCTATTAGAGCCGTCATGTGTGAAGAAGAATCTAAGTCT
GTCTTCGCTGCTAACGCTAAGAAAATGCAAGAGATCGTTTCTGACAGAAACTGTCAAGAAAGTACATCGACGAA
TTGATTCAAAGATTGGGTTCTTTCGAAAAGTAA SEQ ID NO: 14 (loop2 from Os_UGT_91C1)
EGLPDGAESTNDVPHDRPDMV SEQ ID NO: 15 (loop3_1 from Os_UGT_91C1)
SEFLGTACAD SEQ ID NO: 16 (loop3_2 from Os_UGT_91C1)
SEFLGTACADWVIVDVFHH SEQ ID NO: 17 (loop4_1 from Os_UGT_91C1)
ADRRLERAETESPAAAGQGRPAAAPTFEVARMKLIRTKGSSGM
```

SEQUENCE LISTING

SEQ ID NO: 18 (loop4_2 from Os_UGT_91C1)
MMLLGSAHMIASIADRRLERAETESPAAAGQGRPAAAPTFEVARMKLIRTKGSSGM SEQ ID NO: 19 (loop2 from UGT40087)
DGLPDGAEATSDIPPGKT SEQ ID NO: 20 (loop3_1 from UGT40087)
AAFLDAACADGSTNKVD SEQ ID NO: 21 (loop3_2 from UGT40087)
AAFLDAACADGSTNKVDWLFLDNFQY SEQ ID NO: 22 (loop4_1 from UGT40087)
GVPRVEPPVDGSTA SEQ ID NO: 23 (loop4_2 from UGT40087)
LNLTFAASTSAEYGVPRVEPPVDGSTA SEQ ID NO: 24 (UGT40087/Si91Dlike chimera)
MDASSSPLHIVIFPWLAFGHMLASLELAERLAARGHRVSFVSTPRNISRLRPVPPALAPLIDFVALPLPRVDGLP
DGAEATSDIPPGKTELHLKALDGLAAPFAAFLDAACADGSTNKVDWLFLDNFQYWAAAAAADHKIPCALNLTFAA
STSAEYGVPRVEPPVDGSTASILQRFVLTLEKCQFVIQRACFELEPEPLPLLSDIFGKPVIPYGLVPPCPPAQGH
IEHDNAALSWLDKQQPESVLFIALGSEPPVTVEQLHEIALGLELAGTTFLWALKKPNGLLLEADGDILPPGFEER
TRDRGLVAMGWVPQLSILAHSSVGAFLTHGGWSSTIEGAMSGHPMVFLTFLDEQRINAQLIERKKAGLRVPRCEK
DGSYDRQGIAGAIRAVMCEEESKSVFAANAKKMQEIINDRKCQERYIDELIQRLRSFEK SEQ ID NO: 25 (Os_UGT_91C1_loop4_1)
MDSGYSSSYAAAAGMHVVICPWLAFGHLLPCLDLAQRLASRGHRVSFVSTPRNISRLPPVRPALAPLVAFVALPL
PRVEGLPDGAESTNDVPHDRPDMVELHRRAFDGLAAPFSEFLGTACADWVIVDVFHHWAAAAALEHKVPCAMMLL
GSAHMIASIGVPRVEPPVDGSTASLAERFSLTLSRSSLVVGRSCVEFEPETVPLLSTLRGKPITFLGLMPPLHEG
RREDGEDATVRWLDAQPAKSVVYVALGSEVPLGVEKVHELALGLELAGTRFLWALRKPTGVSDADLLPAGFEERT
RGRGVVATRWVPQMSILAHAAVGAFLTHCGWNSTIEGLMFGHPLIMLPIFGDQGPNARLIEAKNAGLQVARNDGD
GSFDREGVAAAIRAVAVEEESSKVFQAKAKKLQEIVADMACHERYIDGFIQQLRSYKD SEQ ID NO: 26 (unoptimized nucleic acid sequence of UGT40087 having SEQ
ID NO: 1)
tcgtgacgca acagagcaac tctcgccggc accggtcgcc ccttccgcag gcaggcagca
ggctcgcgcg catggacgcc tccgactcct ccccgctgca catcgtcatc ttcccgtggc
tcgcgttcgg ccacatgctc gccagcctgg agctcgccga gcgcctggcc gcgcgaggcc
accgcgtgtc cttcgtctcc accccgcgca acatcagccg cctccgcccg gtcccgcccg
cgctggcgcc gctcatcgac ttcgtggcgc tgccgctgcc gcgcgtcgac ggcctccccg
acggcgcgga ggccaccagc gacatcccgc ccggcaagac cgagctccac ctcaaggccc
tagacggcct cgccgcgccc ttcgcagctt cctcgacgc cgcctgcgcc gacgggagca
ccaacaaggt ggactggctc ttcctcgaca acttccaata ctgggccgcc gccgccgctg
ccgaccataa gataccctgc gcgctgaacc tgacattcgc agcgtcgacg tcagcggagt
acggtgtgcc acgcgttgag ccgccggtgg atggctcaac agcctcaata ctccagcgat
ttgtgctaac cttggagaaa tgccagtttg tcatccaacg cgcctgcttc gagctggagc
cggagcccct gcctctcctg tcagacatct cggcaagcc ggtgatcccg tacggcctag
tcccgccgtg tccccccgca gaaggtcaca aagagagca cggcaacgca gctctgtcat
ggctcgacaa gcagcagccc gagtctgtcc tgttcattgc tctgggaagc gagcctccgg
tgaccgtcga acagctgcac gagatcgcgc ttgggctgga gctcgccggg acgacattcc
tctggctct gaagaagcct aacggcctcc tcctcgaggc ggacggcgac atcctgcccc
caggtttcga ggagcggacg cgtgaccgtg ggctcgtggc catgggctgg gttcctcagc
ccatcatact ggctcacagc tccgtgggcg cgttcctgac gcacggcgga tgggcctcca
ccattgaagg ggttatgtcc gggcatccca tgctcttcct gacgttctta gatgaacaga
ggataaacgc gcaactgatc gagaggaaga aggccgggtt gcgagtgcca aggcgtgaga
aggacggctc gtacgatcgc caaggcatcg ccggagcgat ccgggctgtc atgtgcgagg
aagaaagtaa gagcgtcttc gcggctaatg ccaagaagat gcaggagatt gtgagcgaca
ggaattgcca ggagaagtac atcgacgagc ttatccagcg tctgggatcc ttcgagaagt
gaaataaggt gaaatatcct acaataaccg cctgttgatg gcttgatgca acgatgtagg
tggccattcg cgcctctgat ctccatgttc ggcaataaa tccaccatat gttatggctc
tgacttactg aatttcctaa tatgtatgcc caaacacatg cataggttgc tagttgcccc
tcgcgccggc attagcgata atgtcaccgc agtcgccagc acaggtgtag caatttgaca
t SEQ ID NO: 27 (modified loop1 from Os_UGT_91C1 present in UGT40087_loop1)
TPRNISRLPPVPPALAP SEQ ID NO: 28 (modified loop1 from UGT40087 present in Os_UGT_91C1_loop1)
TPRNISRLRPVRPALAP -continued

SEQUENCE LISTING

SEQ ID NO: 29 (loop1 from Os_UGT_91C1 having SEQ ID NO: 8)
TPRNISRLPPVRPALAP

SEQ ID NO: 30 (loop1 from UGT40087 having SEQ ID NO: 11)
TPRNISRLRPVPPALAP

What is claimed:

1. A genetically modified yeast host cell comprising a heterologous nucleic acid encoding a UDP-glycosyltransferase, comprising an amino acid sequence having at least 80% sequence identity to SEQ ID NO: 1, wherein the genetically modified host cell is capable of converting rebaudioside A (RebA) to rebaudioside D (RebD) at an efficiency of greater than 90%.

2. The genetically modified host cell of claim 1, wherein the UDP-glycosyltransferase comprises an amino acid sequence having the sequence of SEQ ID NO:1.

3. The genetically modified host cell of claim 1, wherein the UDP-glycosyltransferase is capable of beta 1,2 glycosylation of the C2' position of the 19-O glucose of a steviol glycoside.

4. The genetically modified host cell of claim 1, wherein the UDP-glycosyltransferase is encoded by a heterologous nucleic acid, wherein the heterologous nucleic acid comprises a nucleotide sequence having at least 80% sequence identity to SEQ ID NO:13.

5. The genetically modified host cell of claim 1, wherein the UDP-glycosyltransferase is encoded by a heterologous nucleic acid having the sequence of SEQ ID NO:13.

6. The genetically modified host cell of claim 1, that is capable of converting RebA to RebD at an efficiency of greater than 90% and wherein the UDP-glycosyltransferase comprises an amino acid sequence having at least 95% sequence identity to SEQ ID NO:1.

7. The genetically modified host cell of claim 1, wherein the UDP-glycosyltransferase comprises the amino acid sequence SEQ ID NO:24.

8. The genetically modified host cell of claim 1, wherein the UDP-glycosyltransferase comprises an amino acid sequence having at least 92% sequence identity to SEQ ID NO:1.

9. The genetically modified host cell of claim 1 that is capable of producing RebD.

10. The genetically modified host cell of claim 1 that is capable of producing rebaudioside M (RebM).

11. The genetically modified host cell of claim 1 that is capable of producing at RebM and rebaudioside M2 (RebM2) at a ratio of at least 10:1, 100:1, or 1000:1.

12. The genetically modified host cell of claim 1, wherein the genetically modified host cell produces an undetectable level of RebM2.

13. The genetically modified host cell of claim 1, wherein the genetically modified host cell is capable of converting stevioside to rebaudioside E (RebE).

14. The genetically modified host cell of claim 1, wherein the genetically modified host cell further comprises one or more heterologous nucleic acids encoding one or more enzymes of a pathway for making steviol.

15. The genetically modified host cell of claim 1, wherein the genetically modified host cell further comprises one or more heterologous nucleic acids encoding one or more enzymes of a pathway for making a steviol glycoside.

16. The genetically modified host cell of claim 1, wherein the genetically modified host cell further comprises one or more heterologous nucleic acids encoding one or more enzymes of a pathway for making a RebA.

17. The genetically modified host cell of claim 1, wherein the genetically modified host cell further comprises one or more heterologous nucleic acids encoding one or more enzymes of a pathway for making RebM.

18. The genetically modified host cell of claim 1, wherein the genetically modified host cell further comprises one or more heterologous nucleic acids encoding one or more enzymes of a pathway for making RebE.

19. The genetically modified host cell of claim 14, wherein the one or more enzymes of the pathway comprise a geranylgeranyl diphosphate synthase.

20. The genetically modified host cell of claim 14, wherein the one or more enzymes of the pathway comprise a copalyl diphosphate synthase.

21. The genetically modified host cell of claim 14, wherein the one or more enzymes of the pathway comprise an ent-kaurene synthase.

22. The genetically modified host cell of claim 14, wherein the one or more enzymes of the pathway comprise a kaurene oxidase.

23. The genetically modified host cell of claim 14, wherein the one or more enzymes of the pathway comprise a kaurenoic acid hydroxylase.

24. The genetically modified host cell of claim 14, wherein the one or more enzymes of the pathway comprise a cytochrome P450 reductase.

25. The genetically modified host cell of claim 15, wherein the one or more enzymes of the pathway comprise a uridine 5'-diphospho glycosyltransferase.

26. The genetically modified host cell of claim 15, wherein the one or more enzymes of the pathway comprise UGT74G1 (SEQ ID NO: 31), UGT76G1 (SEQ ID NO: 32), UGT85C2 (SEQ ID NO: 33), and UGT91D (SEQ ID NO:7).

27. The genetically modified host cell of claim 15, wherein the one or more enzymes of the pathway comprise a geranylgeranyl diphosphate synthase, a copalyl diphosphate synthase, a ent-kaurene synthase, a kaurene oxidase, a kaurenoic acid hydroxylase, a cytochrome P450 reductase, UGT74G1 (SEQ ID NO: 31), UGT76G1 (SEQ ID NO: 32), UGT85C2 (SEQ ID NO: 33), and UGT91D (SEQ ID NO:7).

28. The genetically modified host cell of claim 14, wherein the one or more enzymes of the pathway comprises a bifunctional copalyl diphosphate synthase and kaurene synthase.

29. The genetically modified host cell of claim 27, wherein the one or more heterologous nucleic acids encoding one or more enzymes of the pathway are under control of a single transcriptional regulator.

30. The genetically modified host cell of claim 27, wherein the one or more heterologous nucleic acids encoding one or more enzymes of the pathway are under control of multiple heterologous transcriptional regulators.

31. The genetically modified host cell of claim 1, wherein the yeast is *Saccharomyces cerevisiae*.

32. A method for producing RebD:
(a) culturing a population of the genetically modified host cells claim 1 in a medium with a carbon source under conditions suitable for making RebD; and
(b) recovering said RebD compound from the medium.

33. A method for producing RebM:
(a) culturing a population of the genetically modified host cells claim 1 in a medium with a carbon source under conditions suitable for making RebM; and
(b) recovering said RebM compound from the medium.

34. The genetically modified host cell of claim 1, comprising a heterologous nucleic acid encoding a UDP-glycosyltransferase comprising an amino acid sequence having at least 85% sequence identity to SEQ ID NO:1.

35. The genetically modified host cell of claim 1, comprising a heterologous nucleic acid encoding a UDP-glycosyltransferase comprising an amino acid sequence having at least 90%, sequence identity to SEQ ID NO:1.

36. The genetically modified host cell of claim 1, comprising a heterologous nucleic acid encoding a UDP-glycosyltransferase comprising an amino acid sequence having at least 95% sequence identity to SEQ ID NO:1.

37. The genetically modified host cell of claim 1, wherein the UDP-glycosyltransferase is encoded by a heterologous nucleic acid, wherein the heterologous nucleic acid comprises a nucleotide sequence having at least 85% sequence identity to SEQ ID NO:13.

38. The genetically modified host cell of claim 1, wherein the UDP-glycosyltransferase is encoded by a heterologous nucleic acid, wherein the heterologous nucleic acid comprises a nucleotide sequence having at least 90% sequence identity to SEQ ID NO:13.

39. The genetically modified host cell of claim 1, wherein the UDP-glycosyltransferase is encoded by a heterologous nucleic acid, wherein the heterologous nucleic acid comprises a nucleotide sequence having at least 95% sequence identity to SEQ ID NO:13.

* * * * *

SEQUENCE LISTING

<160> NUMBER OF SEQ ID NOS: 33

<210> SEQ ID NO 1
<211> LENGTH: 436
<212> TYPE: PRT
<213> ORGANISM: Artificial Sequence
<220> FEATURE:
<223> OTHER INFORMATION: Synthetic: UGT40087 version 1

<400> SEQUENCE: 1

```
Met Asp Ala Ser Asp Ser Ser Pro Leu His Ile Val Ile Phe Pro Trp
1               5                   10                  15

Leu Ala Phe Gly His Met Leu Ala Ser Leu Glu Leu Ala Glu Arg Leu
            20                  25                  30

Ala Ala Arg Gly His Arg Val Ser Phe Val Ser Thr Pro Arg Asn Ile
        35                  40                  45

Ser Arg Leu Arg Pro Val Pro Pro Ala Leu Ala Pro Leu Ile Asp Phe
    50                  55                  60

Val Ala Leu Pro Leu Pro Arg Val Asp Gly Leu Pro Asp Gly Ala Glu
65                  70                  75                  80

Ala Thr Ser Asp Ile Pro Pro Gly Lys Thr Glu Leu His Leu Lys Ala
                85                  90                  95

Leu Asp Gly Leu Ala Ala Pro Phe Ala Ala Phe Leu Asp Ala Ala Cys
            100                 105                 110

Ala Asp Gly Ser Thr Asn Lys Val Asp Trp Leu Phe Leu Asp Asn Phe
        115                 120                 125

Gln Tyr Trp Ala Ala Ala Ala Ala Asp His Lys Ile Pro Cys Ala
    130                 135                 140

Leu Asn Leu Thr Phe Ala Ala Ser Thr Ser Ala Glu Tyr Gly Val Pro
145                 150                 155                 160

Arg Val Glu Pro Pro Val Asp Gly Ser Thr Ala Ser Ile Leu Gln Arg
                165                 170                 175

Phe Val Leu Thr Leu Glu Lys Cys Gln Phe Val Ile Gln Arg Ala Cys
            180                 185                 190

Phe Glu Leu Glu Pro Glu Pro Leu Pro Leu Leu Ser Asp Ile Phe Gly
        195                 200                 205

Lys Pro Val Ile Pro Tyr Gly Leu Val Pro Pro Cys Pro Pro Ala Glu
    210                 215                 220

Gly His Lys Arg Glu His Gly Asn Ala Ala Leu Ser Trp Leu Asp Lys
225                 230                 235                 240

Gln Gln Pro Glu Ser Val Leu Phe Ile Ala Leu Gly Ser Glu Pro Pro
                245                 250                 255

Val Thr Val Glu Gln Leu His Glu Ile Ala Leu Gly Leu Glu Leu Ala
            260                 265                 270

Gly Thr Thr Phe Leu Trp Ala Leu Lys Lys Pro Asn Gly Leu Leu Leu
        275                 280                 285
```

```
Glu Ala Asp Gly Asp Ile Leu Pro Pro Gly Phe Glu Arg Thr Arg
    290                 295                 300

Asp Arg Gly Leu Val Ala Met Gly Trp Val Pro Gln Pro Ile Ile Leu
305                 310                 315                 320

Ala His Ser Ser Val Gly Ala Phe Leu Thr His Gly Gly Trp Ala Ser
                325                 330                 335

Thr Ile Glu Gly Val Met Ser Gly His Pro Met Leu Phe Leu Thr Phe
            340                 345                 350

Leu Asp Glu Gln Arg Ile Asn Ala Gln Leu Ile Glu Arg Lys Lys Ala
        355                 360                 365

Gly Leu Arg Val Pro Arg Arg Glu Lys Asp Gly Ser Tyr Asp Arg Gln
    370                 375                 380

Gly Ile Ala Gly Ala Ile Arg Ala Val Met Cys Glu Glu Ser Lys
385                 390                 395                 400

Ser Val Phe Ala Ala Asn Ala Lys Lys Met Gln Glu Ile Val Ser Asp
                405                 410                 415

Arg Asn Cys Gln Glu Lys Tyr Ile Asp Glu Leu Ile Gln Arg Leu Gly
            420                 425                 430

Ser Phe Glu Lys
        435

<210> SEQ ID NO 2
<211> LENGTH: 449
<212> TYPE: PRT
<213> ORGANISM: Artificial Sequence
<220> FEATURE:
<223> OTHER INFORMATION: Synthetic: sr.UGT_g252778

<400> SEQUENCE: 2

Met Ala Thr Asn Asp Asp Arg Lys Gln Leu His Val Ala Met Phe
1               5                   10                  15

Pro Trp Leu Ala Phe Gly His Ile Leu Pro Phe Leu Glu Leu Ser Lys
            20                  25                  30

Leu Ile Ala Gln Asn Gly His Lys Val Ser Phe Leu Ser Thr Thr Arg
        35                  40                  45

Asn Ile Gln Arg Leu Pro Ser His Leu Thr Pro Leu Ile Asn Leu Val
    50                  55                  60

Lys Leu Thr Leu Pro Arg Val Gln Glu Leu Pro Glu Asp Ala Glu Ala
65                  70                  75                  80

Thr Thr Asp Ile Lys His Asp Gln Asp His Leu Leu Asn Ala Ser
                85                  90                  95

Asp Gly Leu Gln Pro Glu Val Thr Arg Phe Leu Glu Glu Ser Pro
            100                 105                 110

Asp Trp Ile Ile Phe Asp Tyr Ser Tyr Tyr Trp Leu Pro Pro Val Ala
        115                 120                 125

Ala Glu Leu Gly Ile Ser Arg Ala Phe Phe Met Thr Phe Pro Thr Trp
    130                 135                 140

Thr Met Ala Leu Thr Arg Leu Pro Ser Asp Gln Leu Thr Ala Glu Asp
145                 150                 155                 160

Leu Met Thr Leu Ser Lys Ile Ser Phe Lys Lys His Glu Ile Val Asn
                165                 170                 175

Leu Met Tyr Gly Thr Ser Thr Gln Gly Asp Leu Tyr Arg Leu Thr Met
            180                 185                 190

Ala Cys Asn Gly Ser Asp Cys Ile Leu Ile Arg Cys Cys Tyr Glu Phe
        195                 200                 205
```

Glu Pro Gln Trp Leu Thr Leu Leu Glu Lys Leu Leu Pro Val Pro Val
    210                 215                 220

Val Pro Val Gly Leu Leu Pro Pro Glu Ile His Gly Asp Glu Lys Asp
225                 230                 235                 240

Asp Asp Thr Trp Val Ser Val Lys Glu Trp Leu Asp Gly Gln His Lys
                245                 250                 255

Gly His Val Val Tyr Val Ala Leu Gly Ser Glu Ala Met Val Ser Lys
            260                 265                 270

Asp Glu Leu Gly Glu Leu Ala Leu Gly Leu Glu Leu Ser Gly Leu Pro
        275                 280                 285

Phe Phe Trp Ala Leu Arg Lys Pro Pro Gly Ser Thr Glu Ser Asp Ser
290                 295                 300

Val Glu Leu Pro Asp Gly Phe Met Glu Arg Thr Arg Asn Arg Gly Val
305                 310                 315                 320

Val Trp Thr Ser Trp Ala Pro Gln Leu Arg Ile Leu Ser His Glu Ser
                325                 330                 335

Val Cys Gly Phe Leu Thr His Cys Gly Val Ser Ser Ile Val Glu Gly
            340                 345                 350

Leu Met Phe Gly His Pro Leu Ile Met Leu Pro Ile Phe Gly Asp Gln
        355                 360                 365

Ile Met Asn Ala Gln Val Leu Ala Asp Lys Gln Val Gly Ile Glu Ile
370                 375                 380

Pro Arg Asn Glu Glu Asp Gly Trp Phe Thr Lys Glu Ser Val Ala Lys
385                 390                 395                 400

Ser Leu Arg Ser Val Val Asp Asp Glu Gly Glu Ile Tyr Lys Ala
                405                 410                 415

Asn Ala Arg Glu Leu Ser Lys Ile Phe Ser Asp Thr Asp Leu Gly Lys
            420                 425                 430

Lys Tyr Ile Ser His Phe Ile Asp Phe Leu Met Met Glu Ile Val Lys
        435                 440                 445

Thr

<210> SEQ ID NO 3
<211> LENGTH: 460
<212> TYPE: PRT
<213> ORGANISM: Artificial Sequence
<220> FEATURE:
<223> OTHER INFORMATION: Synthetic: Bd_UGT10840

<400> SEQUENCE: 3

Met Asp Asn Gly Ser Ser Ser Ser Ser Ser Pro Leu His Val Val
1               5                   10                  15

Ile Cys Pro Trp Leu Ala Phe Gly His Gln Leu Pro Cys Leu Asp Leu
                20                  25                  30

Ala Glu Arg Leu Ala Leu Arg Gly His Arg Val Ser Phe Val Ser Thr
            35                  40                  45

Pro Arg Ile Ile Ala Arg Leu Pro Pro Val Arg Pro Val Ala Ala Ser
        50                  55                  60

Leu Val Asp Leu Val Ala Leu Pro Leu Pro Arg Val Asp Gly Leu Pro
65                  70                  75                  80

Glu Gly Ala Glu Ser Thr Asn Asp Val Pro Tyr Glu Lys Phe Glu Leu
                85                  90                  95

His Arg Lys Ala Phe Asp Gly Leu Ala Val Pro Phe Ser Glu Phe Leu
            100                 105                 110

```
Arg Ala Ala Cys Ala Glu Glu Gly Lys Lys Pro Asp Trp Ile Ile Val
            115                 120                 125

Asp Thr Phe His His Trp Ala Ala Ala Ala Ile Glu His Lys Val
    130                 135                 140

Pro Cys Ala Met Leu Met Leu Gly Ala Ala Gly Leu Ile Val Ala Trp
145                 150                 155                 160

Ala Thr Gln Pro Ser Lys His Val Thr Ser Glu Gln Glu Gln Ser
            165                 170                 175

Ala Ala Glu Pro Pro Arg Phe Glu Thr Glu Arg Arg Lys Leu Ala Thr
            180                 185                 190

Thr Gln Arg Ala Ser Gly Met Ser Ile Ala Glu Arg Cys Ser Val Thr
            195                 200                 205

Leu Glu Arg Cys Asn Leu Val Ala Met Arg Ser Cys Leu Glu Trp Glu
    210                 215                 220

Pro Glu Ser Ile Pro Leu Ala Thr Thr Ile Gly Gly Lys Gln Leu Val
225                 230                 235                 240

Pro Leu Gly Leu Leu Pro Pro Ser Pro Glu Gly Gly Arg Gly Val Ser
            245                 250                 255

Lys Glu Asp Ala Thr Val Arg Trp Leu Asp Ala Gln Pro Thr Lys Ser
            260                 265                 270

Val Val Tyr Val Ala Leu Gly Ser Glu Val Pro Leu Gly Ala Lys Glu
            275                 280                 285

Val His Glu Leu Ala Leu Gly Leu Glu Leu Ala Gly Thr Arg Phe Leu
            290                 295                 300

Trp Ser Leu Arg Lys Pro Ser Gly Val Ser Asp Ala Asp Ile Leu Pro
305                 310                 315                 320

Ser Gly Phe Glu Glu Arg Thr Arg Gly Arg Gly Leu Val Thr Met Gly
            325                 330                 335

Trp Val Pro Gln Ile Ser Val Leu Ala His Gly Ala Val Gly Ala Phe
            340                 345                 350

Leu Thr His Cys Gly Trp Asn Ser Ile Ile Glu Gly Leu Gln Phe Gly
            355                 360                 365

His Pro Leu Val Met Leu Pro Ile Phe Gly Asp Gln Gly Pro Asn Ala
            370                 375                 380

Arg Met Met Glu Gly Arg Lys Val Gly Val Gln Val Pro Arg Asp Glu
385                 390                 395                 400

Ser Asn Gly Ser Phe Asp Arg Glu Gly Val Ala Thr Thr Val Arg Ala
            405                 410                 415

Val Ala Val Glu Glu Glu Gly Asn Arg Ile Phe Thr Ala Asn Ala Lys
            420                 425                 430

Lys Met Gln Glu Ile Val Ala Asp Lys Gly Cys His Asp Lys Tyr Val
            435                 440                 445

Asp Lys Phe Ile Gln Lys Leu Arg Ser Tyr Met Glu
            450                 455                 460

<210> SEQ ID NO 4
<211> LENGTH: 463
<212> TYPE: PRT
<213> ORGANISM: Artificial Sequence
<220> FEATURE:
<223> OTHER INFORMATION: Synthetic: Hv_UGT_V1

<400> SEQUENCE: 4

Met Asp Gly Asp Gly Asn Ser Ser Ser Ser Ser Pro Leu His Val
1               5                   10                  15
```

```
Val Ile Cys Pro Trp Leu Ala Leu Gly His Leu Pro Cys Leu Asp
             20                  25                  30

Ile Ala Glu Arg Leu Ala Ser Arg Gly His Arg Val Ser Phe Val Ser
             35                  40                  45

Thr Pro Arg Asn Ile Ala Arg Leu Pro Pro Leu Arg Pro Ala Val Ala
 50                  55                  60

Pro Leu Val Glu Phe Val Ala Leu Pro Leu Pro His Val Asp Gly Leu
 65                  70                  75                  80

Pro Glu Gly Ala Glu Ser Thr Asn Asp Val Pro Tyr Asp Lys Phe Glu
                 85                  90                  95

Leu His Arg Lys Ala Phe Asp Gly Leu Ala Ala Pro Phe Ser Glu Phe
                100                 105                 110

Leu Arg Ala Ala Cys Ala Glu Gly Ala Gly Ser Arg Pro Asp Trp Leu
            115                 120                 125

Ile Val Asp Thr Phe His His Trp Ala Ala Ala Ala Val Glu Asn
            130                 135                 140

Lys Val Pro Cys Val Met Leu Leu Leu Gly Ala Ala Thr Val Ile Ala
145                 150                 155                 160

Gly Phe Ala Arg Gly Val Ser Glu His Ala Ala Ala Val Gly Lys
                165                 170                 175

Glu Arg Pro Ala Ala Glu Ala Pro Ser Phe Glu Thr Glu Arg Arg Lys
            180                 185                 190

Leu Met Thr Thr Gln Asn Ala Ser Gly Met Thr Val Ala Glu Arg Tyr
            195                 200                 205

Phe Leu Thr Leu Met Arg Ser Asp Leu Val Ala Ile Arg Ser Cys Ala
210                 215                 220

Glu Trp Glu Pro Glu Ser Val Ala Ala Leu Thr Thr Leu Ala Gly Lys
225                 230                 235                 240

Pro Val Val Pro Leu Gly Leu Leu Pro Pro Ser Pro Glu Gly Gly Arg
                245                 250                 255

Gly Val Ser Lys Glu Asp Ala Ala Val Arg Trp Leu Asp Ala Gln Pro
            260                 265                 270

Ala Lys Ser Val Val Tyr Val Ala Leu Gly Ser Glu Val Pro Leu Arg
            275                 280                 285

Ala Glu Gln Val His Glu Leu Ala Leu Gly Leu Glu Leu Ser Gly Ala
            290                 295                 300

Arg Phe Leu Trp Ala Leu Arg Lys Pro Thr Asp Ala Pro Asp Ala Ala
305                 310                 315                 320

Val Leu Pro Pro Gly Phe Glu Glu Arg Thr Gly Arg Gly Leu Val
                325                 330                 335

Val Thr Gly Trp Val Pro Gln Ile Gly Val Leu Ala His Gly Ala Val
            340                 345                 350

Ala Ala Phe Leu Thr His Cys Gly Trp Asn Ser Thr Ile Glu Gly Leu
            355                 360                 365

Leu Phe Gly His Pro Leu Ile Met Leu Pro Ile Ser Ser Asp Gln Gly
            370                 375                 380

Pro Asn Ala Arg Leu Met Glu Gly Arg Lys Val Gly Met Gln Val Pro
385                 390                 395                 400

Arg Asp Glu Ser Asp Gly Ser Phe Arg Glu Asp Val Ala Ala Thr
                405                 410                 415

Val Arg Ala Val Ala Val Glu Glu Asp Gly Arg Arg Val Phe Thr Ala
            420                 425                 430

Asn Ala Lys Lys Met Gln Glu Ile Val Ala Asp Gly Ala Cys His Glu
```

```
            435                 440                 445
Arg Cys Ile Asp Gly Phe Ile Gln Gln Leu Arg Ser Tyr Lys Ala
        450                 455                 460
```

<210> SEQ ID NO 5
<211> LENGTH: 464
<212> TYPE: PRT
<213> ORGANISM: Artificial Sequence
<220> FEATURE:
<223> OTHER INFORMATION: Synthetic: Bd_UGT10850

<400> SEQUENCE: 5

```
Met Asp Ala Ala Gly Ser Ser Pro Met His Ile Val Ile Phe Pro
1               5                   10                  15

Trp Leu Ala Ser Gly His Leu Leu Pro Cys Leu Glu Leu Ala Glu Arg
            20                  25                  30

Leu Ala Ala Arg Gly His Leu Val Ser Phe Val Ser Thr Pro Arg Asn
            35                  40                  45

Leu Ala Arg Leu Pro Pro Val Ser Pro Ala Leu Ala Pro Leu Val Asp
        50                  55                  60

Leu Val Ala Leu Pro Leu Pro Arg Val Ala Gly Leu Pro Asp Gly Ala
65                  70                  75                  80

Glu Ser Thr Ala Asp Val Pro Ala Asp Lys Phe Asp Leu His Arg Gln
                85                  90                  95

Ala Phe Asp Gly Leu Ala Ala Pro Phe Ala Ala Phe Leu Asp Ala Asp
            100                 105                 110

Val Gly Lys Lys Lys Lys Pro Asp Trp Ile Val Ala Asp Phe Val His
            115                 120                 125

His Trp Val Ala Ala Ala Gln Glu Arg Glu Val Pro Cys Ala Met
        130                 135                 140

Leu Val Pro Cys Ala Ala Ala Val Ala Val Leu Ala Gly Pro Pro Pro
145                 150                 155                 160

Glu Ser Ile Ser Asn Ala Asp Glu Arg Gln Val Ile Val Lys Val Met
                165                 170                 175

Asp Ala Ala Pro Arg Phe Glu Ala Glu Gln Ala Met Glu Glu Phe Ala
            180                 185                 190

Ala Glu Asp Ala Ser Gly Ser Ser Gly Leu Ser Val Leu Ser Arg
        195                 200                 205

Phe Tyr Met Thr Leu Lys Arg Cys Lys Val Val Ala Leu Arg Ser Cys
210                 215                 220

Pro Glu Leu Glu Pro Asp Ala Phe Pro Leu Leu Thr Arg Leu Tyr Gly
225                 230                 235                 240

Lys Pro Ala Val Pro Leu Gly Leu Leu Pro Pro Pro Asn Gly Thr
                245                 250                 255

Arg Ser Arg Gly Met Asp Asp Glu Ala Ile Ile Arg Trp Leu Asn Ala
            260                 265                 270

Gln Pro Ala Ser Ser Val Val Tyr Val Ala Leu Gly Ser Glu Ala Pro
        275                 280                 285

Leu Arg Ala Glu Leu Leu Arg Glu Leu Ala His Gly Leu Glu Leu Ala
    290                 295                 300

Gly Thr Arg Phe Leu Trp Ala Leu Arg Lys Pro Val Gly Val Gln Asp
305                 310                 315                 320

Gly Asp Ser Val Leu Pro Asp Gly Phe Val Glu Arg Thr Ser Arg Arg
                325                 330                 335

Gly Leu Val Val Ala Arg Trp Val Ser Gln Val Ser Ile Leu Ala His
```

```
                    340                 345                 350
Gly Ala Val Gly Ala Phe Leu Thr His Cys Gly Trp Gly Ser Val Val
                355                 360                 365
Glu Gly Leu Gln Phe Gly Arg Pro Leu Ile Met Leu Pro Ile Ala Gly
        370                 375                 380
Asp Gln Gly Pro Asn Ala Arg Leu Met Glu Glu Arg Lys Val Gly Val
385                 390                 395                 400
Ser Val Pro Arg Asp Glu Lys Asp Gly Ser Phe Thr Arg Gly Gly Val
                405                 410                 415
Ala Gly Ala Ile Arg Ala Val Val Glu Glu Asp Gly Arg Leu Phe
                420                 425                 430
Ala Ala Asn Ala Glu Lys Leu Arg Glu Ile Val Ala Ser Arg Glu Cys
            435                 440                 445
His Glu Arg Cys Ile Asp Gly Phe Ile Gln His Leu Arg Cys Cys Lys
        450                 455                 460
```

<210> SEQ ID NO 6
<211> LENGTH: 464
<212> TYPE: PRT
<213> ORGANISM: Artificial Sequence
<220> FEATURE:
<223> OTHER INFORMATION: Synthetic: Ob_UGT91B1_like

<400> SEQUENCE: 6

```
Met Glu Asn Gly Ser Ser Pro Leu His Val Ile Phe Pro Trp Leu
1                   5                   10                  15
Ala Phe Gly His Leu Leu Pro Phe Leu Asp Leu Ala Glu Arg Leu Ala
                20                  25                  30
Ala Arg Gly His Arg Val Ser Phe Val Ser Thr Pro Arg Asn Leu Ala
            35                  40                  45
Arg Leu Arg Pro Val Arg Pro Ala Leu Arg Gly Leu Val Asp Leu Val
        50                  55                  60
Ala Leu Pro Leu Pro Arg Val His Gly Leu Pro Asp Gly Ala Glu Ala
65                  70                  75                  80
Thr Ser Asp Val Pro Phe Glu Lys Phe Glu Leu His Arg Lys Ala Phe
                85                  90                  95
Asp Gly Leu Ala Ala Pro Phe Ser Ala Phe Leu Asp Ala Ala Cys Ala
            100                 105                 110
Gly Asp Lys Arg Pro Asp Trp Val Ile Pro Asp Phe Met His Tyr Trp
        115                 120                 125
Val Ala Ala Ala Gln Lys Arg Gly Val Pro Cys Ala Val Leu Ile
    130                 135                 140
Pro Cys Ser Ala Asp Val Met Ala Leu Tyr Gly Gln Pro Thr Glu Thr
145                 150                 155                 160
Ser Thr Glu Gln Pro Glu Ala Ile Ala Arg Ser Met Ala Ala Glu Ala
                165                 170                 175
Pro Ser Phe Glu Ala Glu Arg Asn Thr Glu Tyr Gly Thr Ala Gly
            180                 185                 190
Ala Ser Gly Val Ser Ile Met Thr Arg Phe Ser Leu Thr Leu Lys Trp
        195                 200                 205
Ser Lys Leu Val Ala Leu Arg Ser Cys Pro Glu Leu Glu Pro Gly Val
    210                 215                 220
Phe Thr Thr Leu Thr Arg Val Tyr Ser Lys Pro Val Val Pro Phe Gly
225                 230                 235                 240
Leu Leu Pro Pro Arg Arg Asp Gly Ala His Gly Val Arg Lys Asn Gly
```

```
                         245                 250                 255
Glu Asp Asp Gly Ala Ile Ile Arg Trp Leu Asp Glu Gln Pro Ala Lys
                260                 265                 270

Ser Val Val Tyr Val Ala Leu Gly Ser Glu Ala Pro Val Ser Ala Asp
            275                 280                 285

Leu Leu Arg Glu Leu Ala His Gly Leu Glu Leu Ala Gly Thr Arg Phe
        290                 295                 300

Leu Trp Ala Leu Arg Arg Pro Ala Gly Val Asn Asp Gly Asp Ser Ile
305                 310                 315                 320

Leu Pro Asn Gly Phe Leu Glu Arg Thr Gly Glu Arg Gly Leu Val Thr
                325                 330                 335

Thr Gly Trp Val Pro Gln Val Ser Ile Leu Ala His Ala Ala Val Cys
            340                 345                 350

Ala Phe Leu Thr His Cys Gly Trp Gly Ser Val Val Glu Gly Leu Gln
        355                 360                 365

Phe Gly His Pro Leu Ile Met Leu Pro Ile Ile Gly Asp Gln Gly Pro
    370                 375                 380

Asn Ala Arg Phe Leu Glu Gly Arg Lys Val Gly Val Ala Val Pro Arg
385                 390                 395                 400

Asn His Ala Asp Gly Ser Phe Asp Arg Ser Gly Val Ala Gly Ala Val
                405                 410                 415

Arg Ala Val Ala Val Glu Glu Gly Lys Ala Phe Ala Ala Asn Ala
            420                 425                 430

Arg Lys Leu Gln Glu Ile Val Ala Asp Arg Glu Arg Asp Glu Arg Cys
        435                 440                 445

Thr Asp Gly Phe Ile His His Leu Thr Ser Trp Asn Glu Leu Glu Ala
    450                 455                 460

<210> SEQ ID NO 7
<211> LENGTH: 485
<212> TYPE: PRT
<213> ORGANISM: Artificial Sequence
<220> FEATURE:
<223> OTHER INFORMATION: Synthetic: UGT91D_like3

<400> SEQUENCE: 7

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
                20                  25                  30

Trp Leu Ala Phe Gly His Ile Leu Pro Tyr Leu Gln Leu Ser Lys Leu
            35                  40                  45

Ile Ala Glu Lys Gly His Lys Val Ser Phe Leu Ser Thr Thr Arg Asn
        50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
        115                 120                 125

Trp Ile Ile Tyr Asp Tyr Thr His Tyr Trp Leu Pro Ser Ile Ala Ala
    130                 135                 140

Ser Leu Gly Ile Ser Arg Ala His Phe Ser Val Thr Thr Pro Trp Ala
```

```
            145                 150                 155                 160
        Ile Ala Tyr Met Gly Pro Ser Ala Asp Ala Met Ile Asn Gly Ser Asp
                        165                 170                 175

Gly Arg Thr Thr Val Glu Asp Leu Thr Thr Pro Pro Lys Trp Phe Pro
                        180                 185                 190

Phe Pro Thr Lys Val Cys Trp Arg Lys His Asp Leu Ala Arg Leu Val
                        195                 200                 205

Pro Tyr Lys Ala Pro Gly Ile Ser Asp Gly Tyr Arg Met Gly Leu Val
                    210                 215                 220

Leu Lys Gly Ser Asp Cys Leu Leu Ser Lys Cys Tyr His Glu Phe Gly
        225                 230                 235                 240

Thr Gln Trp Leu Pro Leu Leu Glu Thr Leu His Gln Val Pro Val Val
                        245                 250                 255

Pro Val Gly Leu Leu Pro Pro Glu Ile Pro Gly Asp Glu Lys Asp Glu
                    260                 265                 270

Thr Trp Val Ser Ile Lys Lys Trp Leu Asp Gly Lys Gln Lys Gly Ser
                    275                 280                 285

Val Val Tyr Val Ala Leu Gly Ser Glu Val Leu Val Ser Gln Thr Glu
                    290                 295                 300

Val Val Glu Leu Ala Leu Gly Leu Glu Leu Ser Gly Leu Pro Phe Val
        305                 310                 315                 320

Trp Ala Tyr Arg Lys Pro Lys Gly Pro Ala Lys Ser Asp Ser Val Glu
                        325                 330                 335

Leu Pro Asp Gly Phe Val Glu Arg Thr Arg Asp Arg Gly Leu Val Trp
                        340                 345                 350

Thr Ser Trp Ala Pro Gln Leu Arg Ile Leu Ser His Glu Ser Val Cys
                    355                 360                 365

Gly Phe Leu Thr His Cys Gly Ser Gly Ser Ile Val Glu Gly Leu Met
                    370                 375                 380

Phe Gly His Pro Leu Ile Met Leu Pro Ile Phe Gly Asp Gln Pro Leu
        385                 390                 395                 400

Asn Ala Arg Leu Leu Glu Asp Lys Gln Val Gly Ile Glu Ile Pro Arg
                        405                 410                 415

Asn Glu Glu Asp Gly Cys Leu Thr Lys Glu Ser Val Ala Arg Ser Leu
                        420                 425                 430

Arg Ser Val Val Glu Lys Glu Gly Glu Ile Tyr Lys Ala Asn Ala
                    435                 440                 445

Arg Glu Leu Ser Lys Ile Tyr Asn Asp Thr Lys Val Glu Lys Glu Tyr
                    450                 455                 460

Val Ser Gln Phe Val Asp Tyr Leu Glu Lys Asn Ala Arg Ala Val Ala
        465                 470                 475                 480

Ile Asp His Glu Ser
                    485

<210> SEQ ID NO 8
<211> LENGTH: 462
<212> TYPE: PRT
<213> ORGANISM: Artificial Sequence
<220> FEATURE:
<223> OTHER INFORMATION: Synthetic: Os_UGT_91C1

<400> SEQUENCE: 8

Met Asp Ser Gly Tyr Ser Ser Ser Tyr Ala Ala Ala Ala Gly Met His
1               5                   10                  15

Val Val Ile Cys Pro Trp Leu Ala Phe Gly His Leu Leu Pro Cys Leu
```

-continued

```
                20                  25                  30
Asp Leu Ala Gln Arg Leu Ala Ser Arg Gly His Arg Val Ser Phe Val
            35                  40                  45
Ser Thr Pro Arg Asn Ile Ser Arg Leu Pro Pro Val Arg Pro Ala Leu
50                  55                  60
Ala Pro Leu Val Ala Phe Val Ala Leu Pro Leu Pro Arg Val Glu Gly
65                  70                  75                  80
Leu Pro Asp Gly Ala Glu Ser Thr Asn Asp Val Pro His Asp Arg Pro
                85                  90                  95
Asp Met Val Glu Leu His Arg Arg Ala Phe Asp Gly Leu Ala Ala Pro
            100                 105                 110
Phe Ser Glu Phe Leu Gly Thr Ala Cys Ala Asp Trp Val Ile Val Asp
            115                 120                 125
Val Phe His His Trp Ala Ala Ala Ala Leu Glu His Lys Val Pro
            130                 135                 140
Cys Ala Met Met Leu Leu Gly Ser Ala His Met Ile Ala Ser Ile Ala
145                 150                 155                 160
Asp Arg Arg Leu Glu Arg Ala Glu Thr Glu Ser Pro Ala Ala Ala Gly
            165                 170                 175
Gln Gly Arg Pro Ala Ala Ala Pro Thr Phe Glu Val Ala Arg Met Lys
            180                 185                 190
Leu Ile Arg Thr Lys Gly Ser Ser Gly Met Ser Leu Ala Glu Arg Phe
            195                 200                 205
Ser Leu Thr Leu Ser Arg Ser Ser Leu Val Val Gly Arg Ser Cys Val
            210                 215                 220
Glu Phe Glu Pro Glu Thr Val Pro Leu Leu Ser Thr Leu Arg Gly Lys
225                 230                 235                 240
Pro Ile Thr Phe Leu Gly Leu Met Pro Pro Leu His Glu Gly Arg Arg
            245                 250                 255
Glu Asp Gly Glu Asp Ala Thr Val Arg Trp Leu Asp Ala Gln Pro Ala
            260                 265                 270
Lys Ser Val Val Tyr Val Ala Leu Gly Ser Glu Val Pro Leu Gly Val
            275                 280                 285
Glu Lys Val His Glu Leu Ala Leu Gly Leu Glu Leu Ala Gly Thr Arg
            290                 295                 300
Phe Leu Trp Ala Leu Arg Lys Pro Thr Gly Val Ser Asp Ala Asp Leu
305                 310                 315                 320
Leu Pro Ala Gly Phe Glu Glu Arg Thr Arg Gly Arg Gly Val Val Ala
            325                 330                 335
Thr Arg Trp Val Pro Gln Met Ser Ile Leu Ala His Ala Ala Val Gly
            340                 345                 350
Ala Phe Leu Thr His Cys Gly Trp Asn Ser Thr Ile Glu Gly Leu Met
            355                 360                 365
Phe Gly His Pro Leu Ile Met Leu Pro Ile Phe Gly Asp Gln Gly Pro
            370                 375                 380
Asn Ala Arg Leu Ile Glu Ala Lys Asn Ala Gly Leu Gln Val Ala Arg
385                 390                 395                 400
Asn Asp Gly Asp Gly Ser Phe Asp Arg Glu Gly Val Ala Ala Ala Ile
            405                 410                 415
Arg Ala Val Ala Val Glu Glu Glu Ser Ser Lys Val Phe Gln Ala Lys
            420                 425                 430
Ala Lys Lys Leu Gln Glu Ile Val Ala Asp Met Ala Cys His Glu Arg
            435                 440                 445
```

```
Tyr Ile Asp Gly Phe Ile Gln Gln Leu Arg Ser Tyr Lys Asp
    450                 455                 460

<210> SEQ ID NO 9
<211> LENGTH: 442
<212> TYPE: PRT
<213> ORGANISM: Artificial Sequence
<220> FEATURE:
<223> OTHER INFORMATION: Synthetic: Sl_UGT_101249881

<400> SEQUENCE: 9

Met Ala Thr Asn Leu Arg Val Leu Met Phe Pro Trp Leu Ala Tyr Gly
1               5                   10                  15

His Ile Ser Pro Phe Leu Asn Ile Ala Lys Gln Leu Ala Asp Arg Gly
            20                  25                  30

Phe Leu Ile Tyr Leu Cys Ser Thr Arg Ile Asn Leu Glu Ser Ile Ile
        35                  40                  45

Lys Lys Ile Pro Glu Lys Tyr Ala Asp Ser Ile His Leu Ile Glu Leu
    50                  55                  60

Gln Leu Pro Glu Leu Pro Glu Leu Pro Pro His Tyr His Thr Thr Asn
65                  70                  75                  80

Gly Leu Pro Pro His Leu Asn Pro Thr Leu His Lys Ala Leu Lys Met
                85                  90                  95

Ser Lys Pro Asn Phe Ser Arg Ile Leu Gln Asn Leu Lys Pro Asp Leu
            100                 105                 110

Leu Ile Tyr Asp Val Leu Gln Pro Trp Ala Glu His Val Ala Asn Glu
        115                 120                 125

Gln Asn Ile Pro Ala Gly Lys Leu Leu Thr Ser Cys Ala Ala Val Phe
    130                 135                 140

Ser Tyr Phe Phe Ser Phe Arg Lys Asn Pro Gly Val Glu Phe Pro Phe
145                 150                 155                 160

Pro Ala Ile His Leu Pro Glu Val Glu Lys Val Lys Ile Arg Glu Ile
                165                 170                 175

Leu Ala Lys Glu Pro Glu Glu Gly Gly Arg Leu Asp Glu Gly Asn Lys
            180                 185                 190

Gln Met Met Leu Met Cys Thr Ser Arg Thr Ile Glu Ala Lys Tyr Ile
        195                 200                 205

Asp Tyr Cys Thr Glu Leu Cys Asn Trp Lys Val Pro Val Gly Pro
    210                 215                 220

Pro Phe Gln Asp Leu Ile Thr Asn Asp Ala Asp Asn Lys Glu Leu Ile
225                 230                 235                 240

Asp Trp Leu Gly Thr Lys His Glu Asn Ser Thr Val Phe Val Ser Phe
                245                 250                 255

Gly Ser Glu Tyr Phe Leu Ser Lys Glu Asp Met Glu Glu Val Ala Phe
            260                 265                 270

Ala Leu Glu Leu Ser Asn Val Asn Phe Ile Trp Val Ala Arg Phe Pro
        275                 280                 285

Lys Gly Glu Glu Arg Asn Leu Glu Asp Ala Leu Pro Lys Gly Phe Leu
    290                 295                 300

Glu Arg Ile Gly Glu Arg Gly Arg Val Leu Asp Lys Phe Ala Pro Gln
305                 310                 315                 320

Pro Arg Ile Leu Asn His Pro Ser Thr Gly Gly Phe Ile Ser His Cys
                325                 330                 335

Gly Trp Asn Ser Ala Met Glu Ser Ile Asp Phe Gly Val Pro Ile Ile
            340                 345                 350
```

```
Ala Met Pro Ile His Asn Asp Gln Pro Ile Asn Ala Lys Leu Met Val
            355                 360                 365

Glu Leu Gly Val Ala Val Glu Ile Val Arg Asp Asp Gly Lys Ile
370                 375                 380

His Arg Gly Glu Ile Ala Glu Thr Leu Lys Ser Val Val Thr Gly Glu
385                 390                 395                 400

Thr Gly Glu Ile Leu Arg Ala Lys Val Arg Glu Ile Ser Lys Asn Leu
                405                 410                 415

Lys Ser Ile Arg Asp Glu Glu Met Asp Ala Val Ala Glu Glu Leu Ile
                420                 425                 430

Gln Leu Cys Arg Asn Ser Asn Lys Ser Lys
            435                 440
```

<210> SEQ ID NO 10
<211> LENGTH: 500
<212> TYPE: PRT
<213> ORGANISM: Artificial Sequence
<220> FEATURE:
<223> OTHER INFORMATION: Synthetic: Sr.KAH

<400> SEQUENCE: 10

```
Met Glu Ala Ser Tyr Leu Tyr Ile Ser Ile Leu Leu Leu Leu Ala Ser
1               5                   10                  15

Tyr Leu Phe Thr Thr Gln Leu Arg Arg Lys Ser Ala Asn Leu Pro Pro
                20                  25                  30

Thr Val Phe Pro Ser Ile Pro Ile Ile Gly His Leu Tyr Leu Leu Lys
            35                  40                  45

Lys Pro Leu Tyr Arg Thr Leu Ala Lys Ile Ala Ala Lys Tyr Gly Pro
50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95

Asn Arg Pro Lys Thr Leu Phe Gly Lys Ile Val Gly Gly Thr Ser Leu
                100                 105                 110

Gly Ser Leu Ser Tyr Gly Asp Gln Trp Arg Asn Leu Arg Arg Val Ala
            115                 120                 125

Ser Ile Glu Ile Leu Ser Val His Arg Leu Asn Glu Phe His Asp Ile
            130                 135                 140

Arg Val Asp Glu Asn Arg Leu Leu Ile Arg Lys Leu Arg Ser Ser Ser
145                 150                 155                 160

Ser Pro Val Thr Leu Ile Thr Val Phe Tyr Ala Leu Thr Leu Asn Val
                165                 170                 175

Ile Met Arg Met Ile Ser Gly Lys Arg Tyr Phe Asp Ser Gly Asp Arg
                180                 185                 190

Glu Leu Glu Glu Glu Gly Lys Arg Phe Arg Glu Ile Leu Asp Glu Thr
            195                 200                 205

Leu Leu Leu Ala Gly Ala Ser Asn Val Gly Asp Tyr Leu Pro Ile Leu
    210                 215                 220

Asn Trp Leu Gly Val Lys Ser Leu Glu Lys Lys Leu Ile Ala Leu Gln
225                 230                 235                 240

Lys Lys Arg Asp Asp Phe Phe Gln Gly Leu Ile Glu Gln Val Arg Lys
                245                 250                 255

Ser Arg Gly Ala Lys Val Gly Lys Gly Arg Lys Thr Met Ile Glu Leu
                260                 265                 270
```

```
Leu Leu Ser Leu Gln Glu Ser Glu Pro Glu Tyr Tyr Thr Asp Ala Met
        275                 280                 285

Ile Arg Ser Phe Val Leu Gly Leu Ala Ala Gly Ser Asp Thr Ser
    290                 295                 300

Ala Gly Thr Met Glu Trp Ala Met Ser Leu Leu Val Asn His Pro His
305                 310                 315                 320

Val Leu Lys Lys Ala Gln Ala Glu Ile Asp Arg Val Ile Gly Asn Asn
                325                 330                 335

Arg Leu Ile Asp Glu Ser Asp Ile Gly Asn Ile Pro Tyr Ile Gly Cys
                340                 345                 350

Ile Ile Asn Glu Thr Leu Arg Leu Tyr Pro Ala Gly Pro Leu Leu Phe
            355                 360                 365

Pro His Glu Ser Ser Ala Asp Cys Val Ile Ser Gly Tyr Asn Ile Pro
        370                 375                 380

Arg Gly Thr Met Leu Ile Val Asn Gln Trp Ala Ile His His Asp Pro
385                 390                 395                 400

Lys Val Trp Asp Asp Pro Glu Thr Phe Lys Pro Glu Arg Phe Gln Gly
                405                 410                 415

Leu Glu Gly Thr Arg Asp Gly Phe Lys Leu Met Pro Phe Gly Ser Gly
                420                 425                 430

Arg Arg Gly Cys Pro Gly Glu Gly Leu Ala Ile Arg Leu Leu Gly Met
            435                 440                 445

Thr Leu Gly Ser Val Ile Gln Cys Phe Asp Trp Glu Arg Val Gly Asp
        450                 455                 460

Glu Met Val Asp Met Thr Glu Gly Leu Gly Val Thr Leu Pro Lys Ala
465                 470                 475                 480

Val Pro Leu Val Ala Lys Cys Lys Pro Arg Ser Glu Met Thr Asn Leu
                485                 490                 495

Leu Ser Glu Leu
            500

<210> SEQ ID NO 11
<211> LENGTH: 435
<212> TYPE: PRT
<213> ORGANISM: Artificial Sequence
<220> FEATURE:
<223> OTHER INFORMATION: Synthetic: UGT40087 version 2

<400> SEQUENCE: 11

Met Asp Ala Ser Ser Ser Pro Leu His Ile Val Ile Phe Pro Trp Leu
1               5                   10                  15

Ala Phe Gly His Met Leu Ala Ser Leu Glu Leu Ala Glu Arg Leu Ala
                20                  25                  30

Ala Arg Gly His Arg Val Ser Phe Val Ser Thr Pro Arg Asn Ile Ser
            35                  40                  45

Arg Leu Arg Pro Val Pro Pro Ala Leu Ala Pro Leu Ile Asp Phe Val
        50                  55                  60

Ala Leu Pro Leu Pro Arg Val Asp Gly Leu Pro Asp Gly Ala Glu Ala
65                  70                  75                  80

Thr Ser Asp Ile Pro Pro Gly Lys Thr Glu Leu His Leu Lys Ala Leu
                85                  90                  95

Asp Gly Leu Ala Ala Pro Phe Ala Ala Phe Leu Asp Ala Ala Cys Ala
                100                 105                 110

Asp Gly Ser Thr Asn Lys Val Asp Trp Leu Phe Leu Asp Asn Phe Gln
            115                 120                 125
```

Tyr Trp Ala Ala Ala Ala Ala Asp His Lys Ile Pro Cys Ala Leu
            130                 135                 140

Asn Leu Thr Phe Ala Ala Ser Thr Ser Ala Glu Tyr Gly Val Pro Arg
145                 150                 155                 160

Val Glu Pro Pro Val Asp Gly Ser Thr Ala Ser Ile Leu Gln Arg Phe
                165                 170                 175

Val Leu Thr Leu Glu Lys Cys Gln Phe Val Ile Gln Arg Ala Cys Phe
            180                 185                 190

Glu Leu Glu Pro Glu Pro Leu Pro Leu Ser Asp Ile Phe Gly Lys
        195                 200                 205

Pro Val Ile Pro Tyr Gly Leu Val Pro Cys Pro Ala Glu Gly
210                 215                 220

His Lys Arg Glu His Gly Asn Ala Ala Leu Ser Trp Leu Asp Lys Gln
225                 230                 235                 240

Gln Pro Glu Ser Val Leu Phe Ile Ala Leu Gly Ser Glu Pro Pro Val
                245                 250                 255

Thr Val Glu Gln Leu His Glu Ile Ala Leu Gly Leu Glu Leu Ala Gly
            260                 265                 270

Thr Thr Phe Leu Trp Ala Leu Lys Lys Pro Asn Gly Leu Leu Leu Glu
        275                 280                 285

Ala Asp Gly Asp Ile Leu Pro Pro Gly Phe Glu Glu Arg Thr Arg Asp
290                 295                 300

Arg Gly Leu Val Ala Met Gly Trp Val Pro Gln Pro Ile Ile Leu Ala
305                 310                 315                 320

His Ser Ser Val Gly Ala Phe Leu Thr His Gly Trp Ala Ser Thr
                325                 330                 335

Ile Glu Gly Val Met Ser Gly His Pro Met Leu Phe Leu Thr Phe Leu
            340                 345                 350

Asp Glu Gln Arg Ile Asn Ala Gln Leu Ile Glu Arg Lys Lys Ala Gly
        355                 360                 365

Leu Arg Val Pro Arg Arg Glu Lys Asp Gly Ser Tyr Asp Arg Gln Gly
370                 375                 380

Ile Ala Gly Ala Ile Arg Ala Val Met Cys Glu Glu Ser Lys Ser
385                 390                 395                 400

Val Phe Ala Ala Asn Ala Lys Lys Met Gln Glu Ile Val Ser Asp Arg
                405                 410                 415

Asn Cys Gln Glu Lys Tyr Ile Asp Glu Leu Ile Gln Arg Leu Gly Ser
            420                 425                 430

Phe Glu Lys
        435

<210> SEQ ID NO 12
<211> LENGTH: 435
<212> TYPE: PRT
<213> ORGANISM: Artificial Sequence
<220> FEATURE:
<223> OTHER INFORMATION: Synthetic: Si91Dlike

<400> SEQUENCE: 12

Met Asp Ser Ser Gln Ser Pro Pro Leu His Ile Ala Val Phe Pro Trp
1               5                   10                  15

Leu Ala Phe Gly His Leu Leu Pro Asn Leu Glu Leu Ala Glu Arg Leu
            20                  25                  30

Ala Ala Arg Gly His Arg Val Ser Phe Val Ser Thr Pro Arg Ile Ile
        35                  40                  45

-continued

```
Ser Arg Leu Arg Pro Val Pro Leu Ala Leu Ala Pro Leu Ile Asp Phe
 50                  55                  60

Val Ala Leu Pro Leu Pro Arg Val Asp Gly Leu Pro Asp Gly Ala Glu
 65                  70                  75                  80

Ala Thr Ser Asp Ile Pro Pro Gly Lys Thr Asp Leu His Leu Lys Ala
                 85                  90                  95

Leu Asp Gly Leu Ala Ala Pro Phe Ala Ala Phe Leu Asp Ala Ala Cys
            100                 105                 110

Ala Asp Gly Ser Thr Asn Lys Val Asp Trp Leu Phe Val Asp Ser Phe
        115                 120                 125

Gln Tyr Trp Ala Ala Ala Ala Asp Arg Lys Ile Pro Cys Ala
    130                 135                 140

Leu Ile Leu Pro Phe Ala Ser Ser Thr Leu Ala Glu Phe Gly Val Pro
145                 150                 155                 160

Arg Leu Glu Pro Pro Val Gly Ser Thr Ala Ser Ile Leu Gln Arg
                165                 170                 175

Phe Val Leu Thr Phe Glu Lys Cys Gln Leu Val Ile His Arg Ala Cys
                180                 185                 190

Ser Glu Leu Glu Pro Glu His Thr Pro Leu Leu Pro Gly Ile Phe Gly
            195                 200                 205

Lys Pro Val Ile Gln Tyr Gly Leu Val Pro Cys Pro Pro Ala Gln
210                 215                 220

Gly His Ile Glu His Asp Asn Ala Ala Leu Ser Trp Leu Asp Lys Gln
225                 230                 235                 240

Gln Pro Glu Ser Val Leu Phe Ile Ala Leu Gly Ser Glu Pro Pro Val
                245                 250                 255

Thr Val Glu Gln Leu His Glu Ile Ala Leu Gly Leu Glu Leu Ala Gly
            260                 265                 270

Thr Thr Phe Leu Trp Ala Leu Lys Lys Pro Asn Gly Leu Leu Leu Glu
        275                 280                 285

Ala Asp Gly Asp Ile Leu Pro Pro Gly Phe Glu Glu Arg Thr Arg Asp
    290                 295                 300

Arg Gly Leu Val Ala Met Gly Trp Val Pro Gln Leu Ser Ile Leu Ala
305                 310                 315                 320

His Ser Ser Val Gly Ala Phe Leu Thr His Gly Gly Trp Ser Ser Thr
                325                 330                 335

Ile Glu Gly Ala Met Ser Gly His Pro Met Val Phe Leu Thr Phe Leu
            340                 345                 350

Asp Glu Gln Arg Ile Asn Ala Gln Leu Ile Glu Arg Lys Lys Ala Gly
        355                 360                 365

Leu Arg Val Pro Arg Cys Glu Lys Asp Gly Ser Tyr Asp Arg Gln Gly
    370                 375                 380

Ile Ala Gly Ala Ile Arg Ala Val Met Cys Glu Glu Ser Lys Ser
385                 390                 395                 400

Val Phe Ala Ala Asn Ala Lys Lys Met Gln Glu Ile Ile Asn Asp Arg
                405                 410                 415

Lys Cys Gln Glu Arg Tyr Ile Asp Glu Leu Ile Gln Arg Leu Arg Ser
            420                 425                 430

Phe Glu Lys
        435

<210> SEQ ID NO 13
<211> LENGTH: 1308
```

```
<212> TYPE: DNA
<213> ORGANISM: Artificial Sequence
<220> FEATURE:
<223> OTHER INFORMATION: Synthetic: UGT40087-1 codon optimized nucleic
      acid sequence

<400> SEQUENCE: 13
atggatgctt ccagtagtcc tttacacatc gttatctttc catggttagc tttcggtcat      60
atgttggctt ccttggaatt ggctgagaga ttggctgctc gtggtcacag agtctccttc     120
gtttccaccc ctagaaacat tctagatta cgtccagttc caccagcttt agctccattg      180
attgattttg tcgctttgcc attgccctaga gtcgatggtt accagatgg tgccgaagct     240
acctctgaca ttccaccagg taagaccgaa ttacacttga aggctttgga cggtttggct     300
gctccattcg ccgctttttt ggacgctgcc tgtgctgatg ttccaccaa caaggttgat      360
tggttgtttt tggacaactt ccaatactgg gctgccgctg ccgctgctga tcacaaaatt     420
ccttgcgcct taaacttgac ttttgccgct tccacctccg ctgaatacgg tgttccacgt     480
gttgaaccac cagttgacgg ttccactgcc tccatcttac aaagatttgt cttaacctta     540
gaaaaatgtc aattcgttat ccaaagagct tgtttcgaat tggaacctga accattgcca     600
ttgttgtccg acattttcgg taagccagtc atcccatacg gtttagttcc tccatgtcca     660
ccagctgaag gtcacaaaag agaacacggt aacgctgctt tgtcctggtt ggataagcaa     720
caaccagaat ctgttttgtt catcgctttg ggttctgaac cacctgttac cgtcgaacaa     780
ttgcacgaaa tcgctttggg tttagaattg gccggtacca ccttcttgtg ggccttgaaa     840
aagccaaacg gttgttgtt agaagccgat ggtgatattt tgccaccagg tttcgaagaa     900
agaactagag atagaggttt agtcgctatg ggttgggttc cacaaccaat tatcttggcc     960
cattcctctg ttggtgcctt tttgactcac ggtggttggg cctccactat tgaaggtgtc    1020
atgtccggtc accctatgtt gttcttaacc ttcttggacg aacaacgtat caacgcccaa    1080
ttgatcgaaa gaaaaaggc tggtttaaga gtcccaagaa gagaaaagga tggttcctac    1140
gacagacaag gtattgctgg tgctattaga gccgtcatgt gtgaagaaga atctaagtct    1200
gtcttcgctg ctaacgctaa gaaaatgcaa gagatcgttt ctgacagaaa ctgtcaagaa    1260
aagtacatcg acgaattgat tcaaagattg ggttctttcg aaaagtaa                 1308

<210> SEQ ID NO 14
<211> LENGTH: 21
<212> TYPE: PRT
<213> ORGANISM: Artificial Sequence
<220> FEATURE:
<223> OTHER INFORMATION: Synthetic: loop2 from Os_UGT_91C1

<400> SEQUENCE: 14

Glu Gly Leu Pro Asp Gly Ala Glu Ser Thr Asn Asp Val Pro His Asp
1               5                   10                  15
Arg Pro Asp Met Val
            20

<210> SEQ ID NO 15
<211> LENGTH: 10
<212> TYPE: PRT
<213> ORGANISM: Artificial Sequence
<220> FEATURE:
<223> OTHER INFORMATION: Synthetic: loop3_1 from Os_UGT_91C1

<400> SEQUENCE: 15

Ser Glu Phe Leu Gly Thr Ala Cys Ala Asp
```

<210> SEQ ID NO 16
<211> LENGTH: 19
<212> TYPE: PRT
<213> ORGANISM: Artificial Sequence
<220> FEATURE:
<223> OTHER INFORMATION: Synthetic: loop3_2 from Os_UGT_91C1

<400> SEQUENCE: 16

Ser Glu Phe Leu Gly Thr Ala Cys Ala Asp Trp Val Ile Val Asp Val
1               5                   10                  15

Phe His His

<210> SEQ ID NO 17
<211> LENGTH: 43
<212> TYPE: PRT
<213> ORGANISM: Artificial Sequence
<220> FEATURE:
<223> OTHER INFORMATION: Synthetic: loop4_1 from Os_UGT_91C1

<400> SEQUENCE: 17

Ala Asp Arg Arg Leu Glu Arg Ala Glu Thr Glu Ser Pro Ala Ala Ala
1               5                   10                  15

Gly Gln Gly Arg Pro Ala Ala Ala Pro Thr Phe Glu Val Ala Arg Met
            20                  25                  30

Lys Leu Ile Arg Thr Lys Gly Ser Ser Gly Met
        35                  40

<210> SEQ ID NO 18
<211> LENGTH: 56
<212> TYPE: PRT
<213> ORGANISM: Artificial Sequence
<220> FEATURE:
<223> OTHER INFORMATION: Synthetic: loop4_2 from Os_UGT_91C1

<400> SEQUENCE: 18

Met Met Leu Leu Gly Ser Ala His Met Ile Ala Ser Ile Ala Asp Arg
1               5                   10                  15

Arg Leu Glu Arg Ala Glu Thr Glu Ser Pro Ala Ala Ala Gly Gln Gly
            20                  25                  30

Arg Pro Ala Ala Ala Pro Thr Phe Glu Val Ala Arg Met Lys Leu Ile
        35                  40                  45

Arg Thr Lys Gly Ser Ser Gly Met
    50                  55

<210> SEQ ID NO 19
<211> LENGTH: 18
<212> TYPE: PRT
<213> ORGANISM: Artificial Sequence
<220> FEATURE:
<223> OTHER INFORMATION: Synthetic: loop2 from UGT40087

<400> SEQUENCE: 19

Asp Gly Leu Pro Asp Gly Ala Glu Ala Thr Ser Asp Ile Pro Pro Gly
1               5                   10                  15

Lys Thr

<210> SEQ ID NO 20
<211> LENGTH: 17
<212> TYPE: PRT
<213> ORGANISM: Artificial Sequence
<220> FEATURE:

-continued

<223> OTHER INFORMATION: Synthetic: loop3_1 from UGT40087

<400> SEQUENCE: 20

Ala Ala Phe Leu Asp Ala Ala Cys Ala Asp Gly Ser Thr Asn Lys Val
1               5                   10                  15

Asp

<210> SEQ ID NO 21
<211> LENGTH: 26
<212> TYPE: PRT
<213> ORGANISM: Artificial Sequence
<220> FEATURE:
<223> OTHER INFORMATION: Synthetic: loop3_2 from UGT40087

<400> SEQUENCE: 21

Ala Ala Phe Leu Asp Ala Ala Cys Ala Asp Gly Ser Thr Asn Lys Val
1               5                   10                  15

Asp Trp Leu Phe Leu Asp Asn Phe Gln Tyr
            20                  25

<210> SEQ ID NO 22
<211> LENGTH: 14
<212> TYPE: PRT
<213> ORGANISM: Artificial Sequence
<220> FEATURE:
<223> OTHER INFORMATION: Synthetic: loop4_1 from UGT40087

<400> SEQUENCE: 22

Gly Val Pro Arg Val Glu Pro Pro Val Asp Gly Ser Thr Ala
1               5                   10

<210> SEQ ID NO 23
<211> LENGTH: 27
<212> TYPE: PRT
<213> ORGANISM: Artificial Sequence
<220> FEATURE:
<223> OTHER INFORMATION: Synthetic: loop4_2 from UGT40087

<400> SEQUENCE: 23

Leu Asn Leu Thr Phe Ala Ala Ser Thr Ser Ala Glu Tyr Gly Val Pro
1               5                   10                  15

Arg Val Glu Pro Pro Val Asp Gly Ser Thr Ala
            20                  25

<210> SEQ ID NO 24
<211> LENGTH: 434
<212> TYPE: PRT
<213> ORGANISM: Artificial Sequence
<220> FEATURE:
<223> OTHER INFORMATION: Synthetic: UGT40087/Si91Dlike chimera

<400> SEQUENCE: 24

Met Asp Ala Ser Ser Ser Pro Leu His Ile Val Ile Phe Pro Trp Leu
1               5                   10                  15

Ala Phe Gly His Met Leu Ala Ser Leu Glu Leu Ala Glu Arg Leu Ala
            20                  25                  30

Ala Arg Gly His Arg Val Ser Phe Val Ser Thr Pro Arg Asn Ile Ser
        35                  40                  45

Arg Leu Arg Pro Val Pro Pro Ala Leu Ala Pro Leu Ile Asp Phe Val
    50                  55                  60

Ala Leu Pro Leu Pro Arg Val Asp Gly Leu Pro Asp Gly Ala Glu Ala
65                  70                  75                  80

```
Thr Ser Asp Ile Pro Pro Gly Lys Thr Glu Leu His Leu Lys Ala Leu
                85                  90                  95
Asp Gly Leu Ala Ala Pro Phe Ala Ala Phe Leu Asp Ala Ala Cys Ala
            100                 105                 110
Asp Gly Ser Thr Asn Lys Val Asp Trp Leu Phe Leu Asp Asn Phe Gln
        115                 120                 125
Tyr Trp Ala Ala Ala Ala Ala Asp His Lys Ile Pro Cys Ala Leu
    130                 135                 140
Asn Leu Thr Phe Ala Ala Ser Thr Ser Ala Glu Tyr Gly Val Pro Arg
145                 150                 155                 160
Val Glu Pro Pro Val Asp Gly Ser Thr Ala Ser Ile Leu Gln Arg Phe
                165                 170                 175
Val Leu Thr Leu Glu Lys Cys Gln Phe Val Ile Gln Arg Ala Cys Phe
            180                 185                 190
Glu Leu Glu Pro Glu Pro Leu Pro Leu Leu Ser Asp Ile Phe Gly Lys
        195                 200                 205
Pro Val Ile Pro Tyr Gly Leu Val Pro Cys Pro Pro Ala Gln Gly
    210                 215                 220
His Ile Glu His Asp Asn Ala Ala Leu Ser Trp Leu Asp Lys Gln Gln
225                 230                 235                 240
Pro Glu Ser Val Leu Phe Ile Ala Leu Gly Ser Glu Pro Val Thr
                245                 250                 255
Val Glu Gln Leu His Glu Ile Ala Leu Gly Leu Glu Leu Ala Gly Thr
            260                 265                 270
Thr Phe Leu Trp Ala Leu Lys Lys Pro Asn Gly Leu Leu Leu Glu Ala
        275                 280                 285
Asp Gly Asp Ile Leu Pro Pro Gly Phe Glu Glu Arg Thr Arg Asp Arg
290                 295                 300
Gly Leu Val Ala Met Gly Trp Val Pro Gln Leu Ser Ile Leu Ala His
305                 310                 315                 320
Ser Ser Val Gly Ala Phe Leu Thr His Gly Gly Trp Ser Ser Thr Ile
                325                 330                 335
Glu Gly Ala Met Ser Gly His Pro Met Val Phe Leu Thr Phe Leu Asp
            340                 345                 350
Glu Gln Arg Ile Asn Ala Gln Leu Ile Glu Arg Lys Lys Ala Gly Leu
        355                 360                 365
Arg Val Pro Arg Cys Glu Lys Asp Gly Ser Tyr Asp Arg Gln Gly Ile
    370                 375                 380
Ala Gly Ala Ile Arg Ala Val Met Cys Glu Glu Glu Ser Lys Ser Val
385                 390                 395                 400
Phe Ala Ala Asn Ala Lys Lys Met Gln Glu Ile Ile Asn Asp Arg Lys
                405                 410                 415
Cys Gln Glu Arg Tyr Ile Asp Glu Leu Ile Gln Arg Leu Arg Ser Phe
            420                 425                 430
Glu Lys

<210> SEQ ID NO 25
<211> LENGTH: 433
<212> TYPE: PRT
<213> ORGANISM: Artificial Sequence
<220> FEATURE:
<223> OTHER INFORMATION: Synthetic: Os_UGT_91C1_loop4_1

<400> SEQUENCE: 25

Met Asp Ser Gly Tyr Ser Ser Ser Tyr Ala Ala Ala Ala Gly Met His
```

```
1               5                   10                  15
Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
            50                  55                  60

Ala Pro Leu Val Ala Phe Val Ala Leu Pro Leu Pro Arg Val Glu Gly
65                      70                  75                  80

Leu Pro Asp Gly Ala Glu Ser Thr Asn Asp Val Pro His Asp Arg Pro
                    85                  90                  95

Asp Met Val Glu Leu His Arg Arg Ala Phe Asp Gly Leu Ala Ala Pro
                    100                 105                 110

Phe Ser Glu Phe Leu Gly Thr Ala Cys Ala Asp Trp Val Ile Val Asp
                    115                 120                 125

Val Phe His His Trp Ala Ala Ala Ala Leu Glu His Lys Val Pro
                    130                 135                 140

Cys Ala Met Met Leu Leu Gly Ser Ala His Met Ile Ala Ser Ile Gly
145                     150                 155                 160

Val Pro Arg Val Glu Pro Pro Val Asp Gly Ser Thr Ala Ser Leu Ala
                    165                 170                 175

Glu Arg Phe Ser Leu Thr Leu Ser Arg Ser Ser Leu Val Val Gly Arg
                    180                 185                 190

Ser Cys Val Glu Phe Glu Pro Glu Thr Val Pro Leu Leu Ser Thr Leu
                    195                 200                 205

Arg Gly Lys Pro Ile Thr Phe Leu Gly Leu Met Pro Pro Leu His Glu
                    210                 215                 220

Gly Arg Arg Glu Asp Gly Glu Asp Ala Thr Val Arg Trp Leu Asp Ala
225                     230                 235                 240

Gln Pro Ala Lys Ser Val Val Tyr Val Ala Leu Gly Ser Glu Val Pro
                    245                 250                 255

Leu Gly Val Glu Lys Val His Glu Leu Ala Leu Gly Leu Glu Leu Ala
                    260                 265                 270

Gly Thr Arg Phe Leu Trp Ala Leu Arg Lys Pro Thr Gly Val Ser Asp
                    275                 280                 285

Ala Asp Leu Leu Pro Ala Gly Phe Glu Glu Arg Thr Arg Gly Arg Gly
                    290                 295                 300

Val Val Ala Thr Arg Trp Val Pro Gln Met Ser Ile Leu Ala His Ala
305                     310                 315                 320

Ala Val Gly Ala Phe Leu Thr His Cys Gly Trp Asn Ser Thr Ile Glu
                    325                 330                 335

Gly Leu Met Phe Gly His Pro Leu Ile Met Leu Pro Ile Phe Gly Asp
                    340                 345                 350

Gln Gly Pro Asn Ala Arg Leu Ile Glu Ala Lys Asn Ala Gly Leu Gln
                    355                 360                 365

Val Ala Arg Asn Asp Gly Asp Gly Ser Phe Arg Glu Gly Val Ala
                    370                 375                 380

Ala Ala Ile Arg Ala Val Ala Val Glu Glu Ser Ser Lys Val Phe
385                     390                 395                 400

Gln Ala Lys Ala Lys Lys Leu Gln Glu Ile Val Ala Asp Met Ala Cys
                    405                 410                 415

His Glu Arg Tyr Ile Asp Gly Phe Ile Gln Gln Leu Arg Ser Tyr Lys
                    420                 425                 430
```

Asp

<210> SEQ ID NO 26
<211> LENGTH: 1621
<212> TYPE: DNA
<213> ORGANISM: Artificial Sequence
<220> FEATURE:
<223> OTHER INFORMATION: Synthetic: unoptimized nucleic acid sequence of
      UGT40087 having SEQ ID NO:1

<400> SEQUENCE: 26

```
tcgtgacgca acagagcaac tctcgccggc accggtcgcc ccttccgcag gcaggcagca      60
ggctcgcgcg catggacgcc tccgactcct ccccgctgca catcgtcatc ttcccgtggc     120
tcgcgttcgg ccacatgctc gccagcctgg agctcgccga gcgcctggcc gcgcgaggcc     180
accgcgtgtc cttcgtctcc accccgcgca acatcagccg cctccgcccg gtcccgcccg     240
cgctggcgcc gctcatcgac ttcgtggcgc tgccgctgcc gcgcgtcgac ggcctccccg     300
acggcgcgga ggccaccagc gacatcccgc cggcaagac cgagctccac ctcaaggccc     360
tagacggcct cgccgcgccc ttcgcagctt cctcgacgc cgcctgcgcc gacgggagca     420
ccaacaaggt ggactggctc ttcctcgaca acttccaata ctgggccgcc gccgcgctg     480
ccgaccataa gatacccctgc gcgctgaacc tgacattcgc agcgtcgacg tcagcggagt     540
acggtgtgcc acgcgttgag ccgccggtgg atggctcaac agcctcaata ctccagcgat     600
ttgtgctaac cttggagaaa tgccagtttg tcatccaacg cgcctgcttc gagctggagc     660
cggagcccct gcctctcctg tcagacatct tcggcaagcc ggtgatcccg tacggcctag     720
tcccgccgtg tcccccgca gaaggtcaca aaagagagca cggcaacgca gctctgtcat     780
ggctcgacaa gcagcagccc gagtctgtcc tgttcattgc tctgggaagc gagcctccgg     840
tgaccgtcga acagctgcac gagatcgcgc ttgggctgga gctcgccggg acgacattcc     900
tctgggctct gaagaagcct aacgcctcc tcctcgaggc ggacggcgac atcctgcccc     960
caggtttcga ggagcggacg cgtgaccgtg ggctcgtggc catgggctgg gttcctcagc    1020
ccatcatact ggctcacagc tccgtgggcg cgttcctgac gcacggcgga tgggcctcca    1080
ccattgaagg ggttatgtcc gggcatccca tgctcttcct gacgttctta gatgaacaga    1140
ggataaacgc gcaactgatc gagaggaaga aggccgggtt gcgagtgcca aggcgtgaga    1200
aggacggctc gtacgatcgc caaggcatcg ccggagcgat ccgggctgtc atgtgcgagg    1260
aagaaagtaa gagcgtcttc gcggctaatg ccaagaagat gcaggagatt gtgagcgaca    1320
ggaattgcca ggagaagtac atcgacgagc ttatccagcg tctgggatcc ttcgagaagt    1380
gaaataaggt gaaatatcct acaataaccg cctgttgatg gcttgatgca acgatgtagg    1440
tggccattcg cgcctctgat ctccatgttc cggcaataaa tccaccatat gttatggctc    1500
tgacttactg aatttcctaa tatgtatgcc caaacacatg cataggttgc tagttgcccc    1560
tcgcgccggc attagcgata atgtcaccgc agtcgccagc acaggtgtag caatttgaca    1620
t                                                                   1621
```

<210> SEQ ID NO 27
<211> LENGTH: 17
<212> TYPE: PRT
<213> ORGANISM: Artificial Sequence
<220> FEATURE:
<223> OTHER INFORMATION: Synthetic: modified loop1 from Os_UGT_91C1
      present in UGT40087_loop1

```
<400> SEQUENCE: 27

Thr Pro Arg Asn Ile Ser Arg Leu Pro Pro Val Pro Ala Leu Ala
1               5                   10                  15

Pro

<210> SEQ ID NO 28
<211> LENGTH: 17
<212> TYPE: PRT
<213> ORGANISM: Artificial Sequence
<220> FEATURE:
<223> OTHER INFORMATION: Synthetic: modified loop1 from UGT40087 present
      in Os_UGT_91C1_loop1

<400> SEQUENCE: 28

Thr Pro Arg Asn Ile Ser Arg Leu Arg Pro Val Arg Pro Ala Leu Ala
1               5                   10                  15

Pro

<210> SEQ ID NO 29
<211> LENGTH: 17
<212> TYPE: PRT
<213> ORGANISM: Artificial Sequence
<220> FEATURE:
<223> OTHER INFORMATION: Synthetic: loop1 from Os_UGT_91C1 having SEQ ID
      NO:8

<400> SEQUENCE: 29

Thr Pro Arg Asn Ile Ser Arg Leu Pro Pro Val Arg Pro Ala Leu Ala
1               5                   10                  15

Pro

<210> SEQ ID NO 30
<211> LENGTH: 17
<212> TYPE: PRT
<213> ORGANISM: Artificial Sequence
<220> FEATURE:
<223> OTHER INFORMATION: Synthetic: loop1 from UGT40087 having SEQ ID
      NO:11

<400> SEQUENCE: 30

Thr Pro Arg Asn Ile Ser Arg Leu Arg Pro Val Pro Pro Ala Leu Ala
1               5                   10                  15

Pro

<210> SEQ ID NO 31
<211> LENGTH: 460
<212> TYPE: PRT
<213> ORGANISM: Artificial Sequence
<220> FEATURE:
<223> OTHER INFORMATION: Synthetic polypeptide

<400> SEQUENCE: 31

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
                20                  25                  30

Arg Leu Ile Ser Lys Gly Val Lys Thr Thr Leu Val Thr Thr Ile His
            35                  40                  45

Thr Leu Asn Ser Thr Leu Asn His Ser Asn Thr Thr Thr Thr Ser Ile
        50                  55                  60

Glu Ile Gln Ala Ile Ser Asp Gly Cys Asp Glu Gly Gly Phe Met Ser
65                  70                  75                  80
```

Ala Gly Glu Ser Tyr Leu Glu Thr Phe Lys Gln Val Gly Lys Ser
            85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
            115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
            165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
            195                 200                 205

Phe Thr Asn Ser Phe Tyr Lys Leu Glu Glu Glu Val Ile Glu Trp Thr
210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
            245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
            275                 280                 285

Pro Glu Gln Val Glu Glu Ile Thr Arg Ala Leu Ile Asp Ser Asp Val
            290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
            370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
            405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
450                 455                 460

<210> SEQ ID NO 32
<211> LENGTH: 458
<212> TYPE: PRT
<213> ORGANISM: Artificial Sequence
<220> FEATURE:

<223> OTHER INFORMATION: Synthetic polypeptide

<400> SEQUENCE: 32

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400
```

```
Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 33
<211> LENGTH: 481
<212> TYPE: PRT
<213> ORGANISM: Stevia rebaudiana

<400> SEQUENCE: 33

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
    210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
    290                 295                 300

Thr Val Met Ser Leu Glu Asp Met Thr Glu Phe Gly Trp Gly Leu Ala
305                 310                 315                 320
```

```
Asn Ser Asn His Tyr Phe Leu Trp Ile Ile Arg Ser Asn Leu Val Ile
            325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
        370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
            405                 410                 415

Leu Glu Met Gly Thr Lys Val Lys Arg Asp Glu Val Lys Arg Leu Val
            420                 425                 430

Gln Glu Leu Met Gly Glu Gly Gly His Lys Met Arg Asn Lys Ala Lys
            435                 440                 445

Asp Trp Lys Glu Lys Ala Arg Ile Ala Ile Ala Pro Asn Gly Ser Ser
        450                 455                 460

Ser Leu Asn Ile Asp Lys Met Val Lys Glu Ile Thr Val Leu Ala Arg
465                 470                 475                 480

Asn
```